(12) United States Patent
Palermo et al.

(10) Patent No.: US 11,944,530 B2
(45) Date of Patent: Apr. 2, 2024

(54) VASCULAR AND AORTIC GRAFTS AND DEPLOYMENT TOOLS

(71) Applicant: Aquedeon Medical, Inc., Los Altos, CA (US)

(72) Inventors: Thomas J. Palermo, San Jose, CA (US); Pin-Hsuan Lee, Taipei (TW); Jimmy Jen, San Jose, CA (US)

(73) Assignee: Aquedeon Medical, Inc., Sunnyvale, CA (US)

( * ) Notice: Subject to any disclaimer, the term of this patent is extended or adjusted under 35 U.S.C. 154(b) by 0 days.

(21) Appl. No.: 16/730,188

(22) Filed: Dec. 30, 2019

(65) Prior Publication Data

US 2021/0000584 A1    Jan. 7, 2021

Related U.S. Application Data

(63) Continuation-in-part of application No. 16/502,539, filed on Jul. 3, 2019, now abandoned.
(Continued)

(51) Int. Cl.
*A61F 2/06* (2013.01)
*A61F 2/95* (2013.01)
*A61F 2/966* (2013.01)

(52) U.S. Cl.
CPC .................. *A61F 2/06* (2013.01); *A61F 2/95* (2013.01); *A61F 2002/067* (2013.01);
(Continued)

(58) Field of Classification Search
CPC .... A61F 2/07; A61F 2/90; A61F 2/958; A61F 2/89; A61F 2/962; A61F 2002/9511;
(Continued)

(56) References Cited

U.S. PATENT DOCUMENTS 6,254,593 B1   7/2001   Wilson
6,352,561 B1   3/2002   Leopold et al.
(Continued)

FOREIGN PATENT DOCUMENTS

DE   102013106463   12/2014
EP   2111826 A1    6/2009
(Continued)

OTHER PUBLICATIONS

International Search Report and Written Opinion from International Patent Application No. PCT/US2019/068955, dated May 12, 2020.
(Continued)

*Primary Examiner* — Matthew J Lawson
*Assistant Examiner* — Rebecca Lynee Zimmerman
(74) *Attorney, Agent, or Firm* — Dergosits & Noah LLP; Todd A. Noah

(57) ABSTRACT

A vascular graft may be configured to transition from an insertion state to a deployed state. The graft comprising a proximal end having an expandable mesh, a distal end having an expandable mesh, and at least one suture cuff positioned between the proximal and distal ends, wherein each suture cuff comprises additional material relative to the proximal and distal ends that is configured to form when the vascular graft transitions from the insertion state to the deployed state.

5 Claims, 62 Drawing Sheets

Related U.S. Application Data

(60) Provisional application No. 62/906,041, filed on Sep. 25, 2019.

(52) U.S. Cl.
CPC ..... *A61F 2002/9505* (2013.01); *A61F 2/9517* (2020.05); *A61F 2002/9665* (2013.01)

(58) Field of Classification Search
CPC ...... A61F 2220/0075; A61F 2230/0004; A61F 2220/0008; A61F 2002/061; A61F 2/064; A61F 2/97; A61F 2/06; A61F 2/9517; A61F 2002/067; A61F 2002/9665; A61F 2/9662; A61F 2/954; A61F 2/95; A61F 2002/075; A61B 17/3478; A61B 17/1227; A61B 17/12045; A61B 17/12136; A61B 2017/1132; A61B 2017/1107

See application file for complete search history.

(56) References Cited

U.S. PATENT DOCUMENTS

| | | | |
|---|---|---|---|
| 8,641,752 | B1 | 2/2014 | Holm et al. |
| 8,778,006 | B2 | 7/2014 | Faraghi et al. |
| 9,192,500 | B1 | 11/2015 | Longo |
| 9,763,819 | B1 | 9/2017 | Sondreaal |
| 10,363,155 | B2 | 7/2019 | Lesmeister et al. |
| 2003/0139805 | A1 | 7/2003 | Holmberg et al. |
| 2004/0044395 | A1 | 3/2004 | Nelson |
| 2004/0064081 | A1* | 4/2004 | Stanish ............ A61F 2/06 623/1.36 |
| 2005/0033410 | A1 | 2/2005 | Hogendijk et al. |
| 2005/0080430 | A1 | 4/2005 | Wright et al. |
| 2008/0132993 | A1* | 6/2008 | Rasmussen ........ A61F 2/89 623/1.13 |
| 2008/0288042 | A1 | 11/2008 | Purdy et al. |
| 2009/0125097 | A1 | 5/2009 | Bruszewski et al. |
| 2011/0288580 | A1* | 11/2011 | Ginn ............ A61B 17/0057 606/213 |
| 2012/0065590 | A1 | 3/2012 | Bierman et al. |
| 2013/0282103 | A1 | 10/2013 | Madjarov et al. |
| 2013/0310853 | A1* | 11/2013 | Zaugg ............ A61B 17/0401 606/232 |
| 2015/0066131 | A1 | 3/2015 | Luong et al. |
| 2016/0022454 | A1 | 1/2016 | Bonutti |
| 2016/0270936 | A1 | 9/2016 | Berra et al. |
| 2016/0287417 | A1 | 10/2016 | Bhave et al. |
| 2018/0000619 | A1 | 1/2018 | Longo |
| 2018/0085240 | A1 | 3/2018 | Mower et al. |
| 2018/0193043 | A1 | 7/2018 | Marchand et al. |
| 2019/0083101 | A1 | 3/2019 | Broyles et al. |
| 2019/0151071 | A1 | 5/2019 | Mogensen |
| 2019/0247213 | A1 | 8/2019 | Lostetter |
| 2019/0365524 | A1* | 12/2019 | Wilger ............ A61F 2/06 |
| 2021/0000583 | A1 | 1/2021 | Palermo et al. |

FOREIGN PATENT DOCUMENTS

| | | | |
|---|---|---|---|
| JP | 2012065933 A | 4/2012 | |
| WO | 1998/0027894 | 7/1998 | |
| WO | WO-2009145913 A1 * | 12/2009 | ............ A61F 2/07 |
| WO | 2020010237 A1 | 1/2020 | |

OTHER PUBLICATIONS

International Search Report and Written Opinion in International Patent Application No. PCT/US2019/040566, dated Dec. 18, 2019.
Invitation to Pay Additional Fees and Partial Search Report in International Patent Application No. PCT/US2019/040566 dated Sep. 18, 2019.
International Search Report and Written Opinion from related International Patent Application No. PCT/ US2021/020800, dated Jun. 15, 2021.
Office Action from related U.S. Appl. No. 17/191,945, dated Jan. 9, 2023.

* cited by examiner

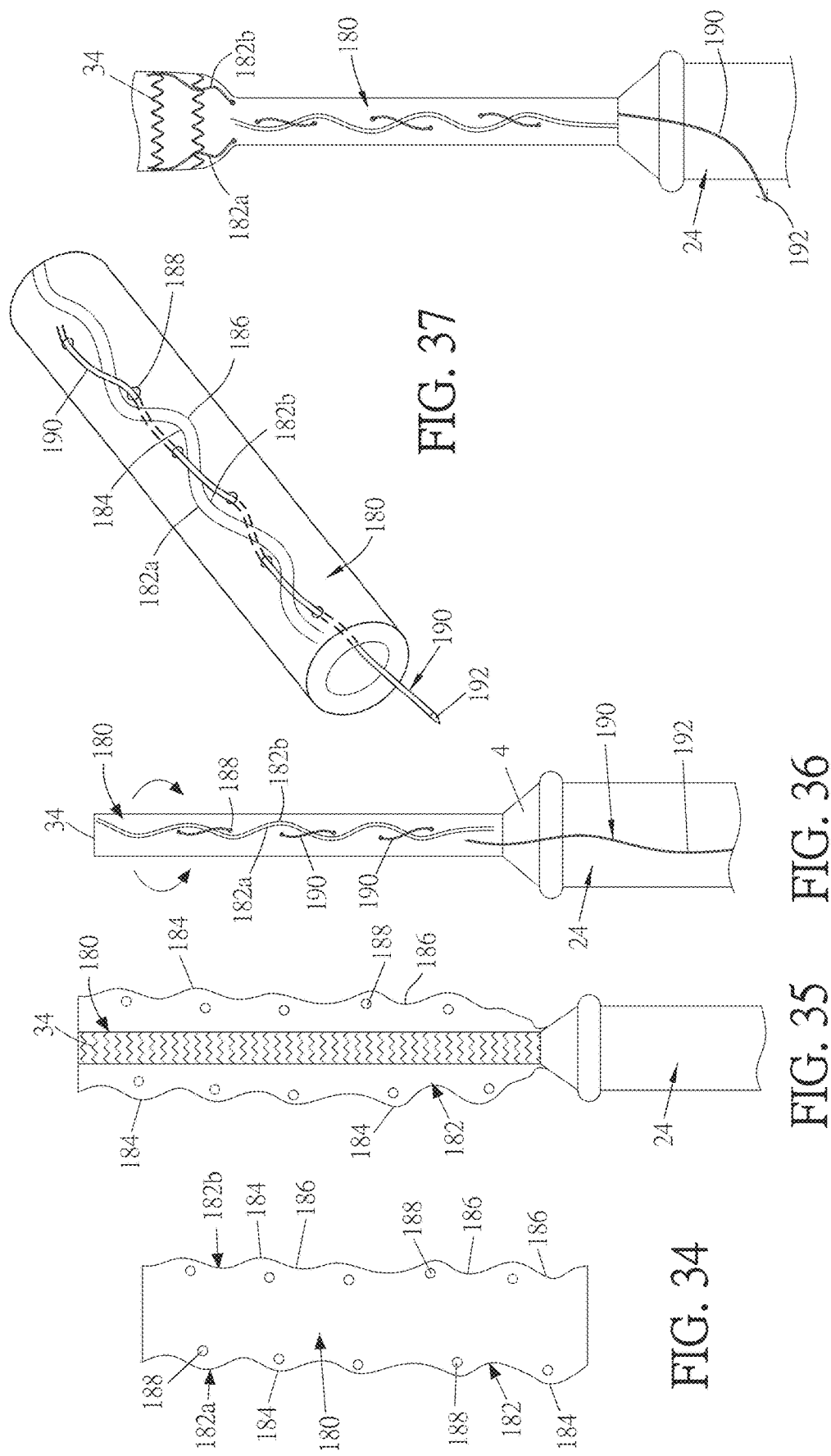

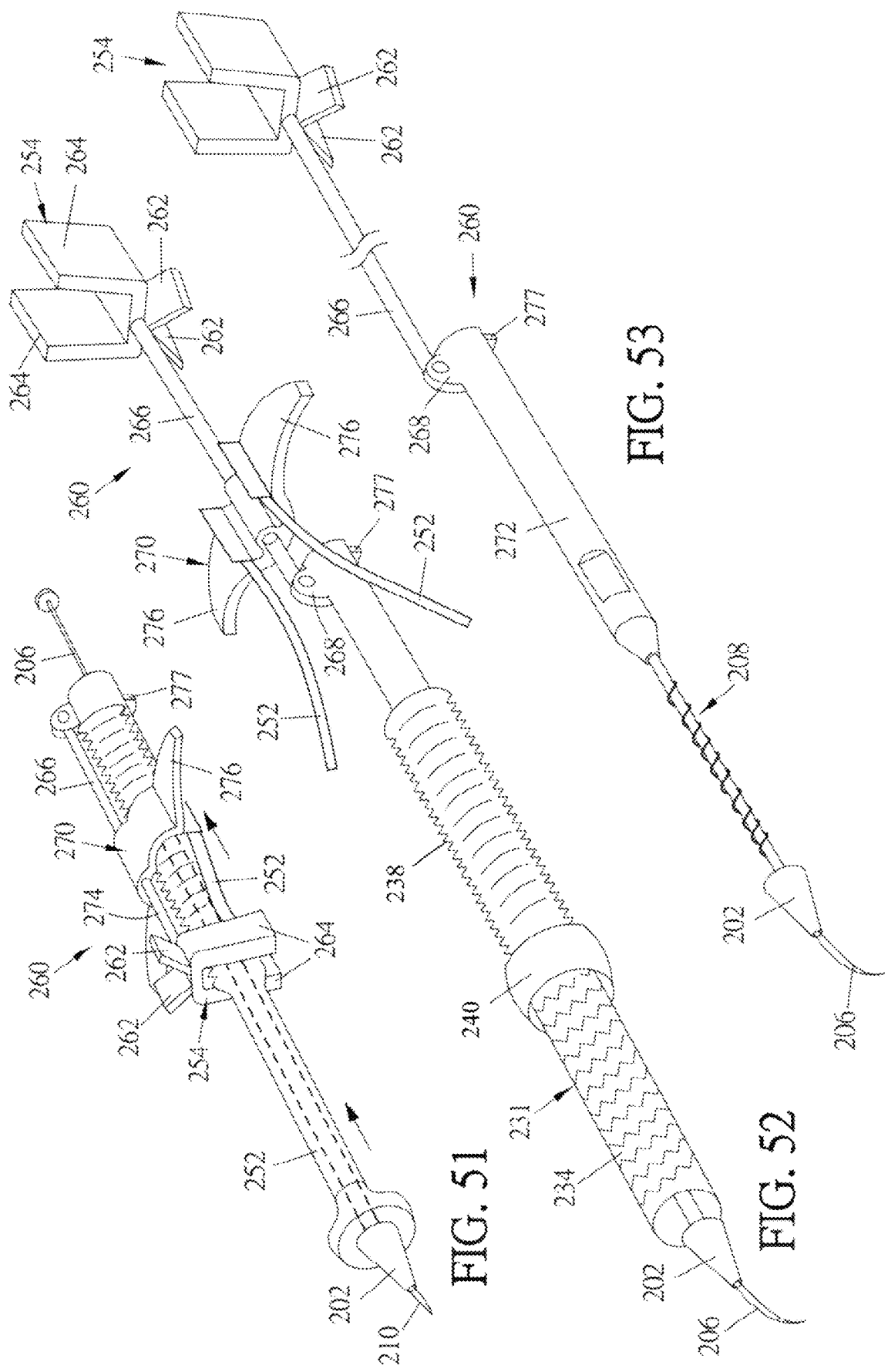

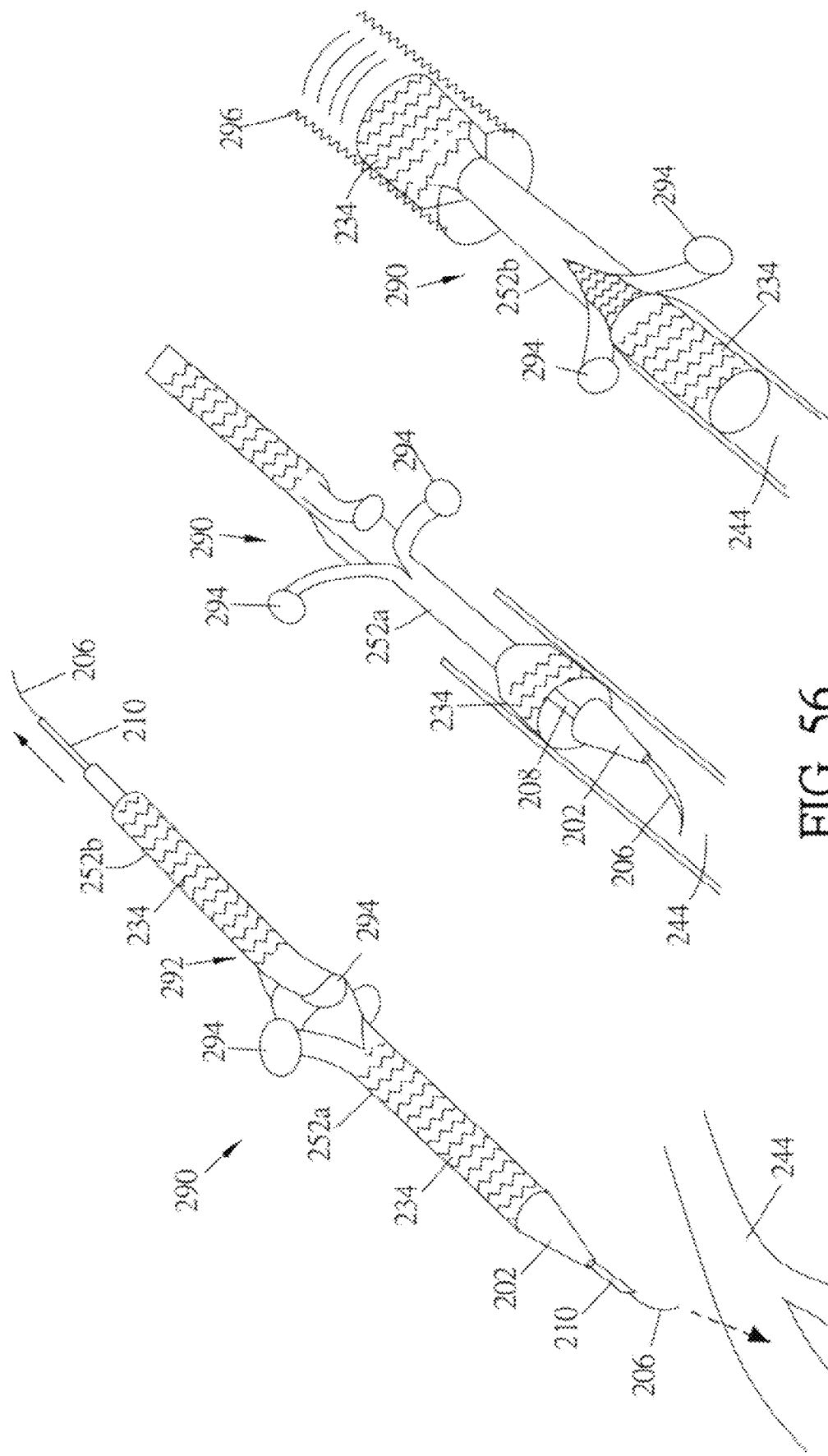

VASCULAR AND AORTIC GRAFTS AND DEPLOYMENT TOOLS

CROSS REFERENCE TO RELATED APPLICATION

This patent application is a continuation-in-part of U.S. patent application Ser. No. 16/502,539, filed Jul. 3, 2019 and claims priority to U.S. Provisional Patent Application No. 62/906,041, filed Sep. 25, 2019, both of which are hereby incorporated by reference in their entirety and for all purposes.

FIELD OF THE INVENTION

The invention generally relates to vascular and aortic grafts, and deployment tools for such grafts.

BACKGROUND

The circulatory system includes the aorta and other large-diameter blood vessels, as well as smaller-diameter blood vessels and capillaries. Although disease and other conditions that affect other blood vessels can be serious, disease and other conditions that affect the aorta may be more serious and more likely to result in patient death, due to the volume and pressure of blood that is pumped through the aorta.

Complex thoracic aortic disease encompasses acute (AAD) and chronic type A dissections (CAD), as well as aortic arch aneurysm (TAA) with or without involvement of the ascending and descending aorta.

Aortic dissection results from a tear in the inner layer of the wall of the aorta leading to blood entering and separating the layers of the wall. Acute aortic dissections are defined as those identified within the first 2 weeks after the initial tear, and chronic dissections are defined as those identified at times greater than 2 weeks. Aortic dissection is classified by its location and the extent of involvement of the thoracic aorta. Stanford Type A dissection affects the ascending aorta and may extend to the arch and descending thoracic aorta. Stanford Type B dissection does not affect the ascending aorta and typically involves the descending thoracic aorta, distal to the origin of the left subclavian artery. Approximately two-thirds of aortic dissections are Stanford Type A.

Patients with acute dissection typically present with pain and are classed as emergencies due to the risk of the dissection rupturing the wall of the aorta, affecting the integrity of the aortic valve and, through involvement of the origins of the coronary arteries, affecting perfusion of the myocardium.

Aortic aneurysm is a serious condition that can affect any segment of the aorta. An aortic aneurysm in the abdomen is referred to as an abdominal aortic aneurysm or AAA; an aortic aneurysm in the chest cavity is referred to as a thoracic aortic aneurysm, and an aneurysm in the chest cavity on the aortic arch may be referred to as an aortic arch aneurysm. Aortic aneurysms may result from different causes, such as untreated or severe hypertension, smoking, generic disease such as Marfan's syndrome, and degenerative dilation of the aortic wall. A thoracic aortic aneurysm results from weakening of the aortic wall, leading to localized dilatation, and is a life-threatening condition. Patients with thoracic aneurysms are often asymptomatic until the aneurysm expands. The most common presenting symptoms are pain and aortic rupture. A ruptured aneurysm can cause severe internal bleeding, which can rapidly lead to shock or death.

Treatment of complex thoracic aortic disease typically requires long and complicated open surgery. During such surgery, the patient is typically placed on a cardiopulmonary bypass pump, and the heart is stopped to allow the aorta to be clamped and operated upon. While the patient is on cardiopulmonary bypass, the patient generally is also chilled to a condition of hypothermia. The risk that the patient will not be able to survive the surgery is directly related to the duration of time that the patient spends on pump and under hypothermia.

SUMMARY

This disclosure includes a vascular graft configured to transition from an insertion state to a deployed state, and may feature a proximal end having an expandable mesh, a distal end having an expandable mesh, and at least one suture cuff positioned between the proximal and distal ends, wherein the suture cuffs comprise additional material relative to the proximal and distal ends that is configured to form when the vascular graft transitions from the insertion state to the deployed state. The transition from the insertion state to the deployed state may be a self-expanding expansion.

In one aspect, at least two suture cuffs may be positioned relatively closer to each other to the proximal and distal ends of the vascular graft. At least one of the suture cuffs may be formed at least in part by compression of the vascular graft substantially in the longitudinal direction. For example, at least one of the suture cuffs may have at least two longitudinal slits defined therethrough and wherein expansion of the vascular graft is configured to cause portions of the vascular graft located circumferentially between circumferentially-adjacent said longitudinal slits to form lobes extending radially outward from the vascular graft.

Correspondingly, this disclosure also includes a method for implanting a vascular graft within a patient by providing the vascular graft that may have a proximal end with an expandable mesh, a distal end with an expandable mesh and at least one suture cuff positioned between the proximal and distal ends. At least one end of the vascular graft may be positioned within a lumen for conducting blood of the patient. The vascular graft may be expanded from an insertion state to a deployed state. At least one of the suture cuffs may be formed as a result of the expansion, wherein each suture cuff may have additional material relative to the proximal and distal ends. A first suture cuff of the vascular graft may be secured to a wall of the lumen for conducting blood of the patient by suturing with suture material.

In one aspect, the method may also involve positioning an opposing end of the vascular graft within another lumen for conducting blood of the patient and securing a second suture cuff of the vascular graft to a wall of the another lumen for conducting blood of the patient by suturing with suture material.

BRIEF DESCRIPTION OF THE DRAWINGS

FIG. 34 is a side view of a containment sheath in a flattened configuration.

FIG. 35 is a cutaway side view of the containment sheath of FIG. 34 placed about a vascular graft in a compressed state.

FIG. 36 is a cutaway side view of the containment sheath of FIG. 35 compressing the vascular graft to the compressed state.

FIG. 37 is a cutaway perspective view of the containment sheath of FIG. 36 compressing the vascular graft to the compressed state, showing a pull wire holding the containment sheath in a compressed state.

FIG. 38 is a cutaway side view of the containment sheath of FIG. 37 allowing the vascular graft to self-expand as the pull wire is withdrawn.

FIG. 51 is a perspective view of an exemplary deployment tool that includes a sheath deployment slider actuator, usable with a hybrid graft, in an initial configuration.

FIG. 52 is a perspective view of the deployment tool of FIG. 51, in a second configuration.

FIG. 53 is a perspective view of the deployment tool of FIG. 52 with the hybrid graft removed to show the structure of the deployment tool.

FIG. 55 is a perspective view of another exemplary embodiment of deployment tool in a first configuration.

FIG. 56 is a perspective view of the deployment tool of FIG. 55 in a second configuration.

FIG. 57 is a perspective view of the deployment tool of FIG. 55 in a third configuration.

The use of the same reference symbols in different figures indicates similar or identical items.

DETAILED DESCRIPTION

Vascular Graft

Figure 1:
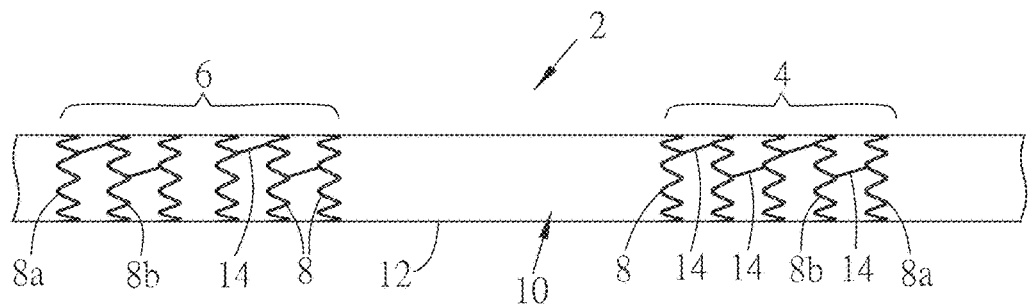
FIG. 1 is a side view of an exemplary vascular graft.

Referring to FIG. 1, a vascular graft 2 is shown. The vascular graft 2 includes a first graft anchor 4 at one end, and a second graft anchor 6 at the other end. The first graft anchor 4 is spaced apart longitudinally from the second graft anchor 6. A cover 10 extends along substantially the entire length of the vascular graft 2, covering substantially all of the outer surface of the first graft anchor 4 and second graft anchor 6. Alternately, at least part of the first graft anchor 4 and/or second graft anchor 6, such as an end of a graft anchor 4, 6, may not be covered by the cover 10. Alternately, more than one cover 10 is used, such that the cover 10 may have multiple layers, or may include two or more overlapping segments along the length of the vascular graft 2. The cover 10 may be fabricated from any suitable material or materials, such as but not limited to polytetrafluoroethylene (PTFE).

Between the two graft anchors 4, 6, a center segment 12 may include the cover 10 unsupported by internal structure. In this way, the distance between the graft anchors 4, 6 may be varied during insertion and also in use, in order to accommodate different vascular anatomies. The distance between the graft anchors 4, 6 is adjustable, rather than fixed. In other embodiments, the center segment 12 may be supported by structure that does not interfere with the ability to adjust the distance between the graft anchors 4, 6 during insertion and deployment.

The first graft anchor 4 and the second graft anchor 6 are expandable from a first insertion diameter to a second deployed diameter. The length of each graft anchor 4, 6 does not change substantially during its expansion to a deployed configuration. Alternately, at least one graft anchor 4, 6 may change in length during its expansion to a deployed configuration. The graft anchors 4, 6 may have any structure that allows for expansion from a first insertion diameter to a second deployed diameter and that holds the graft anchor 4, 6, securely inside a blood vessel in the deployed state. As one example, each graft anchor 4, 6, may include a plurality of hoops 8 extending circumferentially around the vascular graft 2. The hoops 8 may be longitudinally spaced apart; if so, adjacent hoops 8 may be connected by one or more tie bars 14. Alternately, the spaced-apart hoops 8 are not interconnected other than by the cover 10. Alternately, at least two adjacent hoops 8 are not spaced apart, but instead abut or overlap one another. In such a configuration, such adjacent hoops 8 may be fixed to one another, such as by laser welding. The hoops 8 may be fabricated from metal or other material. Each hoop 8 may have a complex shape in which the hoop 8 is fabricated from a wire, or laser cut from a tube, or otherwise manufactured such that the hoop 8 has a complex shape, such as a zig-zag, repeating Z shape, tortuous curve, or other shape. Such a shape allows the hoop 8 to expand from an insertion diameter to a deployed diameter. The zig-zag pattern of at least one hoop 8 may be continuously curved, or may include straight segments connected by curved segments. In one embodiment, the zig-zag pattern of the hoops 8 may be as set forth in expired U.S. Pat. No. 4,580,568, which is incorporated herein by reference in its entirety. However, at least one hoop 8 may be configured differently.

In one embodiment, different hoops 8 may be fabricated from different materials. For example, at least one hoop 8 may be fabricated from superelastic material, such as nickel-titanium alloy, and at least one other hoop 8 may be fabricated from plastically-deformable material, such as 316L stainless steel. Adjacent hoops 8 may alternate between different materials, such that no hoop 8 is adjacent to a hoop composed of the same material. In other embodiments, several hoops 8 composed of the same material may be grouped together, and at least one hoop 8 composed of a different material may be adjacent to that group. For example, a hoop 8 at an outer end of a graft anchor 4, 6 may be composed of stainless steel, and the remaining hoops 8 may be composed of superelastic material such as nickel-titanium alloy. By using hoops 8 fabricated from different materials, the vascular graft 2 takes advantage of the different properties of those different materials. For example, one or more hoops 8 fabricated from superelastic material are useful in expanding the graft anchor 4, 6; an outward force applied by a standard interventional balloon catheter inside such superelastic hoops 8 urges such hoops 8 between a martensite and an austenite phase, causing those hoops 8 to self-expand to a larger-diameter configuration. One or more additional hoops 8 fabricated from a plastically-deformable material such as 316L stainless steel are useful for maintaining the lumen of each anchor 4, 6 open, because such material has greater resistance to hoop stress and is not susceptible to a return to a different crystal phase after expansion. Although the term "hoop" is used in this document, the hoops 8 need not be perfectly circular as viewed on end and may have a different shape and curvature as suitable for a particular application. In some embodiments, the hoops 8 are substantially circular as viewed on end.

In one embodiment, the graft anchors 4, 6 each expand to the same or similar diameters in the deployed state. In other embodiments, the first graft anchor 4 expands to a different diameter in the deployed state than the second graft anchor 6. Similarly, in some embodiments the first graft anchor 4 has a different diameter in the insertion state than the second graft anchor 6. In this way, deployment of the vascular graft 2 may be facilitated, and/or a better fit of the vascular graft 2 in specific vascular tissue of a patient may be facilitated. The difference in diameter between the first graft anchor 4 and the second graft anchor 6 may be controlled by controlling the diameter of the hoops 8 in the first graft anchor 4 to be different than the diameter of the hoops 8 in the second graft anchor 6, by providing a different mix of hoops 8 with different materials in different graft anchors 4, 6, or in any other suitable manner.

Operation—Vascular Graft

Figure 2:
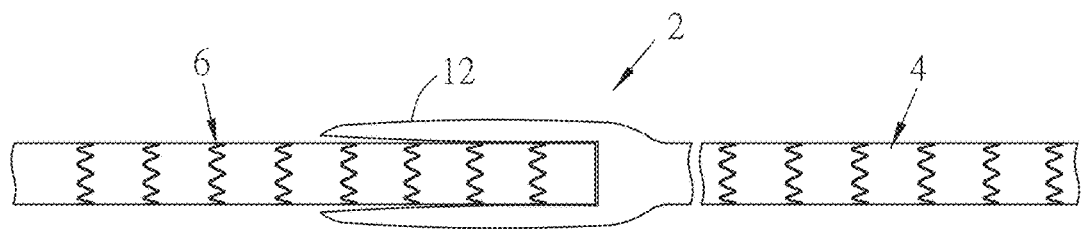
FIG. 2 is a side view of the exemplary vascular graft of FIG. 1 in an insertion configuration.

Referring to FIG. 2, the vascular graft 2 is in an insertion configuration for introduction into the patient's vasculature. The second graft anchor 6 is moved toward the first graft anchor 4, and the center segment 12 everts over the second graft anchor 6. The graft anchors 4, 6 optionally may come close to abutting in the insertion configuration and are separated by the thickness of the cover 10.

The vascular graft 2 in the insertion configuration is inserted into the vasculature in any suitable manner, such as via a standard femoral incision. During insertion, the vascular graft 2 may be held within the lumen of a catheter, and a guidewire may extend through the lumen of the vascular graft. The vascular graft 2 is advanced through the vasculature to the treatment site using a guidewire and catheter in a standard manner, or advanced through the vasculature in any other suitable manner.

Figure 3:
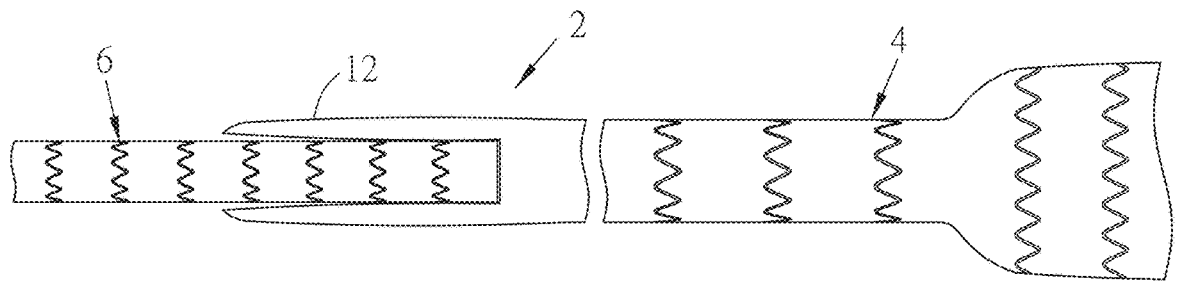
FIG. 3 is a side view of the exemplary vascular graft of FIG. 1 after a first deployment step.

Referring to FIG. 3, when the vascular graft 2 reaches the treatment site, a standard interventional balloon is expanded within the first graft anchor 4. The expansion of the balloon causes the hoops 8 of the first graft anchor 4 to expand to a larger-diameter configuration. Where at least one of the hoops 8 is composed of a superelastic material, expansion of the balloon urges such at least one hoop 8 between a martensite and an austenite phase, causing such at least one hoop 8 to self-expand to a larger-diameter configuration.

Figure 4:
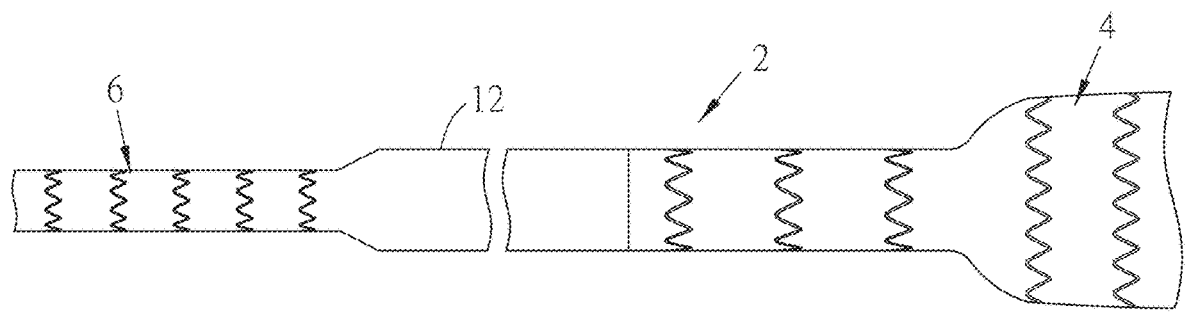
FIG. 4 is a side view of the exemplary vascular graft of FIG. 1 after a second deployment step.
Figure 5:
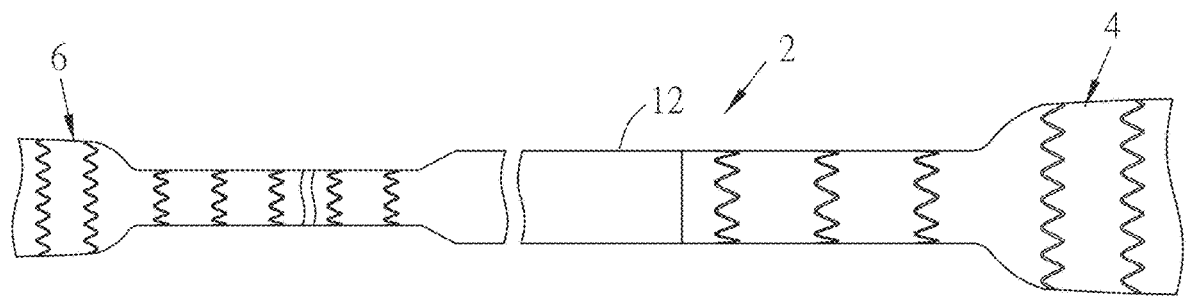
FIG. 5 is a side view of the exemplary vascular graft of FIG. 1 after a third deployment step.

Referring to FIG. 4, after expansion of the first graft anchor 4 to its deployed diameter, the second graft anchor 6 is pulled proximally away from the first graft anchor 4 to its desired location of deployment. The flexibility of the center segment 12 allows this adjustment of the distance between the graft anchors 4, 6. As seen in FIG. 4, the diameter of the center segment 12 may be smaller than the diameter of the first graft anchor 4. Finally, referring to FIG. 5, a standard interventional balloon is expanded within the second graft anchor 6, which expands in the same manner described above with regard to the first graft anchor 4. As set forth above, the expanded diameter of the first graft anchor 4 may be substantially the same as, or different from, the expanded diameter of the second graft anchor 6. The interventional balloon, guidewire, catheter, and/or other interventional devices are withdrawn from the treatment site, and the vascular graft 2 remains in its deployed state and deployed position.

Aortic Graft

Figure 6:
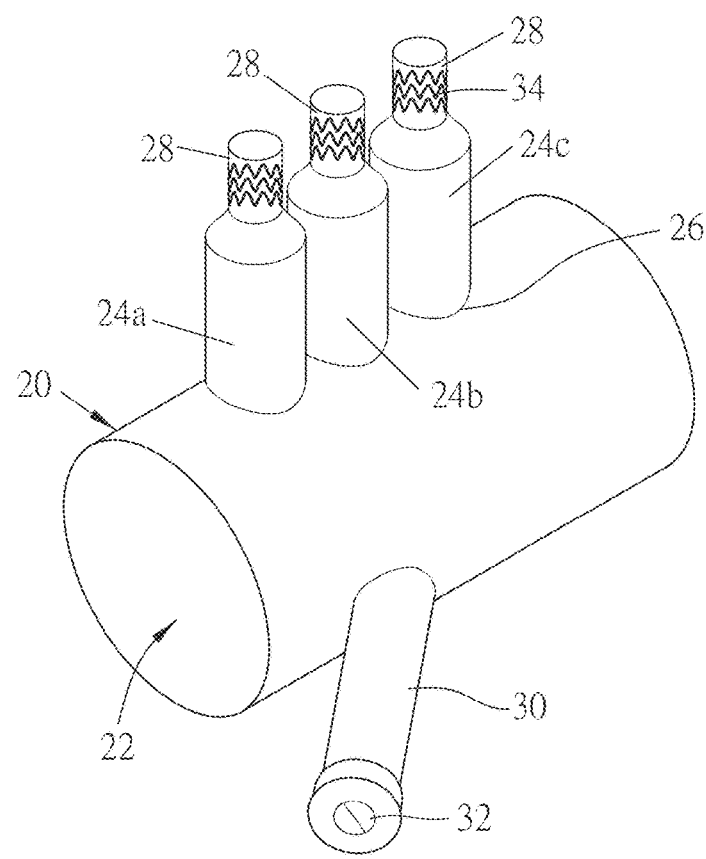
FIG. 6 is a perspective view of an exemplary center section of an aortic graft.
Figure 7:
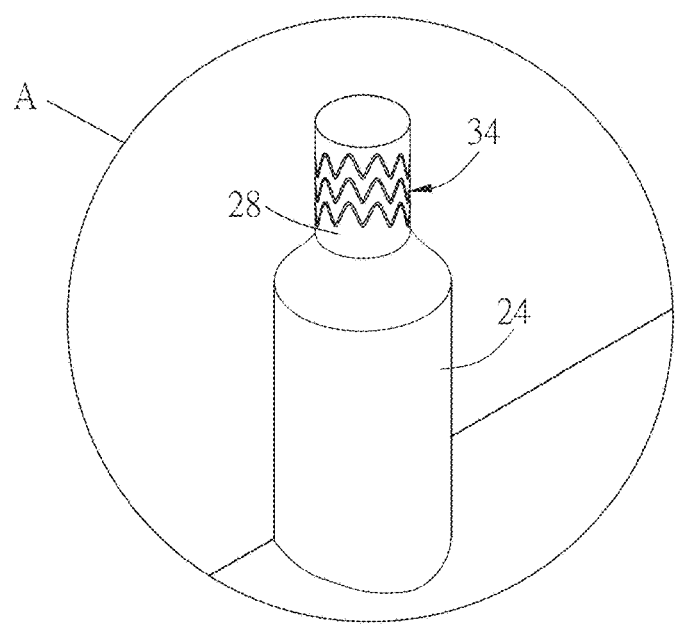
FIG. 7 is a detail view of a jumper graft shown in FIG. 6.
Figure 12:
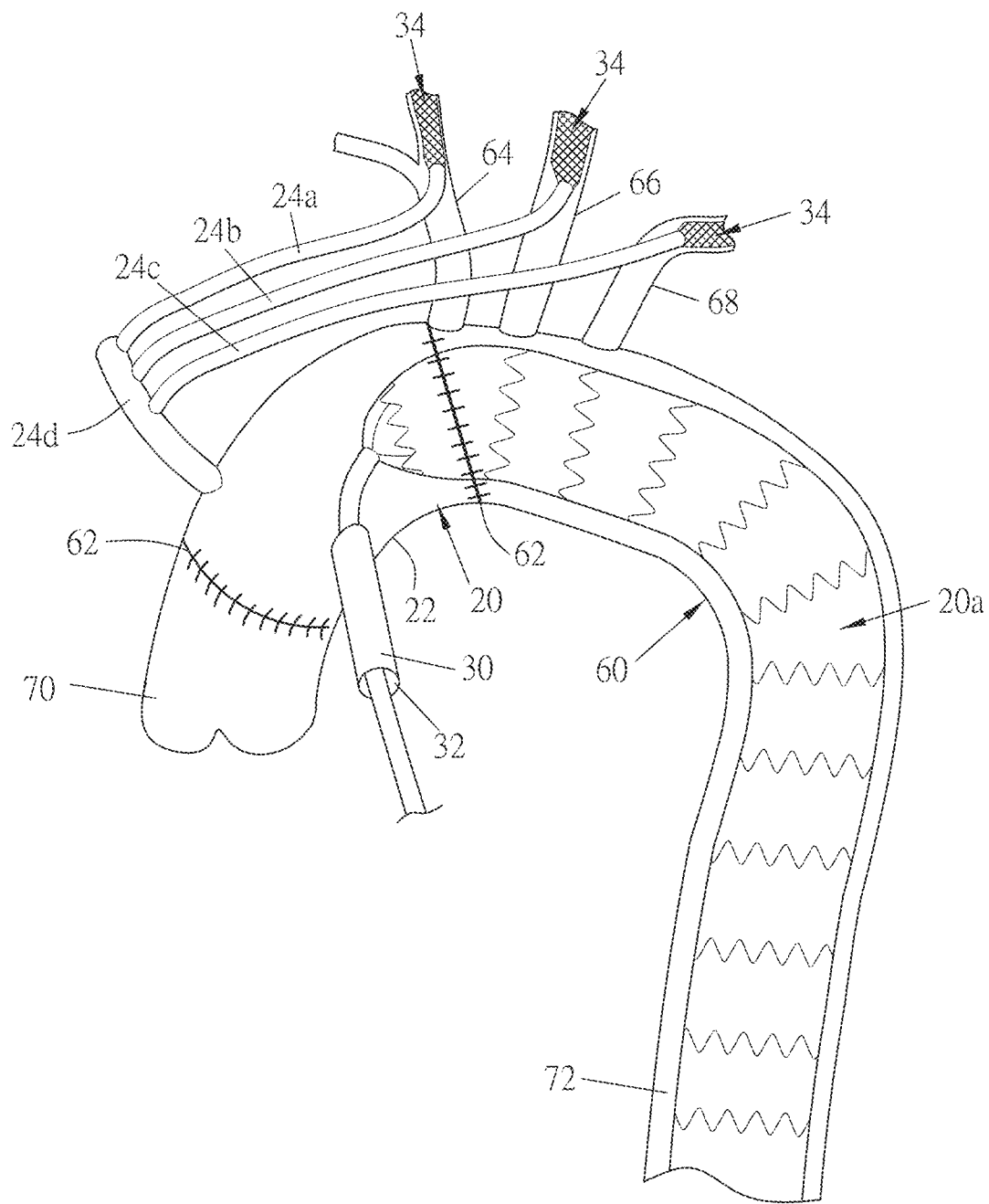
FIG. 12 is a side view of a first exemplary implantation of an embodiment of an exemplary center section of an aortic graft.
Figure 14:
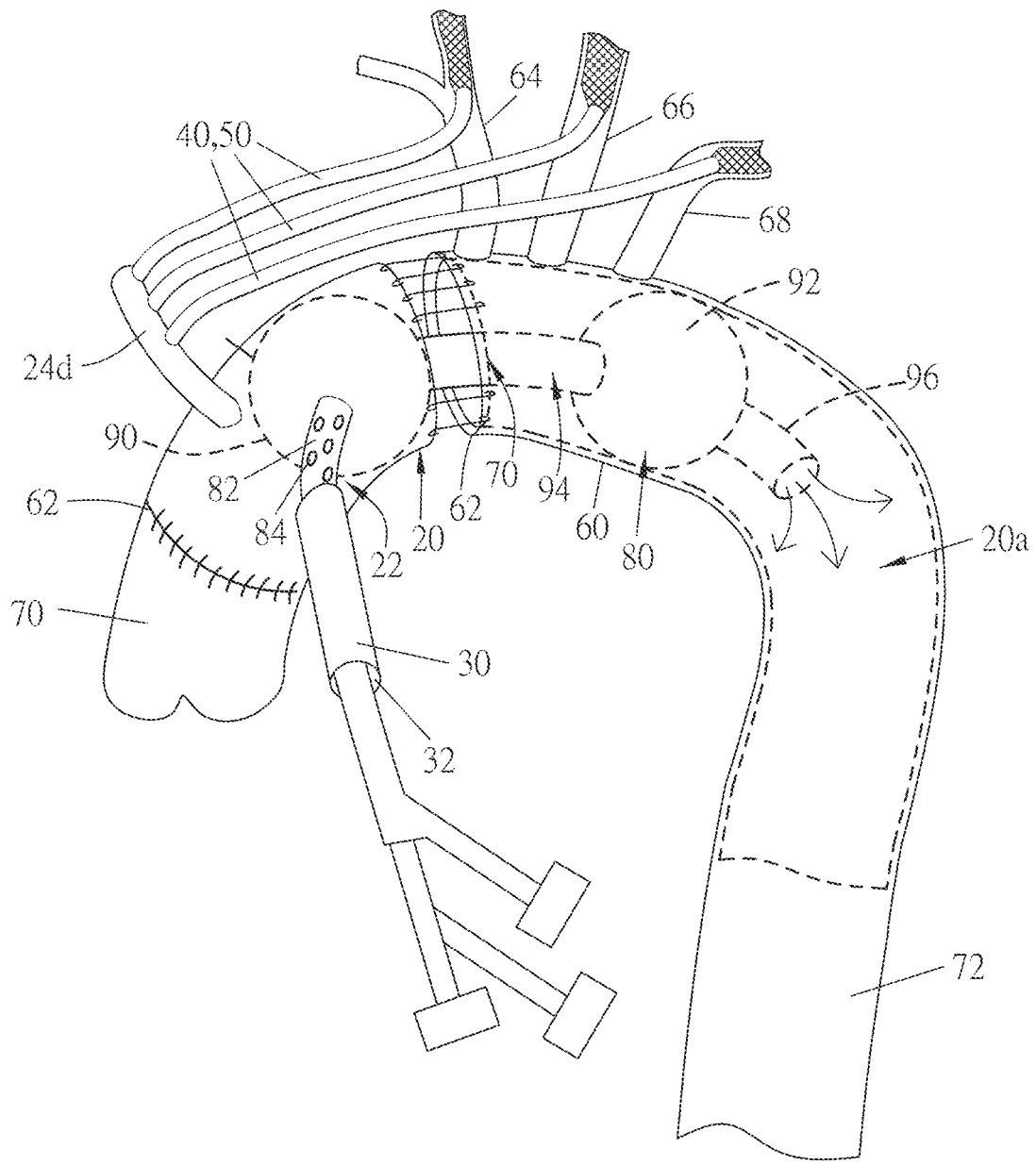
FIG. 14 is a side view of a second exemplary implantation of an embodiment of an exemplary center section of an aortic graft.

Referring to FIGS. 6-7, a central section 22 of an aortic graft 20 is shown. Referring also to FIGS. 12 and 14, an entire aortic graft 20 is shown, and is described in greater detail below. The central section 22 of the aortic graft 20 reinforces or replaces the aortic arch during surgery. The aortic graft 20, including the central section 22, typically is fabricated from a polyester such as polyethylene terephthalate (PET), sometimes known as DACRON® brand polyester available from E. I. Du Pont De Nemours and Company of Wilmington, Delaware. Advantageously, the aortic graft 20, including the central section 22, is impregnated with collagen, which encourages the patient's own tissue to grow into the aortic graft 20. Alternately, if desired, the aortic graft 20 may be fabricated from any other biocompatible material that is strong, flexible and leakproof.

The central section 22 of the aortic graft 20 may include three jumper grafts 24a, 24b, 24c. The three jumper grafts 24a, 24b, 24c correspond to the three arteries that arise from the aortic arch: the brachiocephalic trunk, left common carotid artery, and left subclavian artery. The three jumper grafts 24a, 24b, 24c each include an inner lumen that allows blood to flow therethrough, originating from the central section 22 of the aortic graft 20. The base 26 of each jumper graft 24a, 24b, 24c advantageously is fixed to the central section 22 of the aortic graft 20. In some embodiments, at least one jumper graft 24a, 24b, 24c is fabricated from PTFE and attached to the central section 22 of the aortic graft 20. In other embodiments, at least one jumper graft 24a, 24b, 24c is integral with the aortic graft 20 and is also fabricated from the same material as the central section 22 of the aortic graft 20. The tip 28 of each jumper graft 24a, 24b, 24c may include an expandable mesh 34 that is generally tubular and that has a lumen defined therethrough. In some embodiments, the expandable mesh 34 has substantially the same diameter along its entire length. In other embodiments, the proximal end of the expandable mesh 34 (the end closer to the central section 22 of the aortic graft 20) may be flared outward. In some embodiments, the proximal end of at least one expandable mesh 34 may be sewn or otherwise fixed to the tip of the corresponding jumper graft 24a, 24b, 24c. In some embodiments, at least one expandable mesh 34 may be fabricated in the same or similar manner as at least one graft anchor 4, 6, and scaled down to a smaller length and diameter. The expandable mesh 34 advantageously is self-expanding; for example, the expandable mesh 34 may be fabricated from superelastic material such as nitinol; as another example, the expandable mesh 34 may be fabricated from plastically deformable material, such as stainless steel, that is compressed to an amount below its elastic limit, and then that compression is removed to allow the expandable mesh 34 to self-expand into place.

The central section 22 of the aortic graft 20 advantageously also includes an access port 30. The access port 30 includes an inner lumen that allows instruments and/or guidewires to be inserted therethrough into and withdrawn therethrough out of the central section 22 of the aortic graft 20. In some embodiments, the access port 30 is fabricated from PTFE and attached to the central section 22 of the aortic graft 20. In this way, the access port 30 easily can be sealed and/or removed after implantation of the aortic graft 20 is complete. In other embodiments, the access port 30 is integral with the aortic graft 20 and is also fabricated from the same material as the central section 22 of the aortic graft 20. One end of the access port 30 connects to the central section 22 of the aortic graft 20; the other end of the access port 30 includes a hemostasis valve 32 that allows instruments and/or guidewires to enter and exit the access port 30 while blood is flowing through the central section 22 of the aortic graft 20.

Figure 6A:
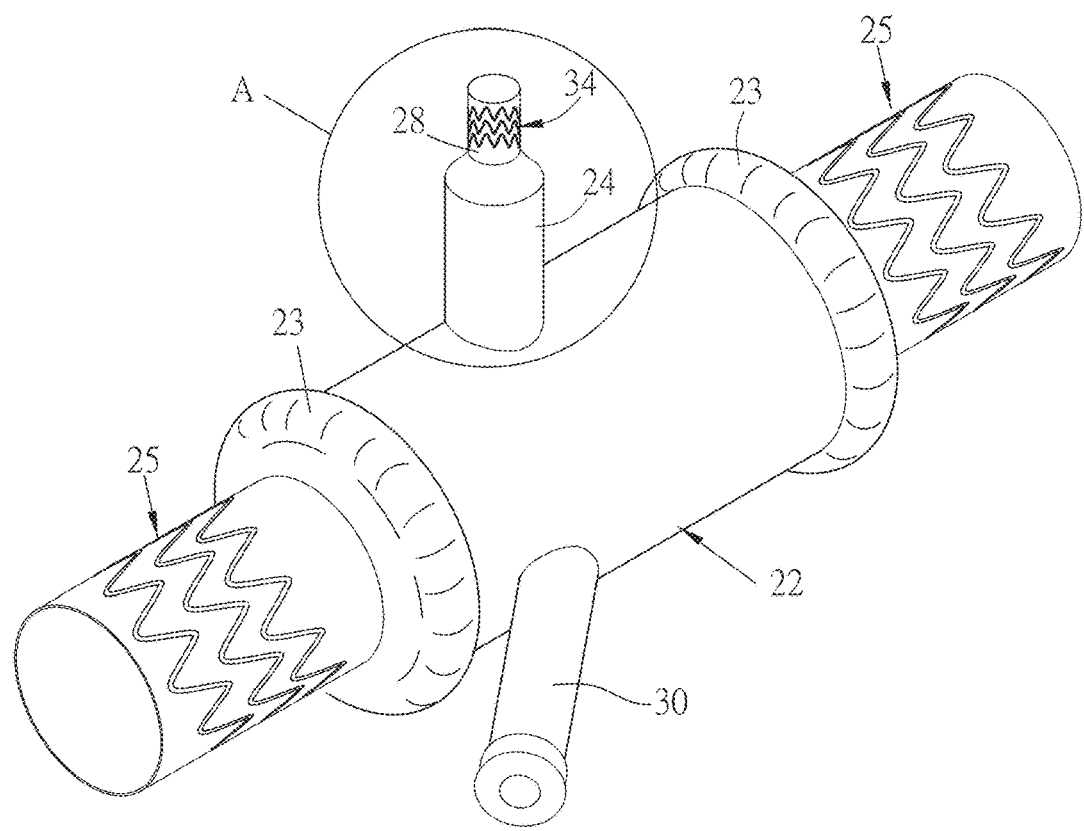
FIG. 6A is a perspective view of a second exemplary center section of an aortic graft.

Referring also to FIG. 6A, another exemplary embodiment of the central section 22 of the aortic graft 20 is shown. In the exemplary embodiment of FIG. 6A, a suture band or ring 23 is provided at or in proximity to one or both ends of the central section 22. Each suture band 23 may be a thicker section of the wall of the central section 22 or may be a separate item that is fixed to the central section 22, such as a metallic or nonmetallic mesh. As described in greater detail below, each suture band 23 provides an area on the central section 22 that can be sutured to the aorta or other tissue, with even greater suitability for engaging suture and holding the central section 22 in place upon implantation. In other embodiments, additional suture rings 23 may be provided, or larger suture regions 23 may be provided on the central section 22. In addition to the suture ring or rings 23, optionally one or more central section anchors 25 may be attached to the central section 22. Each central section anchor 25 may be self-expanding; for example, at least one central section anchor 25 may be fabricated from superelastic material such as nitinol; as another example, at least one central section anchor 25 may be fabricated from plastically deformable material, such as stainless steel, that is compressed to an amount below its elastic limit, and then that compression is removed to allow the central section anchor 25 to self-expand into place. Each central section anchor 25 may be affixed to the central section 22 in any suitable manner, such as by molding, adhesive, or wire. Optionally, at least one central section anchor 25 may be fixed to a corresponding suture band 23, and affixation between the suture band 23 and the central section 22 in turn affixes that central section anchor 25 to the central section 22. Alternately, the central section anchors 25 may be attached to the central section 22, and one or more suture rings 23 may be omitted.

Figure 8:
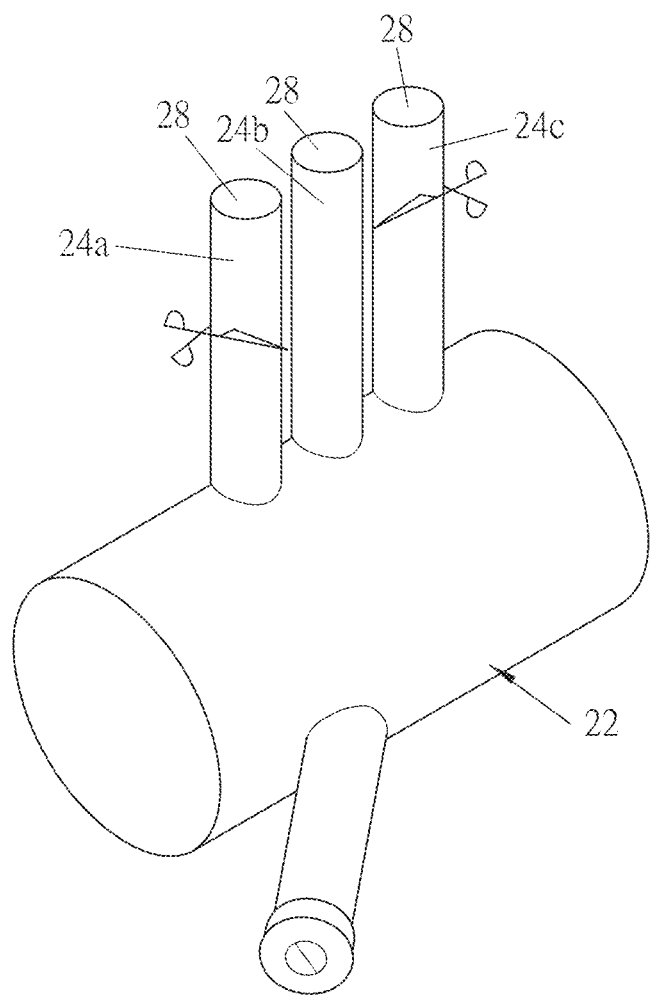
FIG. 8 is a perspective view of a third exemplary center section of an aortic graft.

Referring also to FIG. 8, another exemplary embodiment of the central section 22 of the aortic graft 20 is shown. In the exemplary embodiment of FIG. 8, the jumper grafts 24a, 24b, 24c are fabricated from PTFE or similar material, and are longer than those of the exemplary embodiment of FIG. 7. Because these jumper grafts 24a, 24b, 24c are longer than those of the embodiment of FIG. 7, the surgeon has greater flexibility to cut or place those jumpers as needed in the body. The tip 28 of each jumper graft 24a, 24b, 24c does not include an expandable mesh 34 as described with regard to FIG. 7 above; rather, the tip of each jumper graft 24a, 24b, 24c is simply the end of a tube.

Figure 9:
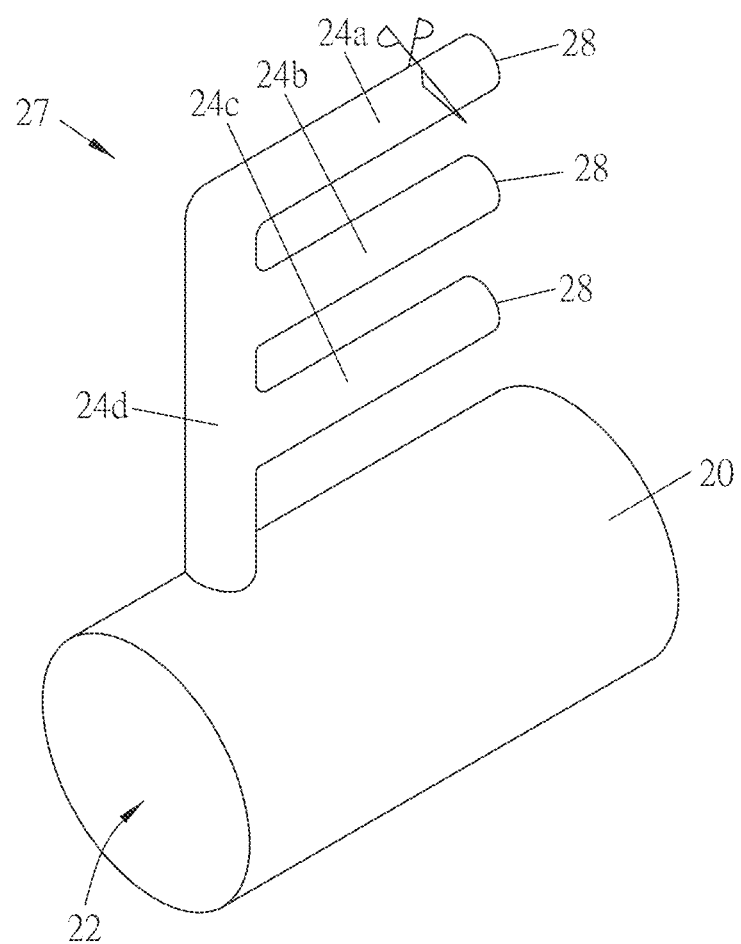
FIG. 9 is a perspective view of a fourth exemplary center section of an aortic graft.

Referring also to FIG. 9, another exemplary embodiment of the central section 22 of the aortic graft 20 is shown. In the exemplary embodiment of FIG. 9, a branched graft 27 includes a manifold 24d that extends from the central section 22 of the aortic graft 20. The manifold 24d may be fixed to the central section 22 or may be connected to a jumper graft 24 that is fixed to the central section 22 in a similar manner as described above. Jumper grafts 24a, 24b, 24c extend from the manifold 24d, and are in fluid communication with the manifold 24d and the lumen of the central section 22. This configuration may provide additional versatility with respect to certain anatomies. In the exemplary embodiment of FIG. 9, the jumper grafts 24a, 24b, 24c otherwise may be configured as describe with regard to FIG. 7 or FIG. 8, and may include or exclude the expandable mesh 34 at the tip 28 of at least one jumper graft 24a, 24b, 24c. It will be apparent that features described in different embodiments of the central section 22 may be combined as desired in an aortic graft 20. It is also noted that jumper grafts 24 and vascular grafts 2 may be used interchangeably at the discretion of the clinician, and that the phrases "jumper graft" and "vascular graft" may be used interchangeably in this document.

Figure 9A:
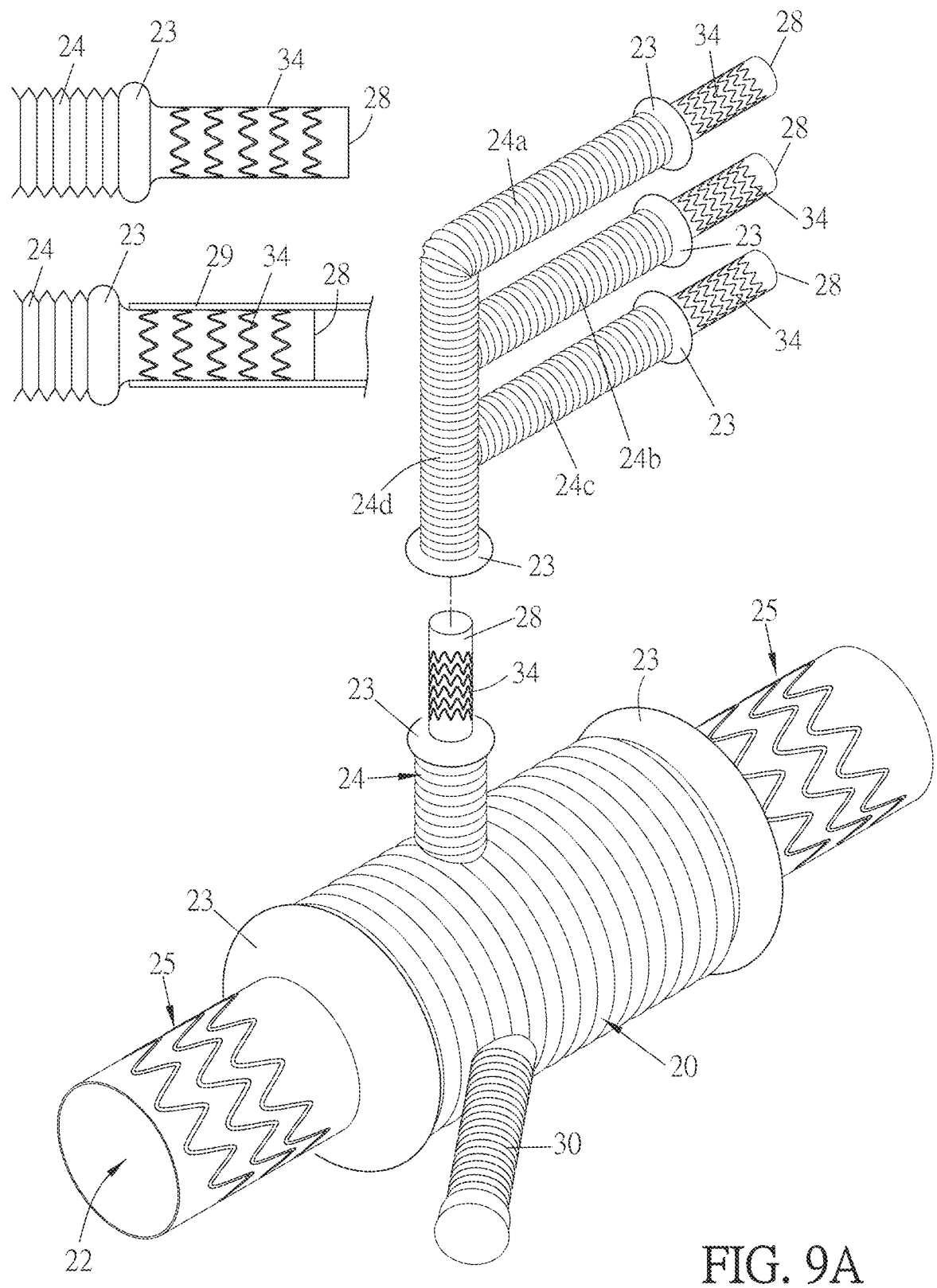
FIG. 9A is a perspective view of a fifth exemplary center section of an aortic graft.

Referring also to FIG. 9A, another exemplary embodiment of the central section 22 of the aortic graft 20 is shown. The central section 22 is generally as described above with regard to FIG. 6A. The central section 22 may be corrugated and fabricated from generally kink-proof material. The corrugation optionally allows the central section 22 to be lengthened or shortened as desired by the clinician upon implantation of the central section 22. The central section includes a single jumper graft 24 extending therefrom, which also may be corrugated and fabricated from generally kink-proof material. The corrugation optionally allows the jumper graft 24 to be lengthened or shortened as desired by the clinician. A suture band 23 as described above with regard to FIG. 6A may be located proximal to the mesh structure 34, between the mesh structure 34 and a remainder of the jumper graft 24.

The branched graft 27 includes a manifold 24d and jumper grafts 24a, 24b 24c extending therefrom, as described with regard to FIG. 9. At least one of the manifold 24d and jumper grafts 24a, 24b, 24c may be corrugated and fabricated from generally kink-proof material. The corrugation optionally allows the manifold 24d and/or at least one jumper graft 24a, 24b, 24c to be lengthened or shortened as desired by the clinician upon implantation of the manifold 24d and jumper grafts 24a, 24b, 24c. A suture band 23 as described above with regard to FIG. 6A may be located at the free end of the manifold 24d, corresponding to the suture band 23 of the jumper graft 24. When the manifold 24d is attached to the jumper graft 24, the suture band 23 of the manifold 24d and jumper graft 24 may be sutured together in order to connect them, or in order to reinforce the connection between the two that is made by expansion of the expanding mesh 34. Similarly, a suture band 23 may be located in proximity to the tip 28 of at least one of the jumper grafts 24a, 24b, 24c. Each suture band 23 may be as described above with regard to FIG. 6A and may be located proximal to the mesh structure 34, between the mesh structure 34 and a remainder of the jumper graft 24a, 24b, 24c. The suture band 23 facilitates suturing the end of the jumper graft 24a, 24b, 24c to a vessel 29, providing a strong and accessible location for suturing. That suturing may be used to reinforce the connection to the jumper graft 24a, 24b, 24c made by the expansion of the expandable mesh 34 within the vessel 29. Further, if an additional jumper 40, 50 as described below is attached to the tip 28 of a jumper graft 24a, 24b, 24c for additional length, the proximal end of that jumper 40, 50 may be sutured to the suture band 23 at the end of the jumper graft 24a, 24b, 24c to reinforce the connection to the jumper graft 24a, 24b, 24c made by the expansion of the expandable mesh 34 within the additional jumper 40, 50.

Figure 31:
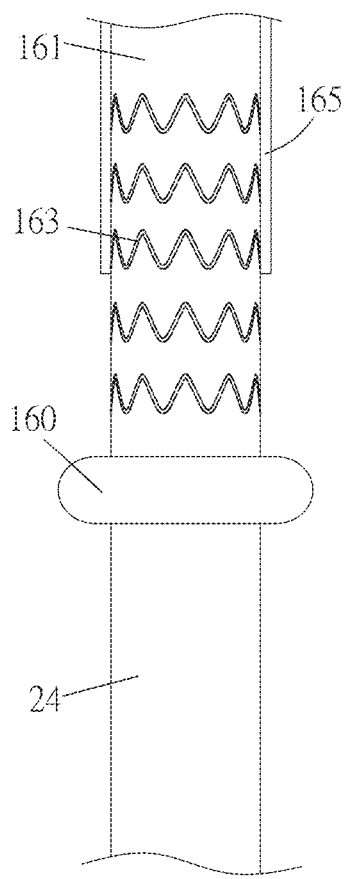
FIG. 31 is a side vide of a vascular graft with a suture cuff in a first state.
Figure 32:
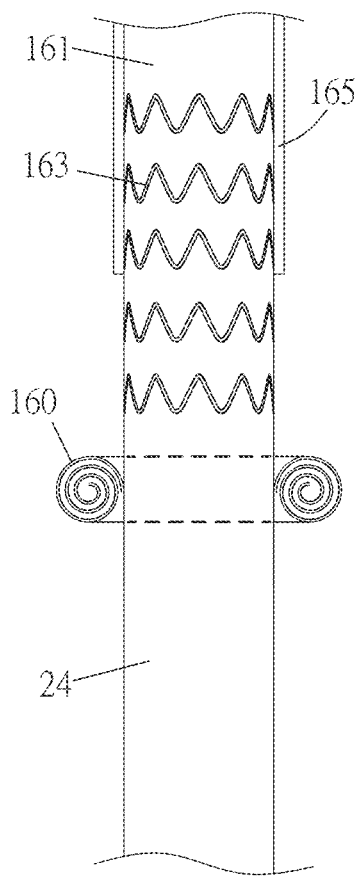
FIG. 32 is a side vide of the vascular graft of FIG. 31 with a suture cuff in a first state, with the suture cuff in proximity to a vessel wall.
Figure 33:
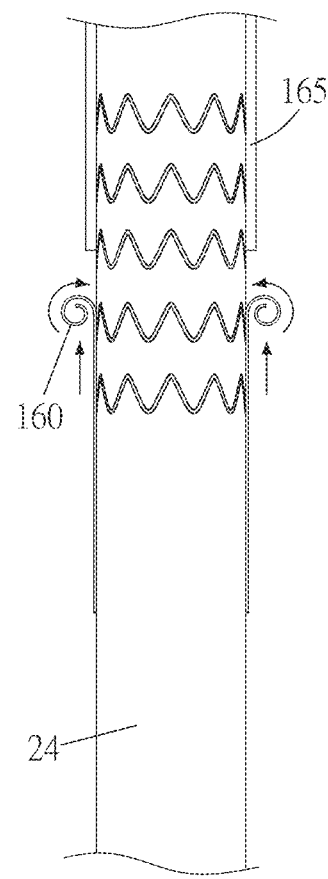
FIG. 33 is a side vide of the vascular graft of FIG. 32 with a suture cuff in a second state relative to the vessel wall.

Referring also to FIGS. 31-33, according to some embodiments, an end of at least one jumper graft 24a, 24b, 24c may include a suture cuff 160. The suture cuff 160 is a segment of material that is in a configuration that initially is rolled up like the cuff of a sock. The suture cuff 160 may be integral with an outer covering of the jumper graft 24 and may be longer than the jumper graft 24 in a fully unrolled configuration and may be coterminous in length with the jumper graft 24a, 24b, 24c initially. Alternately, the suture cuff 160 may be a separate piece of material that is sewn to or otherwise affixed to an end of a jumper graft 24. As described in greater detail below, the suture cuff 160 may be unrolled from the end of a jumper graft 24 symmetrically or asymmetrically in order to meet the wall of the vessel to which the jumper graft 24 is connected, and also to provide a ring of material that a surgeon can utilized to suture the jumper graft 24 to that vessel wall in order to provide a more secure connection to the vessel wall. The jumper graft 24 may include an outer cover 161 about a cylindrical scaffold 163. The outer cover 161 may be fabricated from any suitable biocompatible material, such as but not limited to polytetrafluoroethylene (PTFE) or a polyester such as polyethylene terephthalate (PET), sometimes known as DACRON® brand polyester available from E. I. Du Pont De Nemours and Company of Wilmington, Delaware. The scaffold 163 may be fabricated from nickel-titanium alloy, spring steel, or any other suitable biocompatible material. The scaffold 163 may be longitudinally shorter than the outer cover 161, and the section of the outer cover 161 extending longitudinally outward from an end of the scaffold 163 may form the suture cuff 160. That is, the excess length of the outer cover 161 relative to the scaffold 163 initially may be rolled into a ring about the longitudinal centerline of the scaffold 163 at one end of the scaffold 163. While the suture cuff 160 is described here in the context of its usage with a jumper graft 24, the suture cuff 160 may be used with any other jumper, graft or anchor described in this document, as appropriate.

Referring also to FIGS. 34-38, a containment sheath 180 may be utilized in order to hold at least one jumper graft 24 in a constrained initial configuration prior to deployment. The containment sheath 180 may be fabricated from any suitable biocompatible material, such as but not limited to polytetrafluoroethylene (PTFE) or a polyester such as polyethylene terephthalate (PET), sometimes known as DACRON® brand polyester available from E. I. Du Pont De Nemours and Company of Wilmington, Delaware. As described in greater detail below, advantageously the containment sheath 180 is not left in the body. Referring to FIG. 34, the containment sheath 180 is shown in a flattened configuration prior to assembly. The lateral edges 182 of the containment sheath 180 are curved in a sinusoidal or generally-sinusoidal pattern, and are offset from one another such that peaks 184 on one lateral edge 182a of the containment sheath 180 match valleys 186 on the other lateral edge 182b of the containment sheath 180 when the containment sheath 180 is rolled about a jumper graft 24. Laterally in proximity to each peak 184 is a hole 188. Alternately, the holes 188 are located in proximity to some pairs of peaks 184, where the pairs of peaks 184 are defined as two peaks 184 longitudinally closest to one another although laterally spaced apart.

Referring also to FIG. 35, the containment sheath 180 is rolled about a jumper graft 24 in an initial, compressed configuration, and compresses the jumper graft 24 to an insertion diameter. Referring also to FIGS. 36-37, a pull wire 190 passes through longitudinally-adjacent holes 188 in the rolled containment sheath 180. In this way, the pull wire 190 holds the adjacent edges 182a, 182b of the containment sheath 180 together. The proximal end 192 of the pull wire 190 may extend proximally along a deployment tool 200. As described in greater detail below, the pull wire 190 may be retracted in the proximal direction out of the holes 188 in order to open the containment sheath 180 and allow the jumper graft 24 to expand. The pull wire 190 may be fabricated from any suitable material, such as a stainless steel wire. Alternately, the pull wire 190 may be fabricated from a biocompatible non-metallic material such as nylon or biocompatible fabric. While the containment sheath 180 is described here in the context of its usage with a jumper graft 24, the containment sheath 180 may be used with any other jumper, graft or anchor described in this document, as appropriate.

Figure 27:
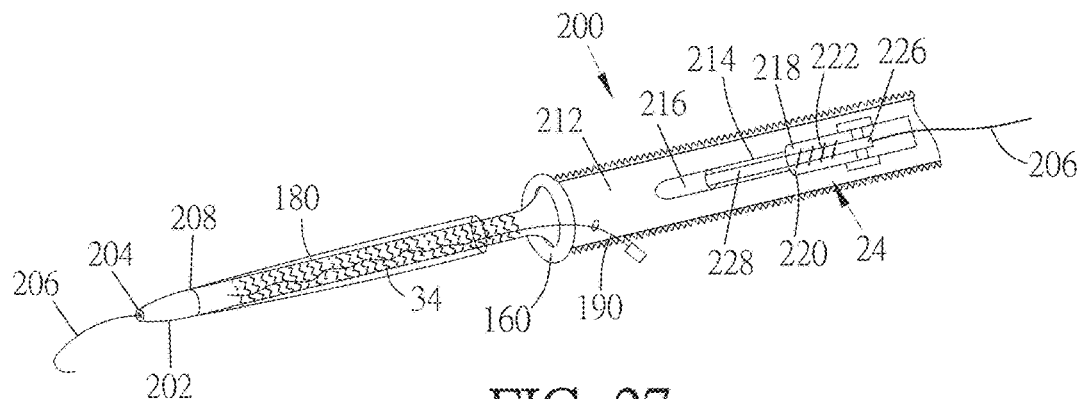
FIG. 27 is a partial cutaway perspective view of a deployment tool in a first state.
Figure 28:
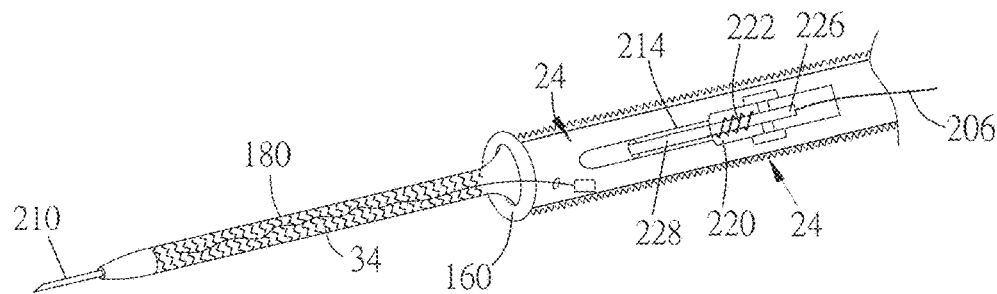
FIG. 28 is a partial cutaway perspective view of the deployment tool of FIG. 27 in a second state.
Figure 29:
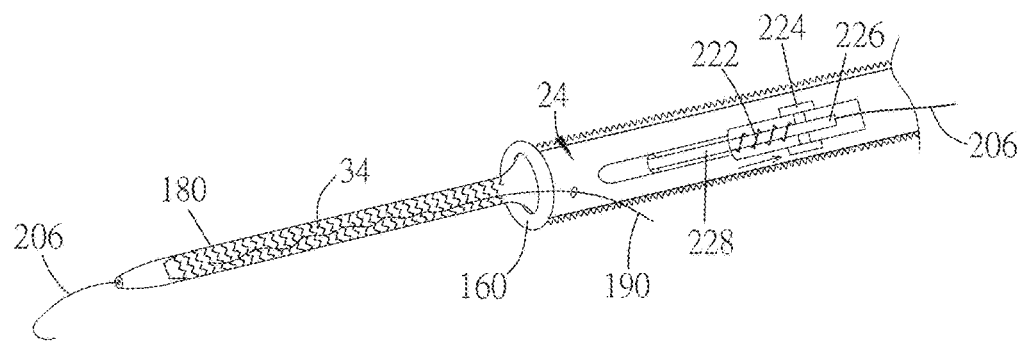
FIG. 29 is a partial cutaway perspective view of the deployment tool of FIG. 27 in a third state.
Figure 30:
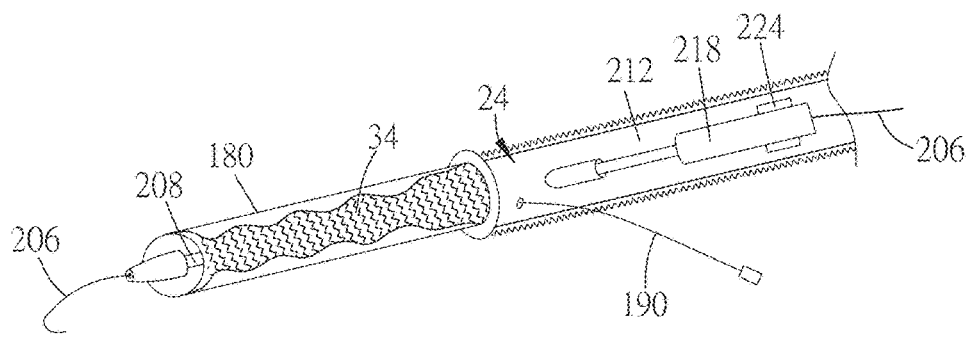
FIG. 30 is a partial cutaway perspective view of the deployment tool of FIG. 27 in a fourth state.

Referring also to FIG. 27, an exemplary deployment tool 200 is shown. At the distal end of the deployment tool 200, is a blunt dilator tip 202. The dilator tip 202 is sized and shaped to dilate an incision or opening made in a vessel, as described in greater detail below. A passage 204 is defined through the dilator tip 202. Advantageously, the passage 204 is straight and substantially coaxial with the longitudinal centerline of the deployment tool 200. Alternately, the passage 204 may be shaped differently, and/or oriented differently relative to the deployment tool 200. A guidewire 206 may be extensible through and/or retractable into the passage 204. As seen in FIGS. 27 and 29-30, advantageously the guidewire 206 is configured to curve when the guidewire 206 exits the passage 204. That is, upon exiting the passage 204, the distal end of the guidewire 206 curves away from the longitudinal centerline of the deployment tool 200, whether to one side or back toward the proximal direction as seen in FIGS. 27 and 29-30. Alternately, the distal end of the guidewire 206 begins to curve away from the longitudinal centerline of the deployment tool 200 after the distal end of the guidewire 206 has been advanced distally such that the distal end of the guidewire 206 is spaced apart from the distal end of the dilator tip 202. Referring also to FIG. 28, a needle 210 may be located within the passage 204 through the dilator tip 202 in a neutral position. The needle 210 may be advanceable relative to the dilator tip 202 in order to puncture a vessel in the patient's body. Advantageously, the needle 210 is hollow, such that the guidewire 206 can pass through the needle 210.

Referring also to FIG. 27, proximal to the dilator tip 202, the deployment tool 200 includes a mandrel 208. A jumper graft 24 is wrapped around the mandrel 208, and is compressed at least partially against the mandrel 208 by a containment sheath 180. As described above, referring also to FIG. 36, a pull wire 190 extends through longitudinally-adjacent holes 188 and thereby holds the lateral edges 182 of the containment sheath 180 together. In this way, the jumper graft 24 is compressed against the mandrel 208 by the containment sheath 180. The jumper graft 24 is located proximal to the dilator tip 202. Alternately, the distal end of the jumper graft 24 may be positioned in proximity to the distal end of the dilator tip 202. The jumper graft 24 may include a suture cuff 160 as described above. The suture cuff 160 may be positioned at the proximal end of the jumper graft 24, relative to the deployment tool 200. Alternately, the suture cuff 160 may be positioned at the distal end of the jumper graft 24, relative to the deployment tool 200.

Referring also to FIG. 27, a handle 212 is connected to the proximal end of the mandrel 208. The mandrel 208 may be fabricated separately from the handle 212 and attached to the handle 212, or the mandrel 208 and handle 212 may be fabricated integrally. The handle 212 may be fabricated from any suitable material. As seen in the partial cross-section view of FIG. 27, a lumen 214 may extend substantially longitudinally through the handle 212, as well as the mandrel 208. The lumen 214 may have a generally circular cross-section, or may have any other suitable cross-sectional shape. A side port 216 may extend laterally through the handle 212 to the lumen 214. The pull wire 190 may extend proximally into the lumen 214 and then outward through the side port 216. A proximal section of the lumen 214 may be wider than a distal section of the lumen 214. That wider section of the lumen 214 may be referred to as the spring receiver 218. The spring receiver 218 may have a generally circular cross-section, or may have any other suitable cross-section. A ledge 220 may be located at the proximal end of the spring receiver 218, where the width of the lumen 214 widens. A compression spring 222 may be located within the spring receiver 218. The distal end of the compression spring 222 may be seated on the ledge 220, which prevents the distal end of the compression spring 222 from moving distal to the ledge 220. A needle advancement button 224 is positioned proximal to the compression spring 222. The proximal end of the needle advancement button 224 is connected to the compression spring 222 directly or indirectly, such that distal motion of the needle advancement button 224 compresses the compression spring 222. The needle advancement button 224 is affixed to or otherwise coupled to a needle deployment controller 228. The needle deployment controller 228 extends through the lumen 214 and is affixed to or otherwise coupled to the needle 210. The needle deployment controller 228 may be a generally rigid wire, or any other structure capable of bearing a compressive force and transmitting that force distally. Alternately, the needle deployment controller 228 may be selectively engageable to and disengageable from the needle 210, such as via at least one intermediate mechanism. The compression spring 222 biases the needle advancement button 224 proximally, and thereby biases the needle 210 proximally into the passage 204 in the dilator tip 202 via the needle deployment controller 228. When the needle 210 is biased into the passage 204 in the dilator tip 202, the needle 210 and the needle deployment controller 228 are in a neutral state. Depression of the needle deployment controller 228 in the distal direction advances the needle 210 distally out of the dilator tip 202, as described in greater detail below.

The needle advancement button 224 includes a lumen 226 extending generally longitudinally therethrough. In this way, the guidewire 206 may extend through the lumen 214 of the mandrel 208 and handle 212, and also the lumen 226 of the needle advancement button 224, and then out of the proximal end of the needle advancement button 224.

While the deployment tool 200 is described here in the context of its usage with a jumper graft 24, the deployment tool 200 may be used with any other jumper, graft or anchor described in this document, as appropriate.

Figure 10:
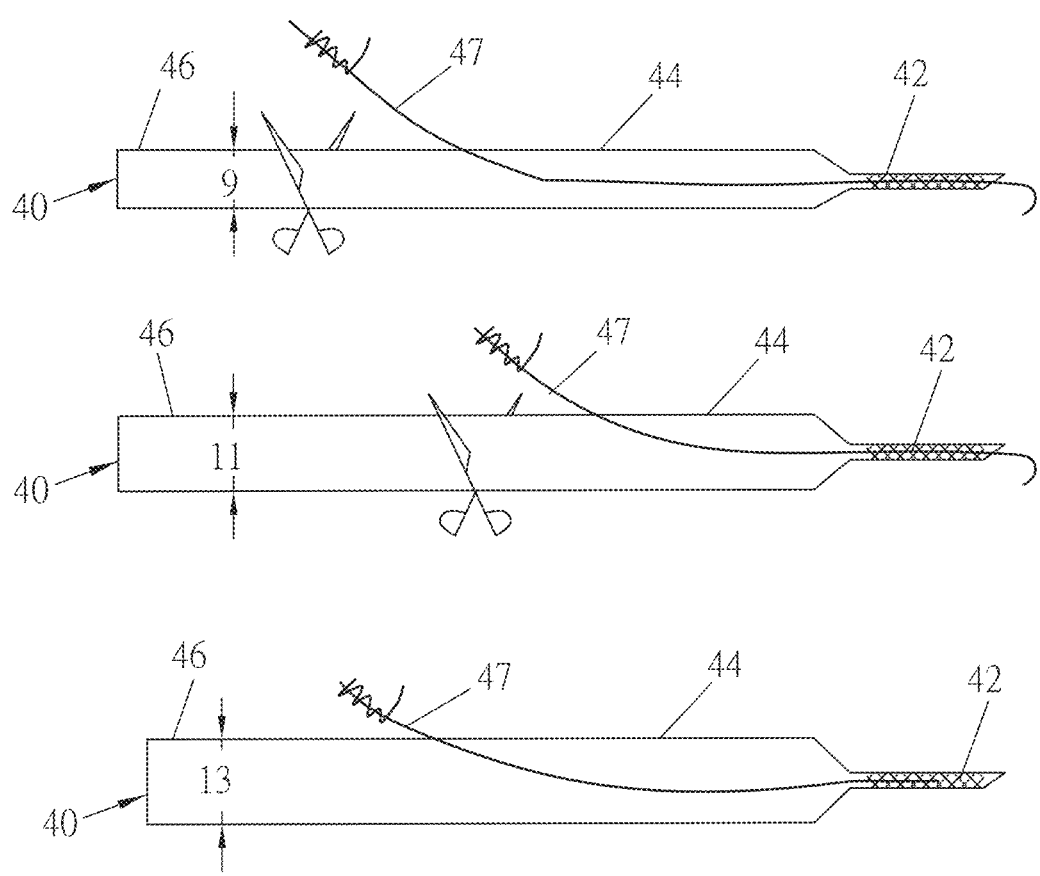
FIG. 10 is a side view of a plurality of first exemplary jumpers.

Referring also to FIG. 10, jumpers 40 with different inside diameters are shown. Jumper 40a may have an inside diameter of substantially 9 mm, jumper 40b may have an inside diameter of substantially 11 mm, and jumper 40c may have an inside diameter of substantially 13 mm. Jumpers 40 with other inside diameters may be provided. A jumper 40 may be arbitrarily long. An expanding end 42 of a jumper 40 may be configured in substantially the same manner as a graft anchor 4, 6 as described above, such that the expanding end 42 is small in diameter in an insertion state (shown in FIG. 10) and larger in diameter in an expanded state. As with the vascular graft 2 described above, the expanding end 42 of the jumper 40 may be connected to and/or covered by a cover 44, which may be fabricated from PTFE or any other suitable material. The anchored end 46 of a jumper 40 may be the end of the cover 44 that is not connected to the expanding end 42 of the jumper 40. Advantageously, no anchor or other hardware is fixed to the anchored end 46 of the jumper 40, because the jumper 40 may be cut between the anchored end 46 and the expanding end 42 in order to allow the surgeon, nurse, or other operating room professional to cut the jumper 40 to a length appropriate for the patient's anatomy in the operating room prior to implantation in the patient. The cover 44 may accommodate a guidewire 47 or cannula (not shown) through a lateral side thereof, allowing the guidewire to access the lumen of the jumper 40 other than through the opening in the anchored end 46 of the jumper 40. The guidewire 47 may simply pierce the cover 44, such that the piercing in the cover 44 may be sutured closed or otherwise closed after the guidewire 47 is removed. Alternately, a hemostasis port (not shown) or other port may be provided in a lateral side of the cover 44, allowing the guidewire 47 to be withdrawn from the inner lumen of the jumper 40 without the performance of additional actions to close the entry point of the guidewire 47 into the jumper 40. A nosecone (not shown) may be placed over the expanding end 42 of the jumper 40 when the expanding end 42 is in the insertion state in order to facilitate insertion of the expanding end of the jumper 40 to its intended location, as described in greater detail below.

Figure 11:
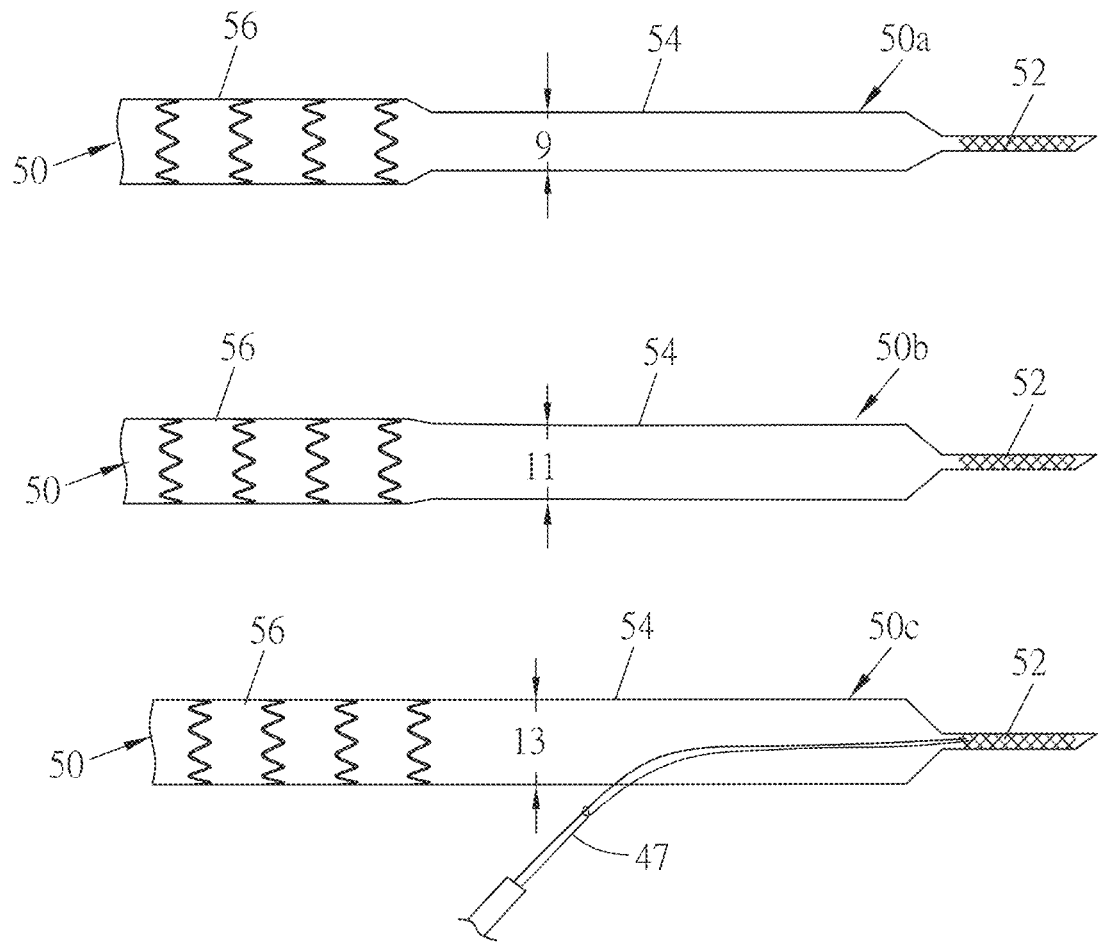
FIG. 11 is a side view of a plurality of second exemplary jumpers.

Referring also to FIG. 11, fixed-length jumpers 50 with different inside diameters are shown. Jumper 50a may have an inside diameter of substantially 9 mm, jumper 50b may have an inside diameter of substantially 11 mm, and jumper 50c may have an inside diameter of substantially 13 mm. Jumpers 50 with other inside diameters may be provided. Each jumper 50 is provided in a fixed length, which may be in the range of 10-20 cm. According to other embodiments, jumpers 50 may be provided in the 5-10 cm range. According to other embodiments, jumpers 50 may be provided in the 20-30 cm range. According to other embodiments, jumpers 50 may be provided in the 5-20 cm range. According to other embodiments, jumpers 50 may be provided in the 10-30 cm range. A particular jumper 50 may be provided in any suitable length. The jumpers 50 may be configured in substantially the same manner as the vascular anchor 2 described above. An expanding end 52 of a jumper 50 may be configured in substantially the same manner as a graft anchor 4, 6 as described above, such that the expanding end 52 is small in diameter in an insertion state (shown in FIG. 11) and larger in diameter in an expanded state. As with the vascular graft 2 described above, the expanding end 52 of the jumper 50 may be connected to and/or covered by a cover 54, which may be fabricated from PTFE or any other suitable material. The anchored end 56 of a jumper 50 may be the end of the cover 54 that is not connected to the expanding end 52 of the jumper 50. As shown in FIG. 11, the anchored end 56 of a jumper 50 may be substantially 16 mm in outer diameter in an expanded state. In one embodiment, the anchored end 56 is expandable from an insertion state to an expanded state (shown in FIG. 11), as described above with regard to the vascular graft 2. In other embodiments, the anchored end 56 is not substantially expandable, and has a substantially fixed outer diameter. The cover 54 may accommodate a guidewire 47 through a lateral side thereof, allowing the guidewire to access the lumen of the jumper 50 other than through the opening in the anchored end 56 of the jumper 50. Guidewire and/or cannula access to the lumen of the jumpers 50 is substantially as described above with regard to the jumpers 40 of FIG. 10.

Figure 39:
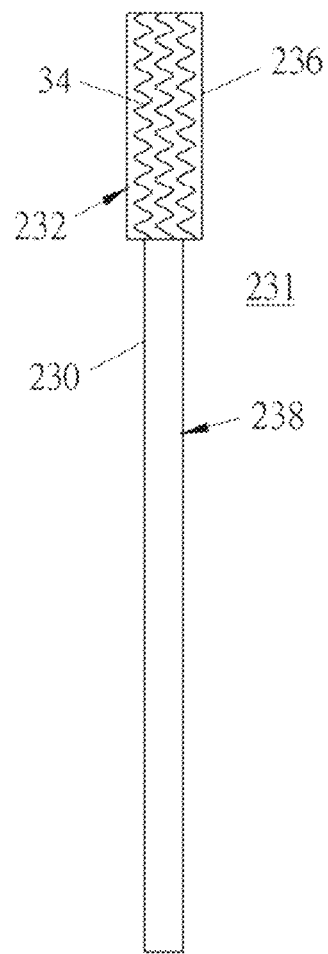
FIG. 39 is a side view of an embodiment of a graft connected to a stent to form a hybrid graft.
Figure 40:
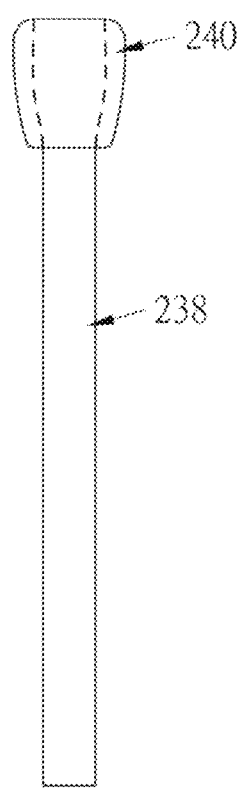
FIG. 40 is a side view of a sleeve.
Figure 41:
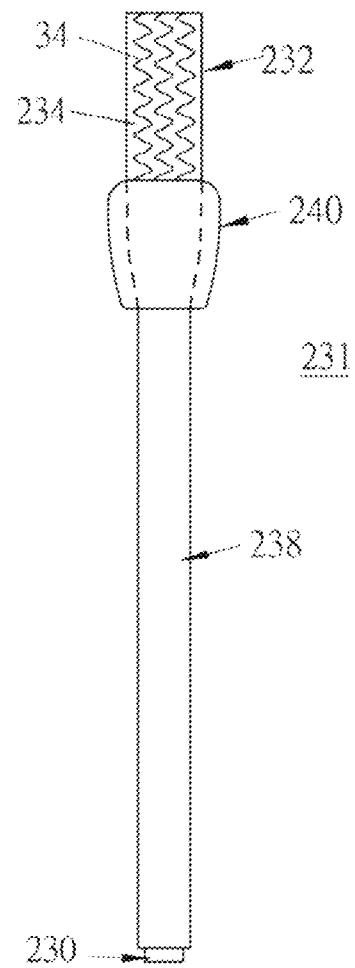
FIG. 41 is a side view of the hybrid graft of FIG. 39 combined with the sleeve of FIG. 40.

Referring also to FIGS. 39-41, according to some embodiments, at least one jumper graft 24a, 24b, 24c may be a hybrid graft 231. Referring to FIG. 39, a hybrid graft 231 may include a first section 230 and a second section 232 attached together. The first section 230 may be a graft fabricated from expanded polytetrafluoroethylene (ePTFE). The second section 232 may be a stent 234 encapsulated with a cover 236 that may be fabricated from polytetrafluoroethylene (PTFE) or other suitable material. The stent 234 advantageously is self-expanding; for example, the stent 234 may be fabricated from superelastic material such as nitinol; as another example, the stent 234 may be fabricated from plastically deformable material, such as stainless steel, that is compressed to an amount below its elastic limit, and then that compression is removed to allow the expandable mesh 34 to self-expand into place. The first section 230 may be sintered to the second section 232, using a sintering process such as known in the art. Alternately, the first section 230 may be affixed or attached to the second section 232 in any other suitable manner.

Referring also to FIGS. 40-41, such a jumper graft 241, 24b, 24c also may include a sleeve 238. The sleeve 238 may receive at least a portion of the first section 230 therein, such that first section 230 slides partially into a lumen of the sleeve 238. According to other embodiments, the sleeve 238 may receive all of the first section 230 therein, and also receive at least a portion of the second section 232 therein as well. The sleeve 238 may be fabricated from polyester, and/or from any other suitable material. At least a portion of the sleeve 238 may be rolled back toward the first section 230 to form a cuff 240. As seen in FIG. 41, at least the end of the second section 232 may extend out of the cuff 240, and at least the end of the first section 230 may extend out of the end of the sleeve 238 opposite the cuff 240. Alternately, at least one of the first section 230 and the second section 232 may reside completely within the lumen of the sleeve 238. The hybrid graft 231, and the sleeve 238, may be combined with a delivery device, as described in greater detail below.

Figure 42:
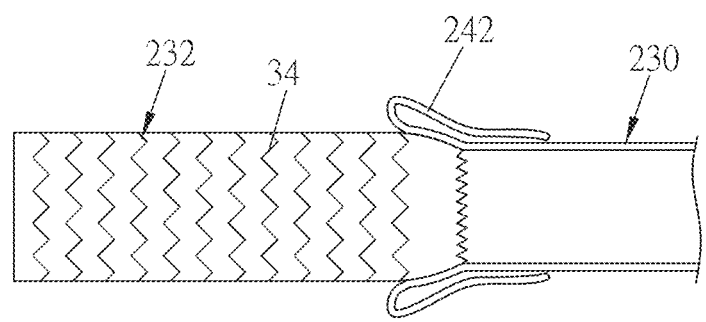
FIG. 42 is a side view of a step in the fabrication of an embodiment of a hybrid graft.
Figure 43:
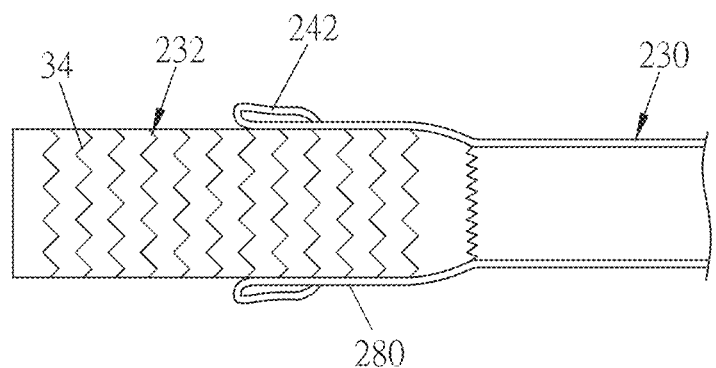
FIG. 43 is a side view of another step in the fabrication of the embodiment of a hybrid graft of FIG. 42.

Referring also to FIGS. 42-43, at least one hybrid graft 231 may be configured such that the first section 230 is a graft with a smaller diameter than the stent 34 of second section 232. In order to accommodate attachment of the larger-diameter second section 232 to the smaller-diameter first section 230, an end of the first section 230 is rolled back (everted) upon itself to form a cuff 242. Then, an end of the second section 232 is sutured to or otherwise attached to the cuff 242. At least part of the cuff 242 may be stretched over an end of the second section 232 prior to suturing, if desired, and if the first section 230 is composed of suitably stretchable material. According to some embodiments, an end of the second section 232 may be tapered to a smaller diameter than a remainder of the second section 232, such that the suturing or other attachment of that end of the second section 232 to the cuff 242 is facilitated. Referring also to FIG. 43, the cuff 242 then may be unrolled in part or in whole over an outer surface of the second section 232.

Figure 44:
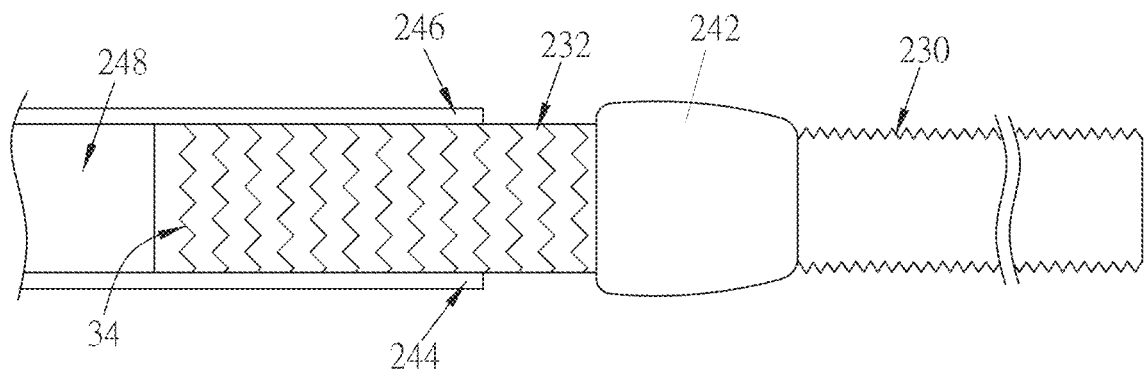
FIG. 44 is a side view of a step in the placement of the hybrid graft of FIGS. 42-43 into a blood vessel.
Figure 45:
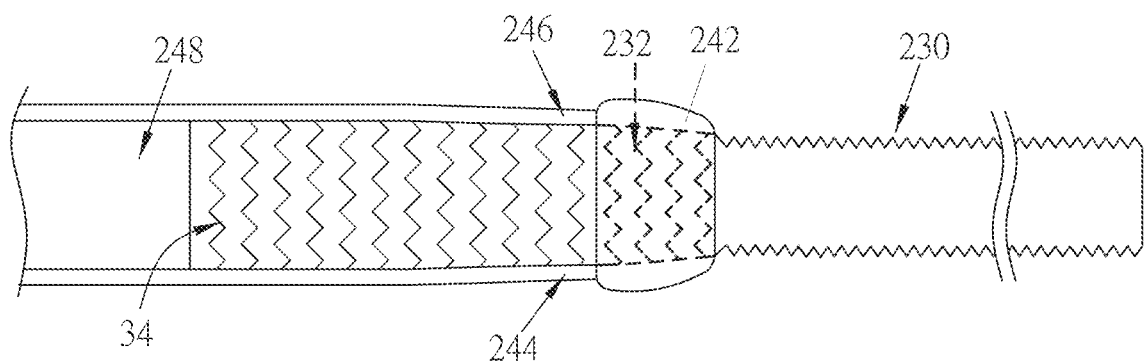
FIG. 45 is a side view of another step in the placement of the hybrid graft of FIGS. 42-43 into a blood vessel.

Referring also to FIG. 44, where the cuff 242 is not entirely unrolled onto the surface of the second section 232, the free end of the stent 34 of the second section 232 may be inserted into the lumen 248 of a blood vessel 244. Referring to FIG. 45, the cuff 242 then may be unrolled in part or in whole over the outer surface of the walls 246 of the blood vessel 244, and sewn onto the walls 246 of the blood vessel 244. According to some embodiments, the cuff 242 may be sewn to the walls 246 of the blood vessel 244 before unrolling the cuff 242 onto the blood vessel 244; according to other embodiments, the cuff 242 may be sewn to the walls 246 of the blood vessel 244 after unrolling the cuff 242 onto the blood vessel 244.

Figure 54:
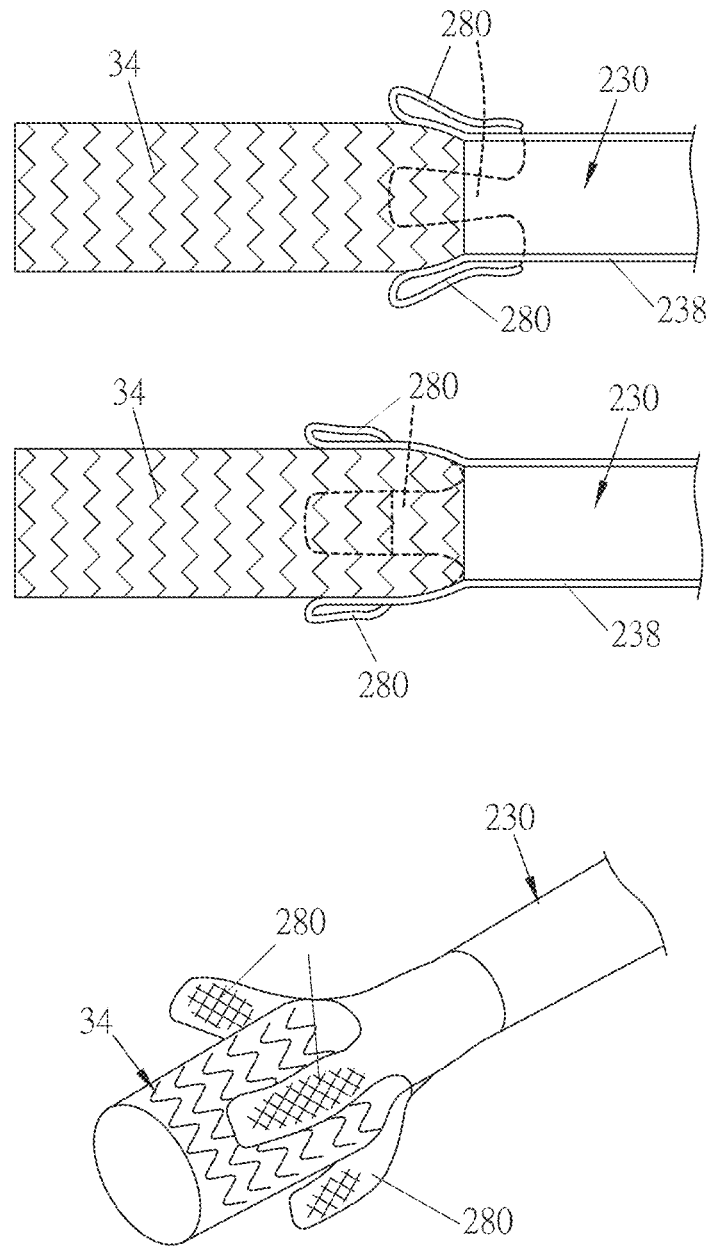
FIG. 54 is a perspective view of an embodiment of a hybrid graft utilizing suture flaps.

Referring also to FIG. 54, according to some embodiments, instead of a cuff 242 two or more suture flaps 280 are utilized. Advantageously, two to five suture flaps 280 are provided. Alternately, six or more suture flaps 280 are provided. The suture flaps 280 are circumferentially separated from one another at their free ends, as seen in FIG. 54, although the ends of at least two adjacent suture flaps 280 may be sutured together or adjacent to one another in use. Rather than the eversion of an end of the cuff 242, each suture flap 280 is folded back toward the graft 230. The suture flaps 280 may be utilized in a similar manner as the cuff 242, as described above. The free end of the stent 34 may be inserted into the lumen 248 of a blood vessel 244. The suture flaps 280 then may be unfolded in part or in whole over the outer surface of the walls 246 of the blood vessel 244, and sewn onto the walls 246 of the blood vessel 244.

Figures 47, 49:
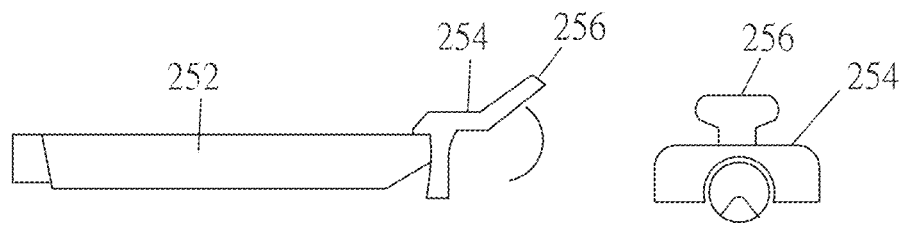
FIG. 47 is a side view of an exemplary sheath of FIG. 46.
FIG. 49 is a front view of the sheath of FIGS. 46-47.
Figure 48:
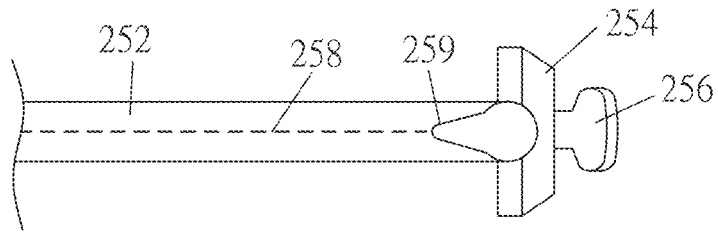
FIG. 48 is a bottom view of the sheath of FIG. 47.
Figure 46:
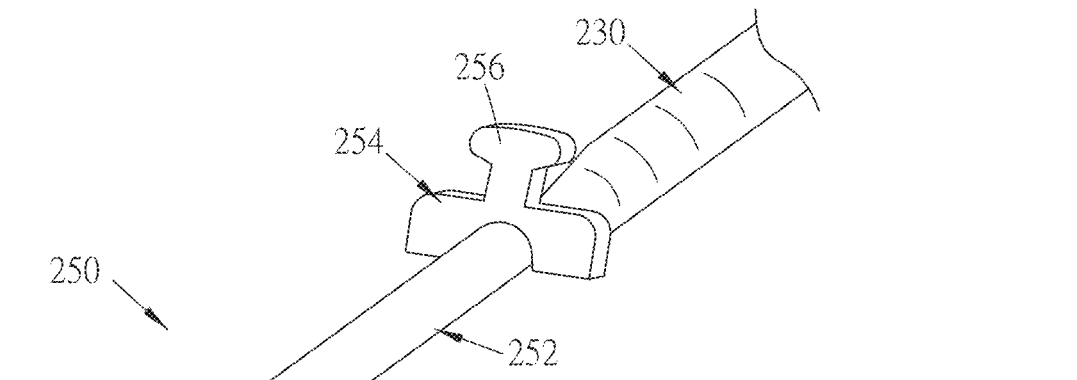
FIG. 46 is a perspective view of an embodiment of an exemplary deployment tool that includes a sheath, usable with a hybrid graft.

Referring also to FIG. 46, an exemplary deployment tool 250 is shown. The deployment tool 250 is particularly adapted for use with the hybrid graft 231 described above. According to other embodiments, the deployment tool 250 may be used with other embodiments of jumper grafts 24a, 24b, 24c described herein. The deployment tool 250 includes a sheath 252. The sheath 252 may be fabricated from any suitable material, such as PTFE, ePTFE, or PET mesh, such as DACRON® brand polyester. Referring also to FIGS. 47-49, a tab 254 may be attached to the sheath 252 at or near a proximal end of the sheath 252. Alternately, the tab 254 may be attached to the sheath 252 at or near the distal end of the sheath 252, or at any other suitable location along the sheath 252. The tab 254 may be generally bifurcated such that a part of the tab 254 extends lateral to the sheath 252 on both sides of the sheath 252, and the tab 254 may be affixed to the sheath 252 on the top of the sheath 252 as well as on both sides of the sheath 252. The tab 254 may be affixed to the sheath 252 in any suitable manner, such as by adhesive, by welding or by sintering. Alternately, the tab 254 may be fabricated integrally with the sheath 252. The tab 254 may include a pull 256 that is configured to be pulled by a user. The pull 256 may be shaped and/or textured to facilitate a user grasping the pull 256 and pulling it. The pull 256 may be angled upward from the longitudinal centerline of the sheath 252 in the proximal direction, as seen most clearly in FIG. 47. Referring also to FIG. 48, the sheath 252 may include a separation line 258 along which the sheath 252 preferentially separates when the pull 256 is grasped and pulled. The separation line 258 may be generally linear and generally parallel to the longitudinal centerline of the sheath 252. Alternately, the separation line 258 may describe any other suitable path along the sheath 252. According to one embodiment, the separation line 258 includes a set of perforations along the sheath 252. According to another embodiment, the separation line 258 includes a set of slits along the sheath 252. According to another embodiment, the separation line 258 is a line along the sheath 252 with a thickness that is less than the thickness of a remainder of the sheath 252, such that separation of the sheath 252 occurs preferentially along the separation line 258. According to other embodiments, the separation line 258 may be configured in any other suitable manner. At the proximal end of the separation line 258, the sheath 252 may include a V-shaped or otherwise-shaped cutout 259, which facilitates the separation of the sheath 252 from the proximal to distal direction. The cutout 259 advantageously is wider at its proximal end, which may be coterminous with the proximal end of the sheath 252, than at its distal end.

Figure 50:
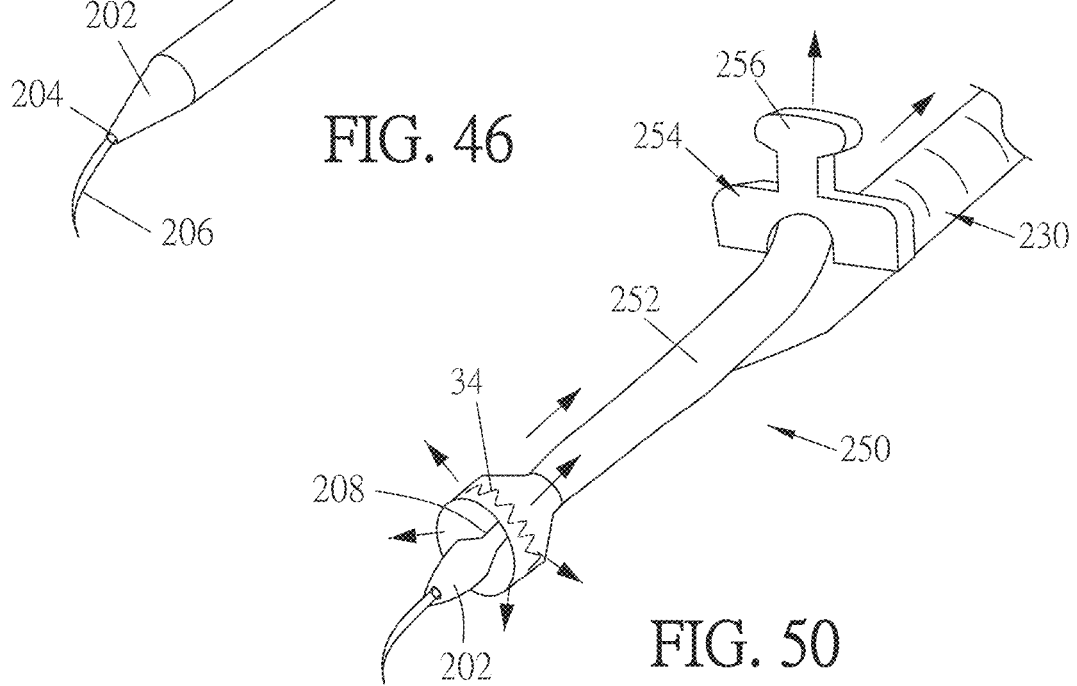
FIG. 50 is a perspective view of the deployment tool of FIG. 46 during the start of deployment of a hybrid graft.

Referring also to FIGS. 46 and 50, the deployment tool 250 includes a mandrel 208, with a dilator tip 202 at a distal end thereof. The dilator tip 202 is sized and shaped to dilate an incision or opening made in a vessel. A passage 204 is defined through the dilator tip 202. Advantageously, the passage 204 is straight and substantially coaxial with the longitudinal centerline of the deployment tool 250. Alternately, the passage 204 may be shaped differently, and/or oriented differently relative to the deployment tool 250. A guidewire 206 may be extensible through and/or retractable into the passage 204. An end of the guidewire 206 may be configured to curve when the guidewire 206 exits the passage 204. That is, upon exiting the passage 204, the distal end of the guidewire 206 curves away from the longitudinal centerline of the deployment tool 250, whether to one side or back toward the proximal direction.

A hybrid graft 231 may be wrapped around the mandrel 208. Alternately, another embodiment of jumper graft 24 may be wrapped around the mandrel 208. The hybrid graft 231 may be oriented on the mandrel 208 such that the second section 232 that includes the stent 34 is located at or near the distal end of the mandrel 208, such that the distal end of the stent 34 may be adjacent to or abut the proximal end of the dilator tip 202. The distal end of the first section 230 of the hybrid graft 231 may be located substantially at the junction between the tab 254 and the sheath 252. Alternately, the distal end of the first section 230 of the hybrid graft 231 may be located at a different location relative to the tab 254. The sheath 252 is wrapped around all or part of the second section 232 of the hybrid graft 231, which in turn is wrapped around the mandrel 208. The sheath 252 compresses at least part of the second section 232 of the hybrid graft 231 against or toward the mandrel 208. The separation line 258 is weak enough to allow a user to tear the sheath 252 along the separation line 258, but strong enough to withstand the outward force exerted by the second section 232 of the hybrid graft 231 while that second section 232 is compressed against or toward the mandrel 208.

Referring also to FIG. 50, the user inserts the guidewire 206 into an end of a blood vessel (such as the blood vessel 244 seen in FIG. 44) or into the side of a vessel (such as the aorta). The dilator tip 202 then is slid along the guidewire 206, along with the sheath 252, until the dilator tip 202 and then at least the distal end of the sheath 252 enters the vessel. The sheath 252 (and along with it the second section 232 of the hybrid graft 231) is slid into the vessel a suitable distance selected by the user. Once the hybrid graft 231 is in place, the user grasps the pull 256 and exerts a force away from the mandrel 208 and in the proximal direction. The sheath 252 separates along the separation line 258, and is peeled away from the hybrid graft 231 from the proximal end toward the distal end. The cutout 259 directs the force from the motion of the pull 256 (and thus the tab 254) toward the proximal end of the separation line 258 first. Thus, as the user continues to pull the pull 256 proximally and away from the mandrel 208, the separation line 258 continues to separate toward the distal direction. As the sheath 252 separates, it no longer compresses the second section 232 of the hybrid graft 231 against or toward the mandrel 208, and the stent 34 of the second section 232 expands outward. Once the separation line 258 is separated at its distal end, the stent 234 finishes its outward expansion, and the sheath 252 is pulled away from the hybrid graft 231. Any portion of the sheath 252 remaining inside the vessel is pulled out of the vessel, and the hybrid graft 231 is in place.

Referring also to FIG. 51, an exemplary deployment tool 260 is shown. The deployment tool 260 is particularly adapted for use with the hybrid graft 231 described above. According to other embodiments, the deployment tool 260 may be used with other embodiments of jumper grafts 24a, 24b, 24c described herein. According to other embodiments, the deployment tool 250 may be used with other embodiments of jumper grafts 24a, 24b, 24c described herein. The deployment tool 260 includes a sheath 252 that may be substantially as described above with regard to the deployment tool 250 and as shown in FIGS. 47-49. Further, the deployment tool 260 includes a mandrel 208, and a dilator tip 202 configured to receive a guidewire 206 that may be substantially as described above with regard to the deployment tool 250 and as shown in FIGS. 46 and 50. A needle 210 may extend retractably through the dilator tip 202, and may be coupled to a needle control 277 located more proximally on the deployment tool 260. The needle 210 may be coupled to the needle control 277 via a linkage or any other suitable structure or mechanism. The needle 210 may be retracted into the dilator tip 202 by proximal motion of the needle control 277, and extended out of the dilator tip 202 by distal motion of the needle control 277. The needle 210 may include an aperture therethrough through which the guidewire 206 may pass. Optionally, as seen in FIG. 53, the mandrel 208 may be ribbed. The hybrid graft 231 may be mounted on the mandrel 208 of the deployment tool 260, and held in place by the sheath 252, substantially as described above with regard to the deployment tool 250.

The deployment tool 260 also includes a tab 254 that may be generally as described above with regard to the deployment tool 250 and as shown in FIGS. 47-49. The tab 254 applies a compressive force to the sheath 252 at or near a proximal end of the sheath 252. Referring also to FIGS. 51-53, the tab 254 may be generally U-shaped. One or more wings 262 may extend from the tab 254. The wings 262 may be affixed to the tab 254 or formed integrally with the tab 254. The wings 262 each angle outward from the tab 254. The tab 254 itself may include a living hinge defined therein, between the junction of each wing 262 and the tab 254. The wings 262 are configured such that motion of the wings 262 toward one another, such as by a pinching motion of a user's hand and the application of a pinching force, causes the free ends 264 of the tab 254 to move apart from one another, as described in greater detail below.

An arm 266 may extend proximally from the tab 254. The arm 266 may be affixed to tab 254, fabricated integrally with the tab 254, or connected to the tab 254 in any suitable manner. The arm 266 may be substantially cylindrical, or may have any other suitable shape and/or cross-section. Advantageously, the arm 266 may be rigid. Alternately, the arm 266 may be configured to be flexible. The distal end of the arm 266 may be connected to the tab 254, while the proximal end of the arm 266 may be connected to a hinge 268. The connection between the arm 266 and the hinge 268 allows the arm 266 to rotate about the hinge 268, such that rotation of the arm 266 causes the tab 254 to move along an arc of a circle, upward from the longitudinal centerline of the sheath 252 and also proximally, as described in greater detail below. The hinge 268 may be attached to or part of a support member 272. Referring to FIG. 53, the distal end of the support member 272 may be connected to the proximal end of the mandrel 208. The mandrel 208 may be attached to or part of the support member 272. The support member 272 may be substantially rigid. Optionally, a grip 270 may be attached to the arm 266 in any suitable manner. For example, the grip 270 may include an aperture 274 defined therethrough to receive the arm 266, and the arm 266 may be slidable relative to the arm 266. Alternately, the arm 266 may be pressure fit to the aperture 274, adhered to the aperture 274, welded to the aperture 274, or otherwise fixed to the aperture 274. Grip wings 276 may extend laterally or in any other suitable direction from the aperture 274. The grip wings 276 may be generally planar and rectangular, or may have any other suitable shape. The user may utilize the grip 270 to lift the tab 254 away from the mandrel 208, as described in greater detail below. The grip 270 may be affixed to the sheath 252, such that proximal motion of the grip 270 relative to the arm 266 may cause the sheath 252 to split.

Referring also to FIG. 51, the user inserts the guidewire 206 into an end of a blood vessel (such as the blood vessel 244 seen in FIG. 44) or into the side of a vessel (such as the aorta). The needle 210 is extended distally and used to puncture the side of a vessel. The dilator tip 202 is then pushed into the puncture, expanding it, and the needle 210 is withdrawn proximally into the dilator tip 202 by proximal motion of the needle control 277. The guidewire 206 is then slid into the vessel through the dilator tip 202, and optionally through the aperture in the needle 210 (now residing in the dilator tip 202 and no longer exposed). The dilator tip 202 then is slid along the guidewire 206, along with the sheath 252, until the dilator tip 202 and then at least the distal end of the sheath 252 enters the vessel. The sheath 252 (and along with it the second section 232 of the hybrid graft 231) is slid into the vessel a suitable distance selected by the user. Once the hybrid graft 231 is in place, the user grasps the wings 262 and compresses them together. Motion of the wings 262 toward one another causes the free ends 264 of the tab 254 to move apart from one another. Where the tab 254 includes a living hinge, that living hinge facilitates the motion of the free ends 264 of the tab 254 apart from one another. The tab 254 thus no longer compresses the sheath 252 against the mandrel 208.

The user then grasps the grip 270 and pulls it proximally along the arm 266, splitting the sheath 252 starting at its proximal end, in a manner similar to that described above with regard to the deployment tool 250. The sheath 252 may include a separation line along which the sheath 252 separates. As the grip 270 moves proximally, splitting of the sheath 252 continues. As the sheath 252 separates, it no longer compresses the second section 232 of the hybrid graft 231 against or toward the mandrel 208, and the stent 34 of the second section 232 expands outward. Once the sheath 252 has separated at its distal end, the stent 234 finishes its outward expansion, and the sheath 252 is pulled away from the hybrid graft 231. The arm 266 is then rotated about the hinge 268 to move the grip 270 out of the way, and the grip 270 may be moved to a position proximal to the proximal end of the deployment tool 260. Any portion of the sheath 252 remaining inside the vessel is pulled out of the vessel, as seen in FIG. 52, and the hybrid graft 231 is in place.

Referring also to FIG. 55, another exemplary deployment tool 290 is shown. The deployment tool 290 may be used with a double stent graft 292. The double stent graft 292 may be fabricated in generally the same manner as the hybrid graft 231 described above, with differences described below. The double stent graft utilizes two stents 234, which may be aligned generally with one another along their longitudinal centerlines, and which may be connected to or affixed to one another. Alternately, the two stents 234 may be one single stent 234 that extends generally along the length of the double stent graft 292. Alternately, the two stents 234 may be separated from one another longitudinally to allow for greater flexibility of the double stent graft 292. The sheath 252 may include two separate sheaths 252a, 252b, where the sheath 252a is located distal to the sheath 252b. Each sheath 252s, 252b may be configured to split along a separation line, as described above. Two tabs 294 may be attached to an end of each sheath 252a, 252b. Alternately, one tab 294 or three or more tabs 294 may be attached to an end of each sheath 252a, 252b. The tabs 294 may be generally circular, or may be shaped in any other suitable manner, such as oval or polygonal. Alternately, the tabs 294 may be substantially linear or may be curvilinear. The tabs 294 may be oriented at generally ninety degrees circumferentially spaced apart from one another. Alternately, the tabs 294 may be oriented and spaced relative to one another in any other suitable manner. All of the tabs 294 may be located at generally the same longitudinal position relative to the deployment tool 290. Alternately, the tabs 294 associated with the first sheath 252a may be longitudinally spaced apart from the tabs 294 associated with the second sheath 252b. As described below, the sheaths 252a, 252b are configured to split longitudinally in opposite directions from one another. Each sheath 252a, 252b may be splittable in the direction toward a free end of that sheath 252a, 252b.

The deployment tool 290 may be used with the hybrid graft 231 described above. According to other embodiments, the deployment tool 290 may be used with other embodiments of jumper grafts 24a, 24b, 24c described herein. According to other embodiments, the deployment tool 290 may be used with other embodiments of jumper grafts 24a, 24b, 24c described herein. The deployment tool 290 includes a sheath 252 that may be substantially as described above with regard to the deployment tool 250 and as shown in FIGS. 47-49. Further, the deployment tool 290 includes a mandrel 208, and a dilator tip 202 configured to receive a guidewire 206 that may be substantially as described above with regard to the deployment tool 250 and deployment tool 260, and as shown in FIGS. 46 and 50. Optionally, as seen in FIG. 53, the mandrel 208 may be ribbed. The double stent graft 292 may be mounted on the mandrel 208 of the deployment tool 290, and held in place by the sheath 252, substantially as described above with regard to the deployment tool 250 and the deployment tool 260.

Referring also to FIG. 55, the user inserts the guidewire 206 into the side of, or into an end of, a blood vessel. The dilator tip 202 then is slid along the guidewire 206, along with the sheath 252, until the dilator tip 202 and then at least the distal end of the sheath 252 enters the vessel. The sheath 252 (and along with it the distal end of the double stent graft 292) is slid into the vessel 244 a suitable distance selected by the user. Referring also to FIG. 56, once the double stent graft 292 is in place, the user grasps the tabs 294 attached to the first sheath 252a and pulls them away from one another, splitting the first sheath 252a. As the first sheath 252a separates, it no longer compresses the distal end of the double stent graft 292 against or toward the mandrel 208, and the stent 234 or distal portion of the stent 234 at the distal end of the double stent graft 292 expands outward. Once the first sheath 252a has separated at its distal end, the stent 234 or distal portion of the stent 234 finishes its outward expansion, and the first sheath 252a is pulled away from the double stent graft 292. Any portion of the first sheath 252a remaining inside the vessel is pulled out of the vessel, as seen in FIG. 52, and the distal end of the double stent graft 292 is in place. The guidewire 206 then may be withdrawn from the blood vessel 244 through the lumen of the double stent graft 292.

Next, referring also to FIG. 57, the user may pull a vascular graft 296 over the proximal end of the double stent graft 292. The end of the vascular graft 296 may be pulled into proximity with the remaining tabs 294. Once the vascular graft 296 is in place on the double stent graft 292, the user grasps the tabs 294 attached to the second sheath 252b and pulls them away from one another, splitting the second sheath 252b. As the sheath 252b separates, it no longer compresses the proximal end of the double stent graft 292 against or toward the mandrel 208, and the stent 234 or portion of the stent 234 at the proximal end of the double stent graft 292 expands outward. Once the second sheath 252b has separated at its proximal end, the stent 234 or proximal portion of the stent 234 finishes its outward expansion, and the second sheath 252b is pulled away from the double stent graft 292 out of the end of the vascular graft 296. The proximal end of the double stent graft 292 is thus secured in place.

Operation—Aortic Graft

Referring to FIG. 12, an exemplary method of implanting an aortic graft 20 with a central section 22 is shown. The patient is placed on a cardiopulmonary bypass pump, the heart is stopped, and clamps are placed on the aorta 60 spaced apart from the ascending aorta. Incisions 62 are made in the aorta 60 to separate the ascending aorta, and the ascending aorta is removed. The central section 22 of the aortic graft 20 is then sutured to the proximal end of the aortic stump 70 at or in proximity to the incision 62. In this way, the lumen of the central section 22 of the aortic graft 20 is easily accessible.

As shown in FIG. 12, a manifold 24d is fixed to the central section 22 of the aortic graft 20, and three jumper grafts 24a, 24b, 24c extend from the manifold 24d. Alternately, where three jumper grafts 24 are provided on the central section 22, three jumpers 40, 50 are selected. Where one of the jumpers 40 is selected, the jumper 40 may be utilized as is, or the jumper 40 may be cut to a shorter length. That length is selected by a clinician based on the distance between the central section 22 of the aortic graft 20 and the artery 64, 66, 68 to be connected. Where one of the jumpers 50 is selected, its length is fixed, and that jumper 50 is not cut to a shorter length. The selected jumper 40, 50 is then inserted into the lumen of the central section 22 of the aortic graft 20 through one of the jumper grafts 24 until most of the jumper 40, 50 has been pulled through that jumper graft 24. Where a jumper 50 is used, advantageously the jumper 50 is pulled through the jumper graft 24 until at least part of the anchored end 56 of that jumper 50 is located within the expandable mesh 34 of the jumper graft 24. The jumper 40, 50 may be pulled or pushed through the corresponding jumper graft 24 with a guidewire. Advantageously, a standard interventional balloon (not shown) is positioned within the anchored end 46, 56 of the jumper 40, 50, and that balloon is inflated. That inflation expands the anchored end 46, 56 to its expanded state, and also expands the expandable mesh 34 to its expanded state. In this way, the anchored end 46, 56 of the jumper 40, 50 is pressure-fit to the corresponding expandable mesh 34. The guidewire and interventional balloon are withdrawn. Alternately, where the jumpers 40, 50 are fabricated integrally with the central section 22 of the aortic graft 20, the selection of a jumper 40, 50 and its insertion into the central section 22 of the aortic graft 20 is omitted. Alternately, at least one of the jumpers 40, 50 may be inserted into a corresponding artery 64, 66, 68 prior to connecting that jumper 40, 50 to the central section 22 of the aortic graft 20.

Next, the remainder 20a of the aortic graft 20 is inserted into the descending aorta 74. This remainder may be fixed to the central section 22 of the aortic graft 20, or may be a separate component that is connected to the central section 22 of the aortic graft 20. In some embodiments, the central section 22 of the aortic graft 20 is first sutured to the descending aorta 74 at or in proximity to the incision 62. The remainder 20a of the aortic graft 20 may be inserted through the hemostasis value 32 into the access port 30 and then through the lumen of the central section 22 into the descending aorta 72, such as via a guidewire (not shown) inserted through the hemostasis value 32 and through the access port 30. The remainder 20a of the aortic graft 20 may be deployed in any suitable manner, such as by the inflation of a standard interventional balloon. In other embodiments, the remainder 20a of the aortic graft 20 may be self-expanding. As needed, the remainder 20a of the aortic graft 20 may be sutured to the descending aorta 72 to ensure that remainder 20a of the aortic graft 20 remains in place. Alternately, such suturing need not be performed. Also, the remainder 20a of the aortic graft 20 may be sutured or otherwise affixed to the central section 22 of the aortic graft 20. According to other embodiments, the remainder 20a of the aortic graft 20 is inserted into the descending aorta 74, and then the central section 22 is sutured to the descending aorta 74. With the remainder 20a of the aortic graft 20 secured, the guidewire, interventional balloon, and/or other mechanism or device that had been inserted through the access port 30 is withdrawn through the hemostasis valve 32. The heart is then restarted and the patient removed from cardiopulmonary bypass according to standard practice.

At least one jumper graft 24 may be implanted by utilizing the deployment tool 200. Referring to FIG. 27, as described above, the jumper graft 24 initially is wrapped about a mandrel 208 of the deployment tool 200. As described above, referring also to FIG. 35, the containment sheath 180 is rolled about a jumper graft 24 in an initial, compressed configuration. Referring also to FIGS. 36-37, a pull wire 190 passes through longitudinally-adjacent holes 188 in the rolled containment sheath 180. In this way, the pull wire 190 holds the adjacent edges 182a, 182b of the containment sheath 180 together, and thereby the containment sheath 180 compresses the jumper graft 24 against the mandrel 208.

To begin the deployment process, the user grasps the handle 212 of the deployment tool 200, and actuates the needle advancement button 224. The distal force applied by the user to the needle advancement button 224 compresses the compression spring 222 coupled to the needle advancement button 224, at the same time that the distal force applied by the user to the needle advancement button 224 advances the needle deployment controller 228 distally. Referring also to FIG. 28, because the needle deployment controller 228 is affixed to or otherwise coupled to the needle 210, the distal advancement of the needle deployment controller 228 causes the needle 210 to advance distally out of the passage 204 through the dilator tip 202. Advantageously, the guidewire 206 extends out of the passage 204 through the dilator tip 202 a distance of substantially 1-2 centimeters prior to the advancement of the needle 210. Alternately, the guidewire 206 may extend out of the passage 204 a different distance, or may not extend out of the passage 204 at all prior to the advancement of the needle 210. As described above, advantageously the needle 210 is hollow, and the guidewire 206 passes through the needle. Thus, as the needle 210 advances distally, and the guidewire 206 remains substantially longitudinally stationary, the needle 210 temporarily straightens the curved guidewire 206. The needle 210 continues to be advanced distally until its distal end is located distal to the distal end of the guidewire 206. In this way, the distal end of the guidewire 206 does not interfere with the ability of the needle 210 to puncture tissue. The needle 210, which had been previously protected against contact with tissue of a patient, is now exposed.

The user then penetrates a blood vessel of the patient with the needle 210, at a location at which the user wishes to insert a jumper graft 24. After the needle 210 punctures the blood vessel, the user releases the needle advancement button 224. Stored energy in the compression spring 222 then urges the needle advancement button 224 proximally, thereby causing the needle deployment controller 228 that is affixed to or otherwise coupled to the needle advancement button 224 to move proximally. In turn, the needle deployment controller 228 thus moves the needle 210 proximally, back into the passage 204 in the dilator tip 202. As the needle 210 moves proximally, and the guidewire 206 remains substantially longitudinally stationary, the distal end 206 of the guidewire 206 is exposed, and remains within the lumen of the blood vessel. Referring also to FIG. 29, as described above, the distal tip of the guidewire 206 curves proximally, such that the guidewire 206 is atraumatic relative to the interior of the blood vessel.

The guidewire 206 is then advanced further into the lumen of the blood vessel, approximately the length of the jumper graft 24. Such advancement may be performed manually, by pushing the proximal end of the guidewire 206 that extends out of the proximal end of the deployment tool 200. Alternately, such advancement may be performed by a mechanism in the deployment tool 200. The user then advances the deployment tool 200 along the guidewire 206. The dilator tip 202 is blunt, and as it is pushed against the puncture in the blood vessel made by the needle 210, it dilates that puncture and passes through the dilated puncture into the lumen of the blood vessel. As the deployment tool 200 continues to be advanced through the dilated puncture, the compressed jumper 24 enters the lumen of the blood vessel. The user continues to advance the deployment tool 200 until the suture cuff 160 of the jumper graft 24 is in proximity to the puncture in the blood vessel, at which point the user ceases advancement of the deployment tool 200.

The jumper graft 24 is then deployed. The pull wire 190 is retracted proximally. The user may grasp a proximal portion of the pull wire 190 and pull it proximally. Alternately, such retraction may be performed by a mechanism in the deployment tool 200. As the pull wire 190 is retracted proximally, the pull wire 190 sequentially withdraws from the holes 188 in the containment sheath 180, starting with the most-distal hole 188. As described above, the containment sheath 180 is compressed about the jumper graft 24 by the passage of the pull wire 190 through the holes 188, which holds the containment sheath 180 in the compressed position. As the pull wire 190 is retracted proximally out of the holes 188, the edges 182 of the containment sheath 180 are freed to move apart from one another, starting at the proximal end of the containment sheath 180. The jumper graft 24, which had been compressed by the containment sheath 180, is thus able to expand radially as the pull wire 190 is retracted, starting at the proximal end of the jumper graft 24. The jumper graft 24 expands radially, proximal to distal, until the pull will 190 has been removed from the distalmost hole 188 in the containment sheath 180. The jumper graft 24 is then fully radially expanded within the lumen of the blood vessel. The pull wire 190 is then fully separated from the deployment tool 200, if it has not been already. The jumper graft 24 is no longer compressed about the mandrel 208 of the deployment tool 200, such that the mandrel 208 of deployment tool 200 can be withdrawn easily from the lumen of the jumper graft 24. The deployment tool 200 is moved proximally out of the lumen of the jumper graft 24, leaving the jumper graft 24 in place relative to the blood vessel.

The suture cuff 160, if utilized, then may be adjusted to meet the wall of the blood vessel 165. The jumper graft 24 extends outward through the dilated puncture in the blood vessel 165 at an angle relative to the longitudinal centerline of the blood vessel 165. Thus, the suture cuff 160 may be unrolled differentially on opposed sides of the jumper graft 24 to meet the wall 167 of the blood vessel 165. That is, on a side of the jumper graft 24 that forms an obtuse angle relative to the blood vessel 165, the suture cuff 160 may be unrolled to a greater degree than the side of the jumper graft 24 that forms an acute angle relative to the blood vessel 165. Indeed, the jumper graft 24 may be advanced into the lumen of the blood vessel 165 such that the suture cuff 160 initially contacts the wall of the blood vessel 165 on the side of the jumper graft 24 that forms an acute angle relative to the blood vessel 165. The suture cuff 160 is differentially unrolled until the suture cuff 160 substantially engages tissue around the circumference of the suture cuff 160. Then, the clinician sutures the suture cuff 160 to the wall 167 of the blood vessel 165 to secure the jumper graft 24 to the blood vessel 165. The suture cuff 160 provides a thick area to suture in order to allow for a secure sutured connection between the jumper graft 24 and the blood vessel 165. When suturing is complete, the jumper graft 24 is secured to the blood vessel 165.

In conjunction with the restarting of the heart, the jumper grafts 24a, 24b, 24c or the manifold 24d are clamped to prevent aortic blood from leaking therethrough during the next portion of the procedure. According to some embodiments, one or more jumper grafts 24 are connected to the corresponding arteries 64, 66, 68 with a deployment tool 200 as described above. According to other embodiments, jumper grafts 24a, 24b, 24c are inserted into the corresponding arteries that arise from the aortic arch: the brachiocephalic trunk 64, left common carotid artery 66, and left subclavian artery 68. An incision is made in one of those arteries 64, 66, 68 with a length shorter than or substantially the same as the diameter of the expanding end 42, 52 of the selected jumper 40, 50. The expanding end 42, 52 of the selected jumper graft 24a, 24b, 24c is inserted through that incision in the insertion state. Such insertion may be performed under direct vision in an open procedure, or may be performed percutaneously in whole or in part. A nosecone (not shown) may be tapered and may be located distal to the expanding end 42, 52 to facilitate entry of the expanding end 42, 52 through the incision into the lumen of the selected artery 64, 66, 68. A guidewire may extend into the lumen of the selected jumper graft 24a, 24b, 24c and through the expanding end 42, 52 to the nosecone; such guidewire advantageously extends out of the proximal end of the selected jumper graft 24a, 24b, 24c rather than through the cover 44, 54 of that jumper graft 24a, 24b, 24c. The expanding end 42, 52 is placed in the lumen of the corresponding artery 64, 66, 68. Advantageously, a standard interventional balloon (not shown) is positioned within the expanding end 42, 52 of the jumper graft 24a, 24b, 24c, and that balloon is inflated. That inflation expands the expanding end 42, 52 to its expanded state, which has a diameter larger than the inner diameter of the corresponding artery 64, 66, 68 into which it was placed. In this way, the expanding end 42, 52 is pressure-fit to the corresponding artery 64, 66, 68. The guidewire and interventional balloon are withdrawn. The connection of a jumper graft 24a, 24b, 24c to each artery 64, 66, 68 then is performed for the other two arteries 64, 66, 68.

Figure 12A:
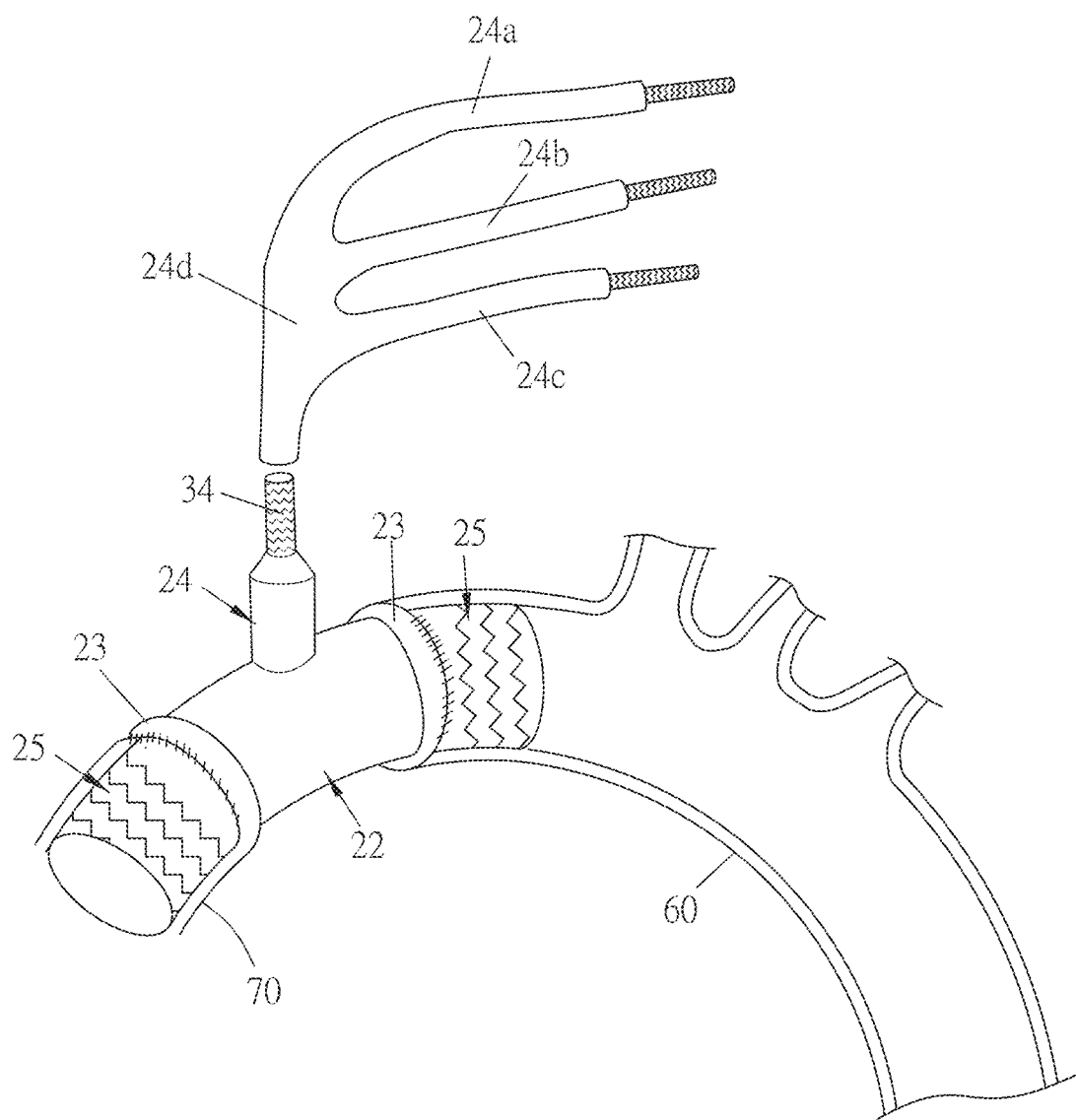
FIG. 12A is a side view of the exemplary implantation of FIG. 12 with exemplary differences therefrom.

Referring to FIG. 12A, another exemplary method of implanting an aortic graft 20 with a central section 22. The method is performed substantially as described above with regard to FIG. 12, with differences described in this paragraph. After the ascending aorta is removed, an end of the central section 22 of the aortic graft 20 is inserted into the aortic stump 70. The central section 22 includes a central section anchor 25, which self-expands within the aortic stump 70 to assist in holding the central section 22 in place.

Alternately, a standard interventional balloon may be used to expand, or assist in expanding, the central section anchor 25. The central section anchor 25 placed in the aortic stump 70 may be referred to as the proximal central section anchor 25. That end of the central section 22 of the aortic graft 20 is then sutured to the aortic stump 70 at or in proximity to the incision 62. The central section 22 includes a suture band 23, and the clinician sutures the aortic stump 70 to the suture band 23 for additional security. An end of the central section 22 of the aortic graft 20 is inserted into the descending aorta 72. The central section 22 includes a central section anchor 25, which self-expands within the descending aorta 72 to assist in holding the central section 22 in place. Alternately, a standard interventional balloon may be used to expand, or assist in expanding, the central section anchor 25. The central section anchor 25 placed in the descending aorta 72 may be referred to as the distal central section anchor 25. That end of the central section 22 of the aortic graft 20 is then sutured to the descending aorta 72 at or in proximity to the incision 62. The central section 22 includes a suture band 23, and the clinician sutures the descending aorta 72 to the suture band 23 for additional security. The heart is then restarted and the patient removed from cardiopulmonary bypass according to standard practice.

Next, a single manifold 24d is connected to a jumper graft 24 on the central section of the aortic graft 20. Advantageously, a standard interventional balloon (not shown) is positioned within the expandable mesh 34 of the jumper graft 24, and that balloon is inflated. That inflation expands the expandable mesh 34 to an expanded state. In this way, the anchored end of the single manifold 24d is pressure-fit to the corresponding expandable mesh 34. As shown in FIG. 9, the individual jumper grafts 24a, 24b, 24c extend from the manifold 24d, and are in fluid communication with the lumen of the central structure 22 after connection of the manifold 24d to the jumper graft 24.

Figure 12B:
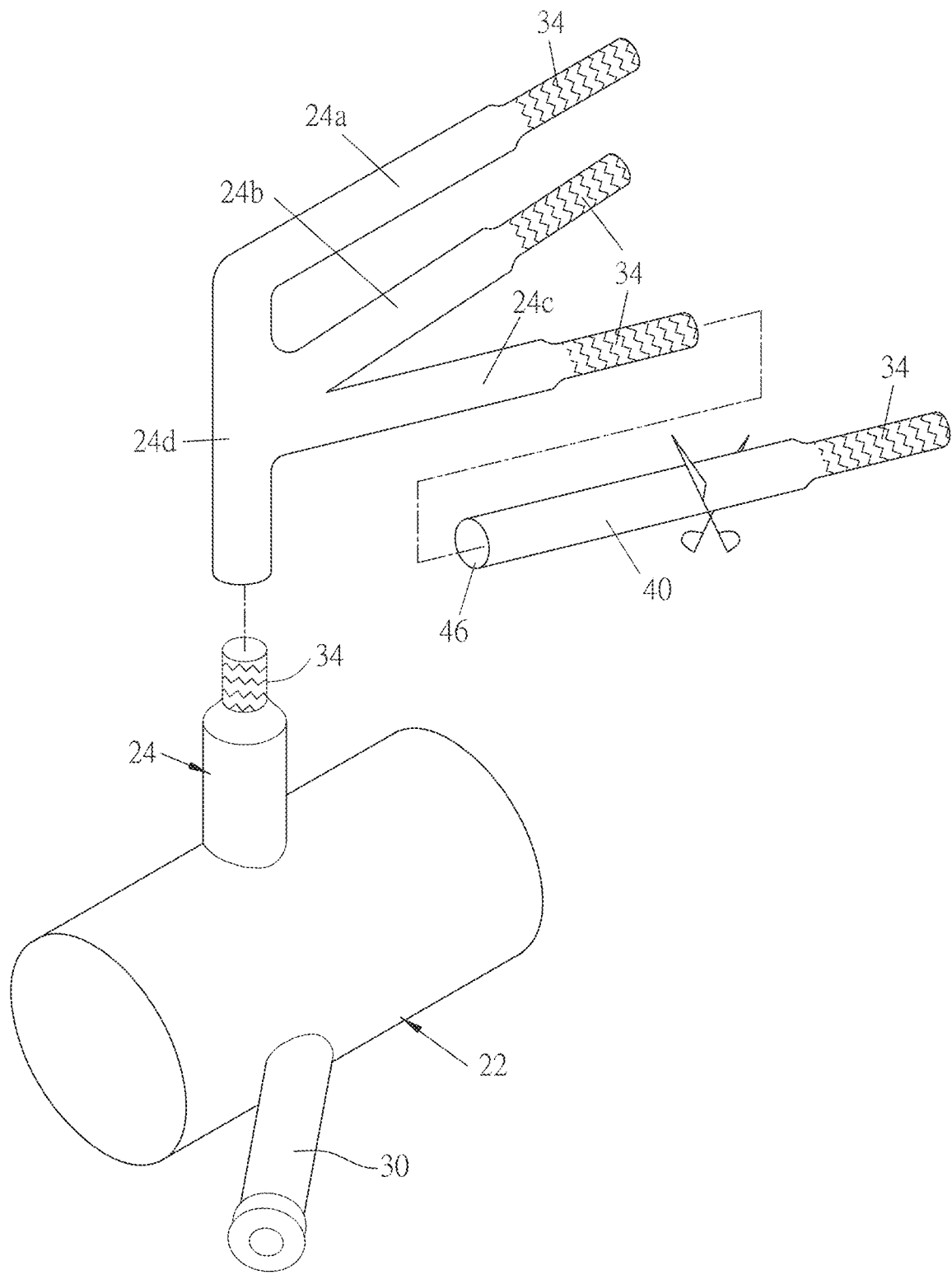
FIG. 12B is a side view of the exemplary implantation of FIG. 12A with exemplary differences therefrom.

Referring to FIG. 12B, another exemplary method of implanting an aortic graft 20 with a central section 22. The method is performed substantially as described above with regard to FIG. 12A, with differences described in this paragraph. After connection of both ends of the central section 22 to the remainder of the aorta, the patient's heart is restarted. The manifold 24d is connected to a jumper graft 24 that is connected to the central section 22, as described above. In this embodiment, the manifold includes two individual jumper grafts 24a, 24c connected thereto, and a third jumper graft 24b branches off jumper graft 24c. Alternately, jumper graft 24b may branch off jumper graft 24a. The clinician determines whether those jumper grafts 24a, 24b, 24c are sufficiently long to reach desired locations in the patient. If not, a jumper graft 24a, 24b, 24c may be utilized, as described with regard to FIG. 10. The anchored end 46 of that jumper graft 24a, 24b, 24c may be cut to any suitable length, and then placed over the expandable mesh 34 at the distal end of a jumper graft 24c that is too short. Such a jumper 40 may be used with any or all of the jumper grafts 24a, 24b, 24c. Advantageously, a standard interventional balloon (not shown) is positioned within the expandable mesh 34, and that balloon is inflated. That inflation expands the expandable mesh 34 to an expanded state. In this way, the anchored end 46 of the graft 24a, 24b, 24c is pressure-fit to the corresponding expandable mesh 34.

Figure 13:
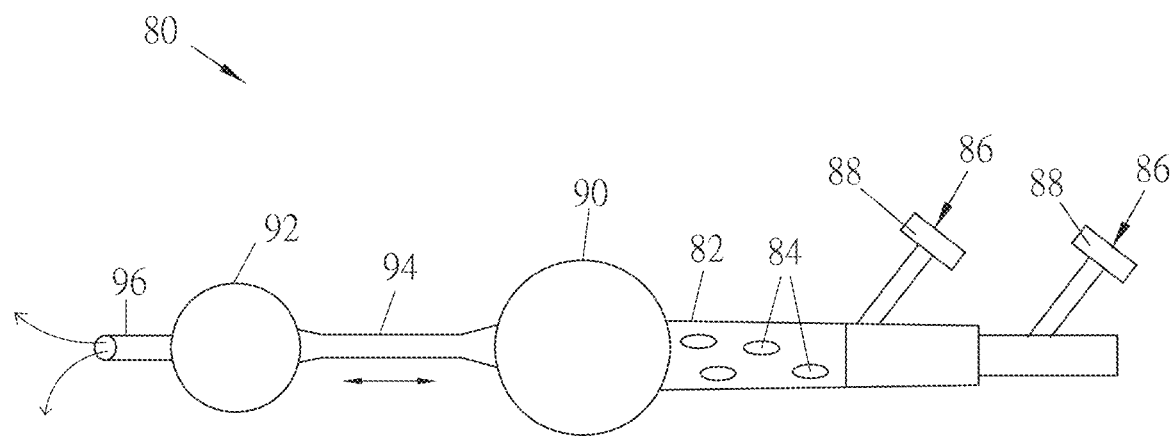
FIG. 13 is a side view of an exemplary dual auto-perfuser.

Referring to FIGS. 13-14, another exemplary method of implanting an aortic graft 20 with a central section 22 is shown. This method may be referred to as the "warm elephant trunk" method. The warm elephant trunk method utilizes a dual auto-perfuser device 80, seen in FIG. 13. The dual auto-perfuser 80 includes a flexible cannula 82 with a lumen defined therethrough, and one or more apertures 84 defined through the cannula 82 from the lumen to the outer surface. At least one access port 86 is connected to the cannula 82. The access port 86 includes a lumen that allows instruments and/or guidewires to be inserted therethrough into and withdrawn therethrough out of the lumen of the cannula 82. One end of the access port 86 connects to the cannula 82; the other end of the access port 86 optionally includes a hemostasis valve 88 that allows instruments and/or guidewires to enter and exit the access port 86 while blood is flowing through the lumen of the cannula 82. One or more access ports 86 may be provided. Each access port 86 may be connected to the cannula 82 off-axis, such that the longitudinal centerline of the access port 86 is angled relative to the longitudinal centerline of the cannula 82, or on-axis, such that the longitudinal centerline of the access port 86 is substantially the same as the longitudinal centerline of the cannula 82.

The first balloon 90 of the dual auto-perfuser 80 may be substantially hollow to allow for the flow of blood therethrough. Alternately, a tube (not shown) extends between opposite sides of the first balloon 90 and connects to the cannula 82, to allow for blood flow through the tube across the first balloon 90. A bridge tube 94 is connected to the first balloon 90, and to a second balloon 92 spaced apart from the first balloon. The first balloon 90 and/or second balloon 92 are slidable relative to the bridge tube 94, which may be pressure fit to the balloons 90, 92. Flanges (not shown) at both ends, or other suitable structure features, may prevent the bridge tube 94 from pulling out of the balloons 90, 92. The bridge tube 94 may be pressure fit or line-to-line fit to the balloons 90, 92 and/or tubes within the balloons 90, 92, in order to allow the first balloon 90 and/or second balloon 92 to slide relative to the bridge tube 94 while substantially preventing leakage at each interface between the bridge tube 94 and a balloon 90, 92.

The second balloon 92 of the dual auto-perfuser 80 may be substantially hollow to allow for the flow of blood therethrough. Alternately, a tube (not shown) extends between opposite sides of the second balloon 92 and connects to the bridge tube 94, to allow for blood flow through the tube across the second balloon 92. An exit tube 96 is connected to the second balloon 92, through which blood flows and exits the dual auto-perfuser 80.

To begin the procedure, the patient is placed on a cardiopulmonary bypass pump, the heart is stopped, and clamps are placed on the aorta 60 spaced apart from the ascending aorta. Incisions 62 are made in the aorta 60 to separate the ascending aorta, and the ascending aorta is removed. The central section 22 of the aortic graft 20 is then sutured to the proximal end of the aortic stump 70 at or in proximity to the incision 62. In this way, the lumen of the central section 22 of the aortic graft 20 is easily accessible.

The dual auto-perfuser 80 is inserted through the lumen of the central section 22 of the aortic graft 20, through the hemostasis valve 32 and then the access port 30. The dual auto-perfuser 80 is advanced through the access port 30 until the first balloon 90 is located within the central section 22 of the aortic graft 20 in proximity to the open end of the central section 22 of the aortic graft 20; the second balloon 92 is then located outside the lumen of the central section 22 of the aortic graft 20. The first balloon 90 is then inflated.

The heart is then restarted and the patient removed from cardiopulmonary bypass according to standard practice. While the heart is being restarted, or prior to restarting the heart, the remainder 20a of the aortic graft 20 is inserted into the descending aorta 74; the second balloon 92 is inserted into the descending aorta 74 within the remainder 20a of the aortic graft, and the second balloon 92 is inflated. Autoperfusion is then initiated through the dual auto-perfuser 80. For example, the apertures 84 upstream are initially blocked, such as by a sliding tube, and then unblocked at a selected time to start autoperfusion such as by moving the sliding tube away from the apertures. Blood flows through the bridge tube 94 between the balloons 90, 92 to allow circulation through the aorta while the implantation of the aortic graft 20 is completed. Jumpers 40, 50 are selected, connected to the brachiocephalic trunk 64, left common carotid artery 66, and left subclavian artery 68, and anchored to the central section 22 of the aortic graft 20 substantially as described above with regard to FIG. 12. In this way, the amount of time that the patient is on cardiopulmonary bypass is reduced, with a corresponding reduction in patient side effects associated with cardiopulmonary bypass.

As needed, the remainder 20a of the aortic graft 20 may be sutured to the descending aorta 72 to ensure that remainder 20a of the aortic graft 20 remains in place. Alternately, such suturing need not be performed. The remainder 20a of the aortic graft 20 may be sutured or otherwise affixed to the central section 22 of the aortic graft 20. According to other embodiments, the remainder 20a of the aortic graft 20 is inserted into the descending aorta 74, and then the central section 22 is sutured to the descending aorta 74. With the remainder 20a of the aortic graft 20 secured, the balloons 90, 92 are deflated, and the dual auto-perfuser 80 is withdrawn through the hemostasis valve 32.

Figure 15:
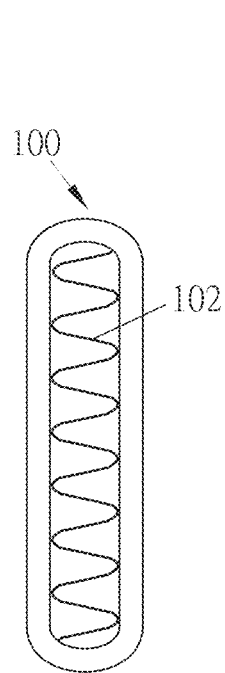
FIG. 15 is a side view of a floating suture ring in a first, normal state.
Figure 16:
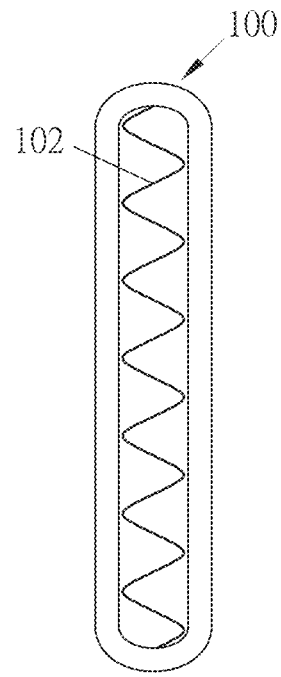
FIG. 16 is a side view of the floating suture ring of FIG. 15, in a second, expanded state.
Figure 17:
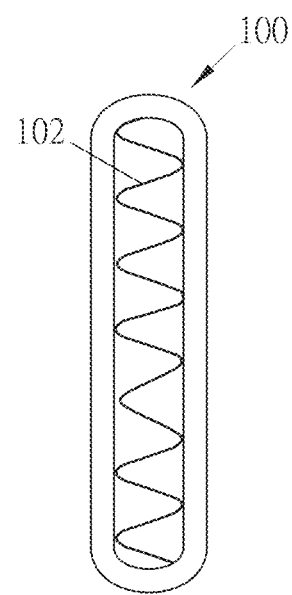
FIG. 17 is a side view of the floating suture ring of FIG. 16, in a third, adjusted state.
Figure 18:
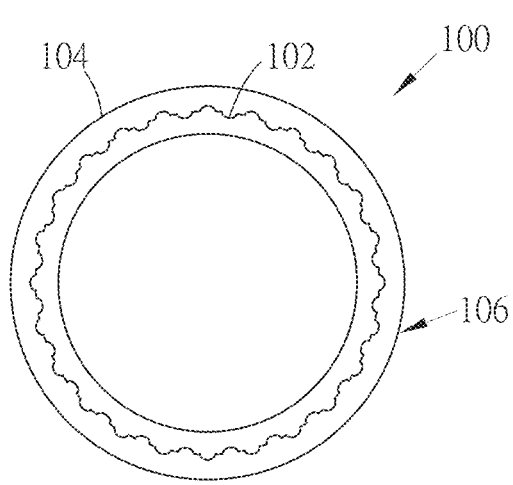
FIG. 18 is a front view of the floating suture ring of FIG. 17.
Figure 19:
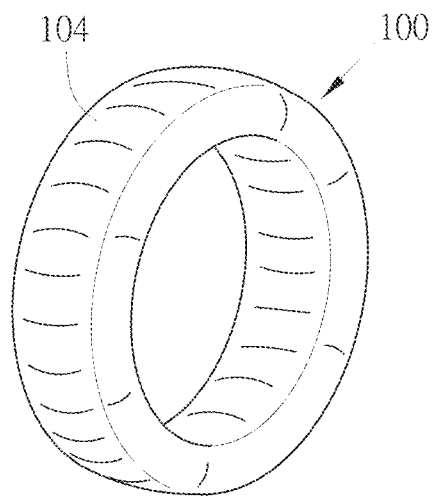
FIG. 19 is a perspective view of the floating suture ring of FIG. 15.

Referring to FIGS. 15-19, a floating suture ring 100 is shown. The floating suture ring 100 need not be perfectly circular, and may be curved in any other suitable manner. Referring to FIG. 15, the floating suture ring 100 is initially in a first state. The floating suture ring 100 includes a spring element 102 that assists in expansion of the floating suture ring 100 from the first state to the second state as shown in FIG. 16. The spring element 102 may be covered at least in part by a fabric cover 104. In some embodiments, the fabric cover may be a PET mesh, such as DACRON® brand polyester. The spring element 102 may be fabricated from a superelastic material such as nickel-titanium alloy, such that the exertion of a radial force on the spring element 102 causes that spring element 102 to transition between a martensite phase and an austentite phase, expanding to the second state. In other embodiments, the spring element 102 may be fabricated from an elastic material, such as stainless steel, that is initially compressed in the first state and then self-expands to the second state, or that is plastically deformed to transition from the first state to the second state. The spring element 102 may be generally circular, or may have any other suitable shape. Referring to FIGS. 17-18, the floating suture ring 100 optionally may include an adjustable section 106. The adjustable section 106 may be a corrugation or accordion-shaped section of the spring element 102 that is manually adjustable, or other configuration that is manually-adjustable. The adjustable section 106 optionally is fabricated from a different material than the remainder of the spring element 102 and attached to the spring element 102. The adjustable section 106 allows for a manual adjustment of fit in the patient, as described in greater detail below. FIG. 19 shows the floating suture ring 100 of FIG. 15 in the first state in a perspective view.

Figure 20:
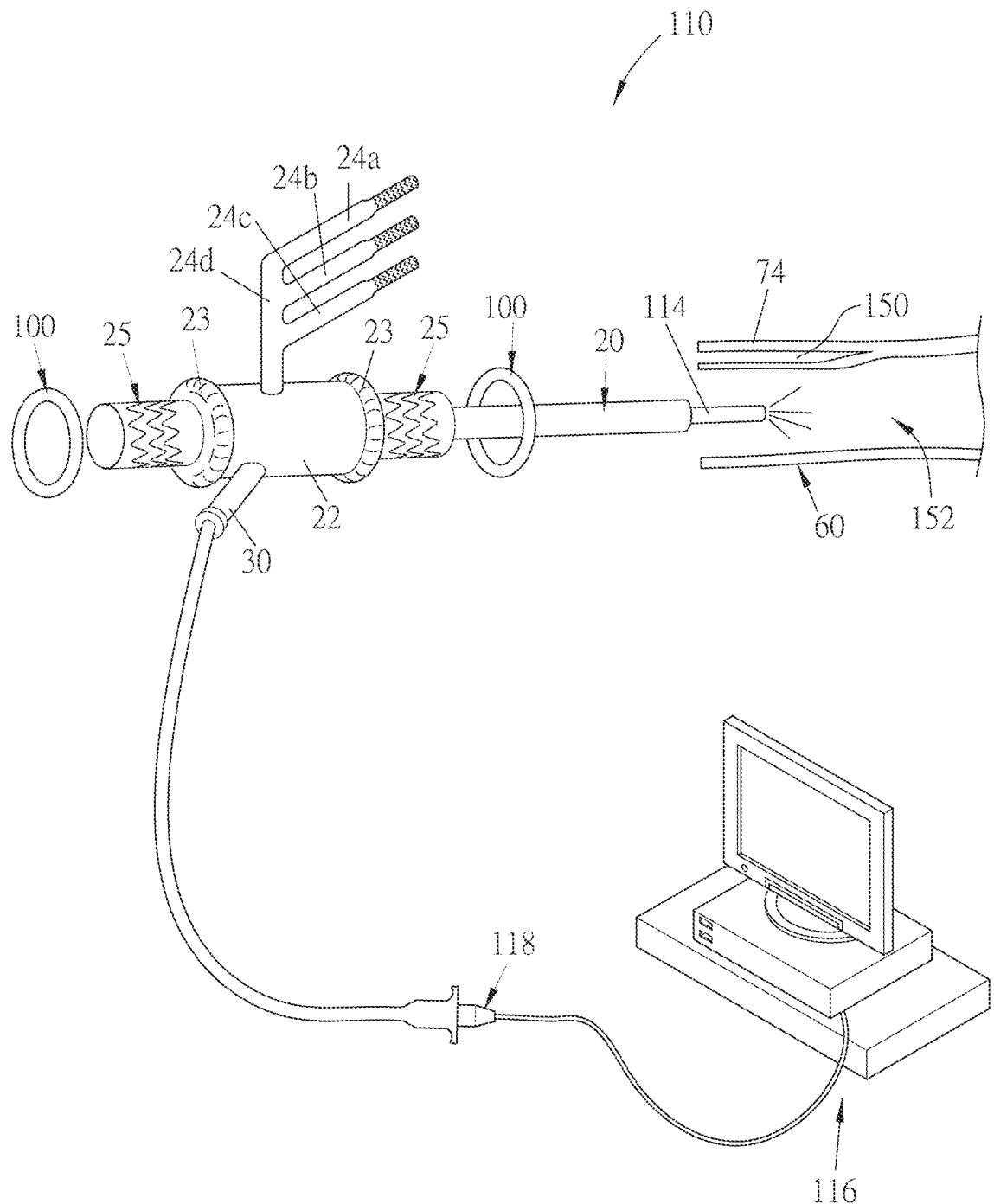
FIG. 20 is a perspective view of an exemplary system for implantation of an aortic graft.
Figure 21:
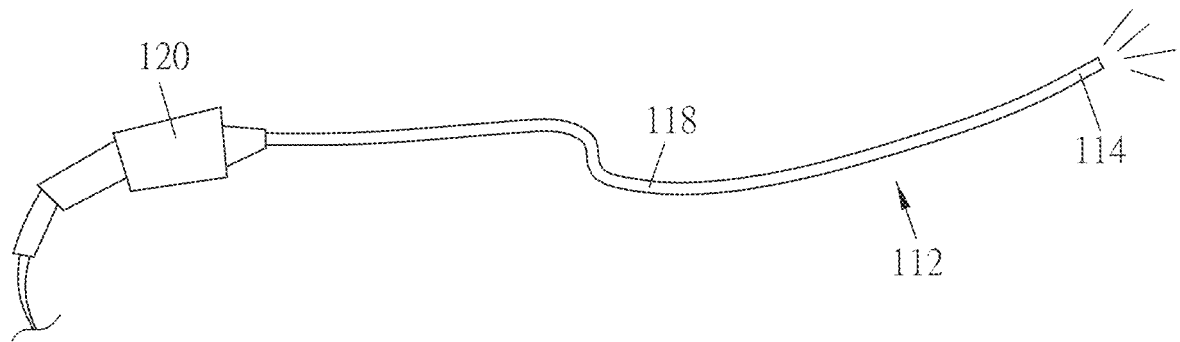
FIG. 21 is a perspective view of a flexible endoscope system.

Referring to FIG. 20, a system 110 for implanting an aortic graft 20 is shown. The aortic graft 20 implanted with the system 110 may be any of the aortic grafts 20 as described above. The aortic graft 20 may include a central section 22 that includes an access port 30, at least one suture band 23, and at least one central section anchor 25, as described above such as in regard to FIG. 6A. One or more jumper grafts may extend from the central section 22, or a single manifold 24d may extend from the central section 22, with one or more jumper grafts 24a, 24b, 24c extending therefrom. One or more floating suture rings 100 may be included in the system 100 in association with the aortic graft 20. Referring also to FIG. 21, a flexible endoscope system 112 may extend through the access port 30 and out of an end of the aortic graft 20. The flexible endoscope system 112 may include a visualization head 114 at the end of a flexible scope body 118 that includes a light and camera, and such a visualization head 114 may be configured as known in the art. A camera 120 may be located proximal to and spaced apart from the visualization head 114, such that the visualization head 114 includes one or more lenses that pass images along the scope body 118 to the camera 120 for resolution. The flexible endoscope system 112 also may be connected to a console 116 that displays to the user the view from the visualization head 114; such a console is known in the art. Optionally, the flexible endoscope system 112 may be inserted into the patient through a trocar 118, as is standard.

Figure 22:
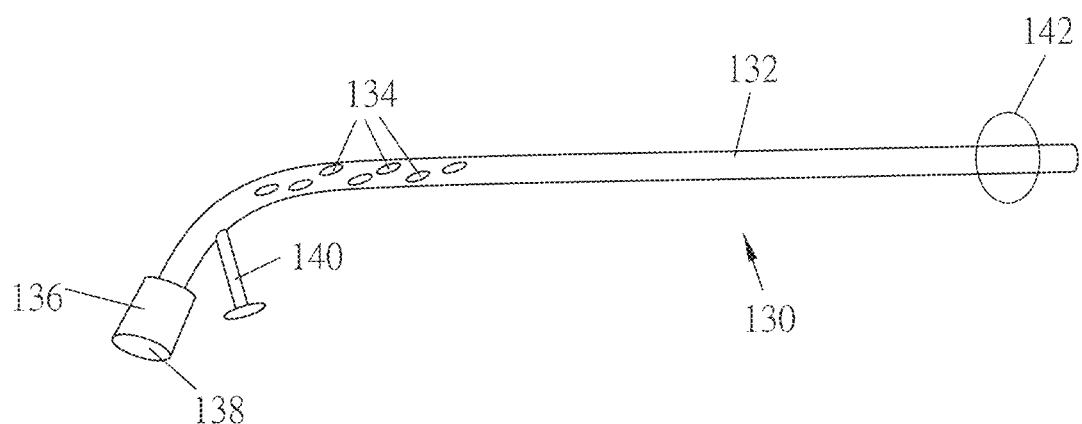
FIG. 22 is a perspective view of a single perfusion catheter.
Figure 23:
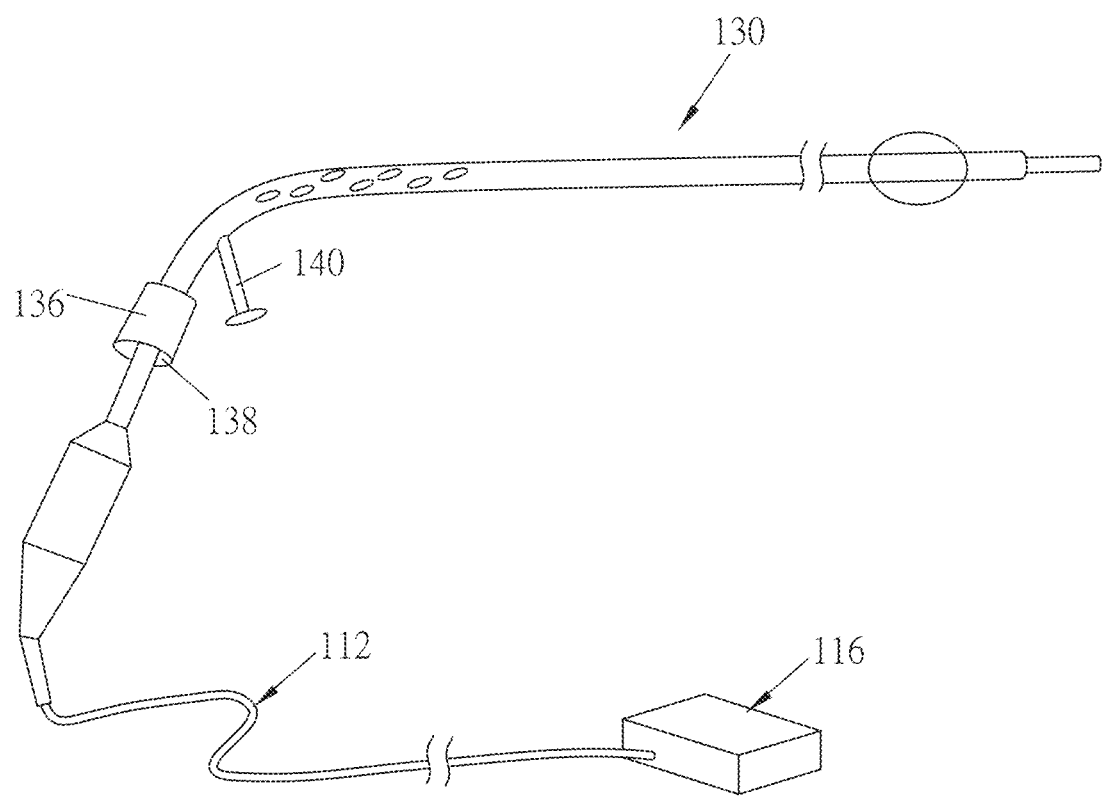
FIG. 23 is a perspective view of the flexible endoscope system of FIG. 21 inserted into the single perfusion catheter of FIG. 22.

Referring to FIGS. 20 and 22, a single perfusion catheter 130 is shown. The single perfusion catheter 130 defines a lumen within a catheter sheath 132. At or in proximity to the distal end of the catheter sheath 132 is an occlusion balloon 142 inflatable to an inflated state and deflatable to a deflated state. Proximal to the occlusion balloon 12 one or more perfusion ports 134 extend through the catheter sheath 132 to the lumen. A balloon infusion port 140 is located proximal to the perfusion port or ports 134, and allows for inflation of the occlusion balloon 12. At the proximal end of the catheter sheath 132, a hub 136 and seal 138 close the end of the single perfusion catheter 130 while allowing passage of tools therethrough, as is standard. FIG. 23 shows the flexible endoscopic system 112 inserted through the hub 136 and seal 138 through the single perfusion catheter 130, with the distal end of the flexible endoscope system 112 extending out of the distal end of the single perfusion catheter 130.

Referring to FIG. 20, the system 110 is used to place an aortic graft 20 in a patient. Such implantation is generally performed as described above, with particular changes described here. The system 110 assists the clinician in avoiding complications from inadvertent insertion of the aortic graft 20 into a false lumen 150 in the descending aorta 74. A dissection occurs when a tear of the intima of the aorta 60 allows blood to leak into the media. This creates two passages for blood: a true lumen 152, which is the normal passageway of blood, and a false lumen 150, the newly created passageway. If the aortic graft 20 is inserted into the false lumen 150, severe complications may result.

Figure 24:
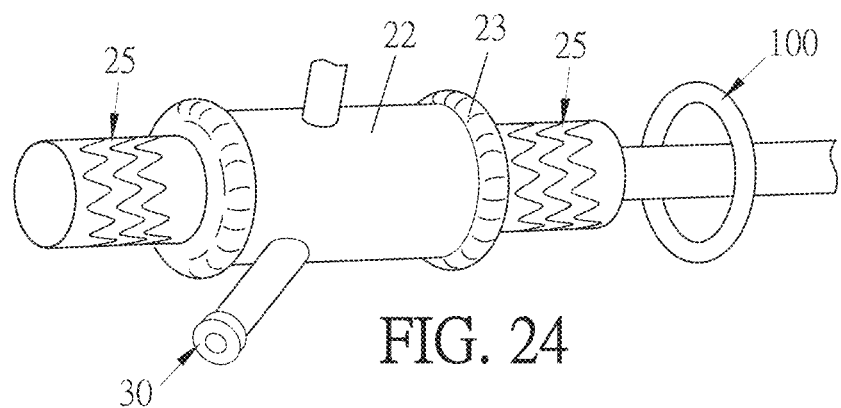
FIG. 24 is a perspective view of a step in the operation of the system of FIG. 20.

Referring also to FIG. 24, a floating suture ring 100 is slid over the end of each remaining portion of the aorta 74. The proximal end of the aortic graft 20 may be attached to the aortic stump 70, as described above. After the proximal central section anchor 25 is sutured to the aortic stump 70, the proximal floating suture ring 100 is slid toward the central section 22, over the proximal central section anchor 25. This compresses the aortic wall between the floating suture ring 100 and the proximal central section anchor 25. The proximal floating suture ring 100 may be expanded to its second state in order to allow it to slide over the proximal central section anchor 25. The adjustable section 106 of the proximal floating suture ring 100 may then be adjusted to tighten the floating suture ring 100, in the event the floating suture ring 100 is too loose in its expanded state. The proximal floating suture ring 100 is then sutured to the proximal central section anchor 25.

A portion of the combination of the flexible endoscopic system 112 and single perfusion catheter 130, as seen in FIG. 23, is inserted through the access port 30 of the central section 22 of the aortic graft 20. The distal end of the flexible endoscopic system 112 is then advanced into the descending aorta 74. The clinician utilizes the images from the flexible endoscopic system 112 to determine whether the distal end of the flexible endoscopic system 112 is located in the true lumen 152 or false lumen 150 of the descending aorta 74. If the distal end of the flexible endoscopic system 112 is located in the false lumen 150, the flexible endoscopic system 112 is withdrawn, and the clinician then advances it again and repeats the determination of the location of the distal end of the flexible endoscopic system 112. If the distal end of the flexible endoscopic system 112 is located in the true lumen 152, the process continues. The flexible endoscopic system 112 is withdrawn. The heart is then restarted and the patient removed from cardiopulmonary bypass according to standard practice. The jumper grafts 24a, 24b, 24c are connected to the patient's cerebral arteries, and blood flow to the brain is restored.

Figure 25:
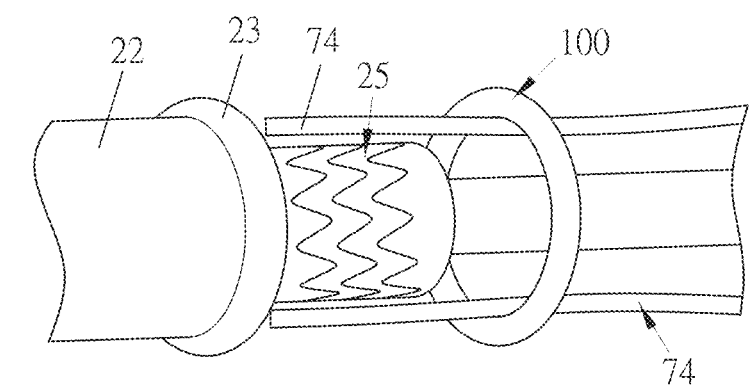
FIG. 25 is a perspective view of another step in the operation of the system of FIG. 20.
Figure 26:
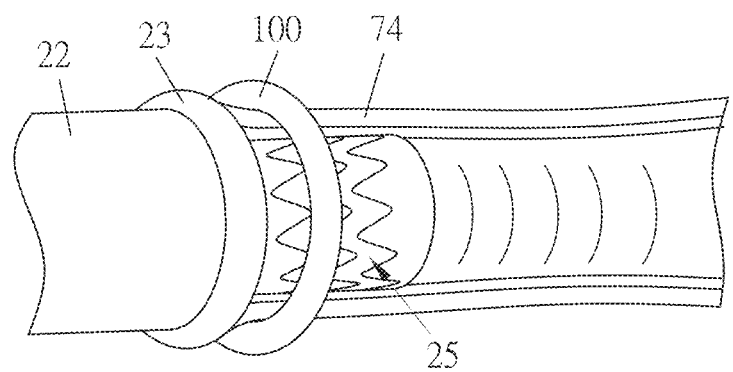
FIG. 26 is a perspective view of another step in the operation of the system of FIG. 20.

The distal end of the aortic graft 20 may be attached to the descending aorta 74, as described above. This instead may be performed before the jumper grafts 24a, 24b, 24c are connected to the cerebral arteries, at the option of the clinician. Referring also to FIG. 25, after the distal central section anchor 25 is sutured to a remainder of the aorta 74, the distal floating suture ring 100 is slid toward the central section 22, over the distal central section anchor 25. This compresses the aortic wall between the floating suture ring 100 and the distal central section anchor 25. The distal floating suture ring 100 may be expanded to its second state in order to allow it to slide over the distal central section anchor 25. The adjustable section 106 of the distal floating suture ring 100 may then be adjusted to tighten the floating suture ring 100, in the event the floating suture ring 100 is too loose in its expanded state. The distal floating suture ring 100 is then sutured to the distal central section anchor 25, as shown in FIG. 26.

Figure 58:
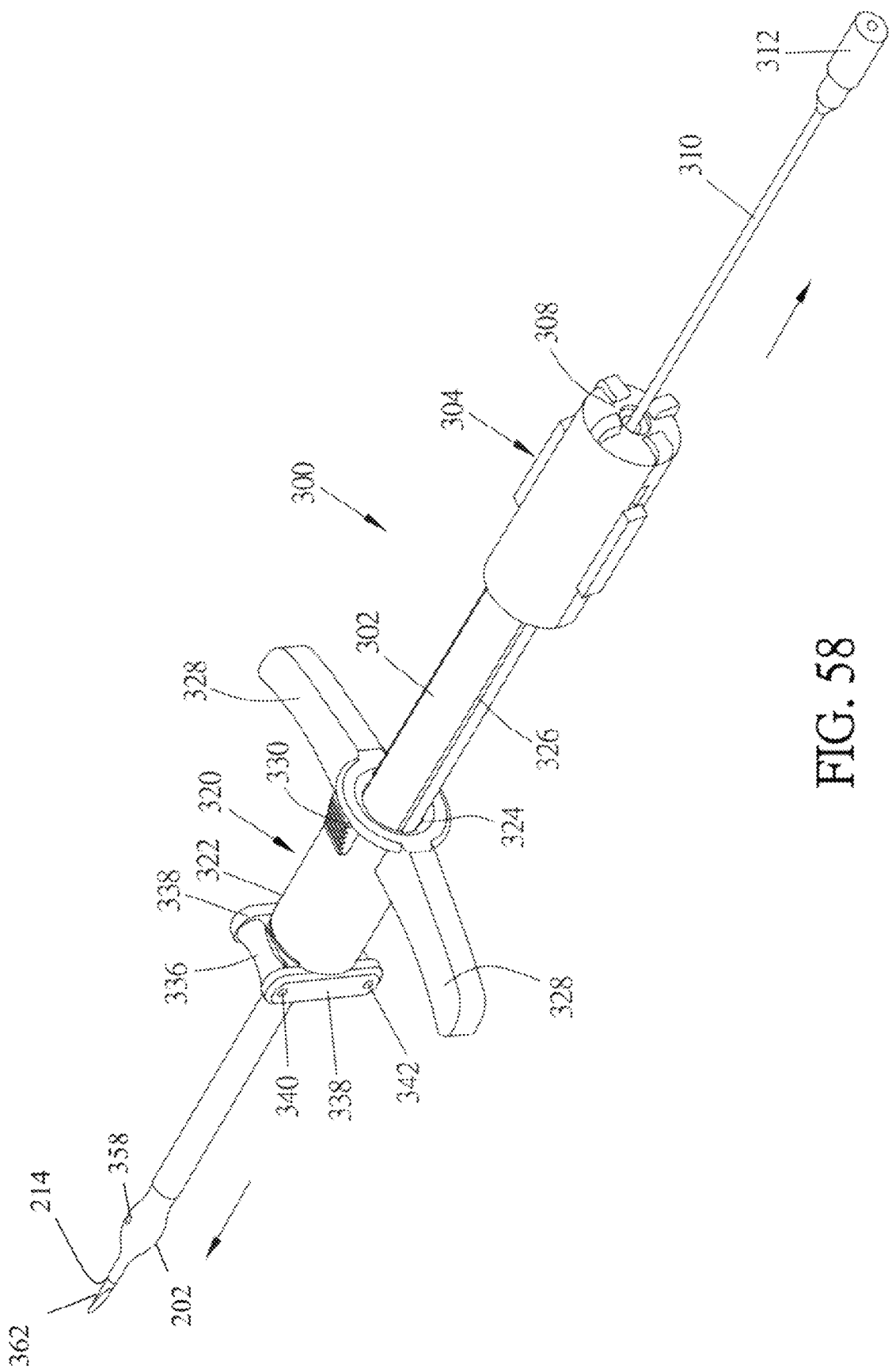
FIG. 58 is a perspective view of another embodiment of an exemplary deployment tool.
Figure 60:
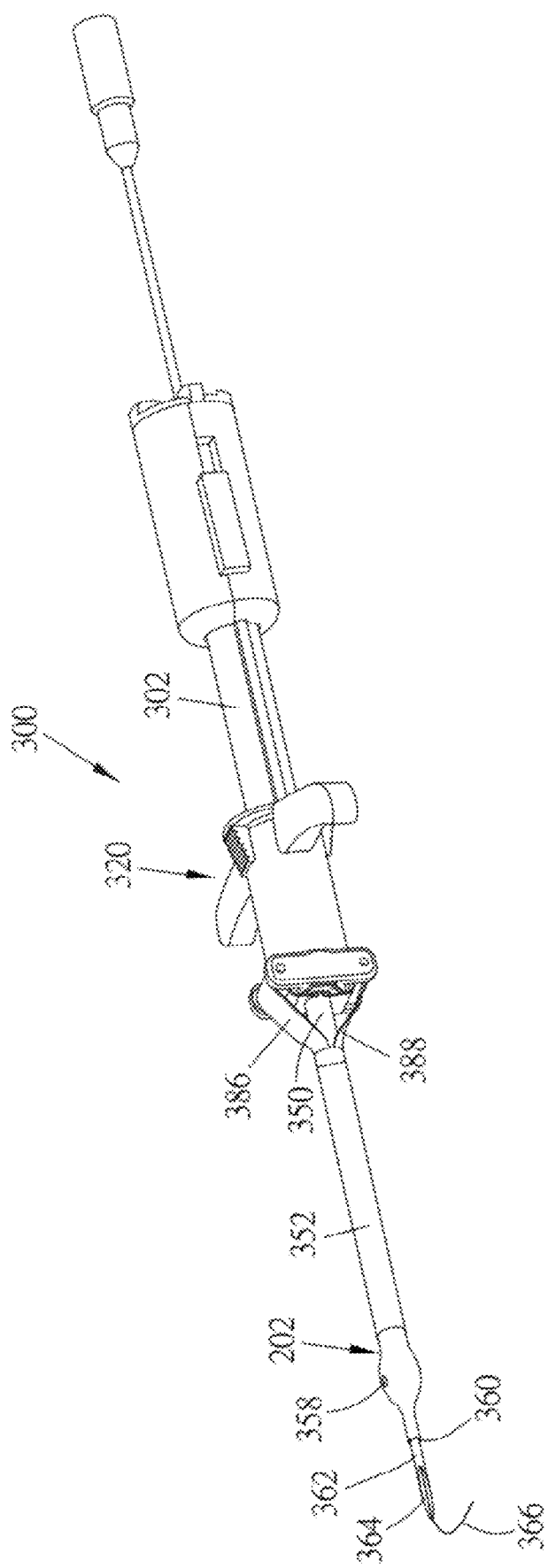
FIG. 60 is another perspective view of the exemplary deployment tool of FIG. 58.
Figure 73:
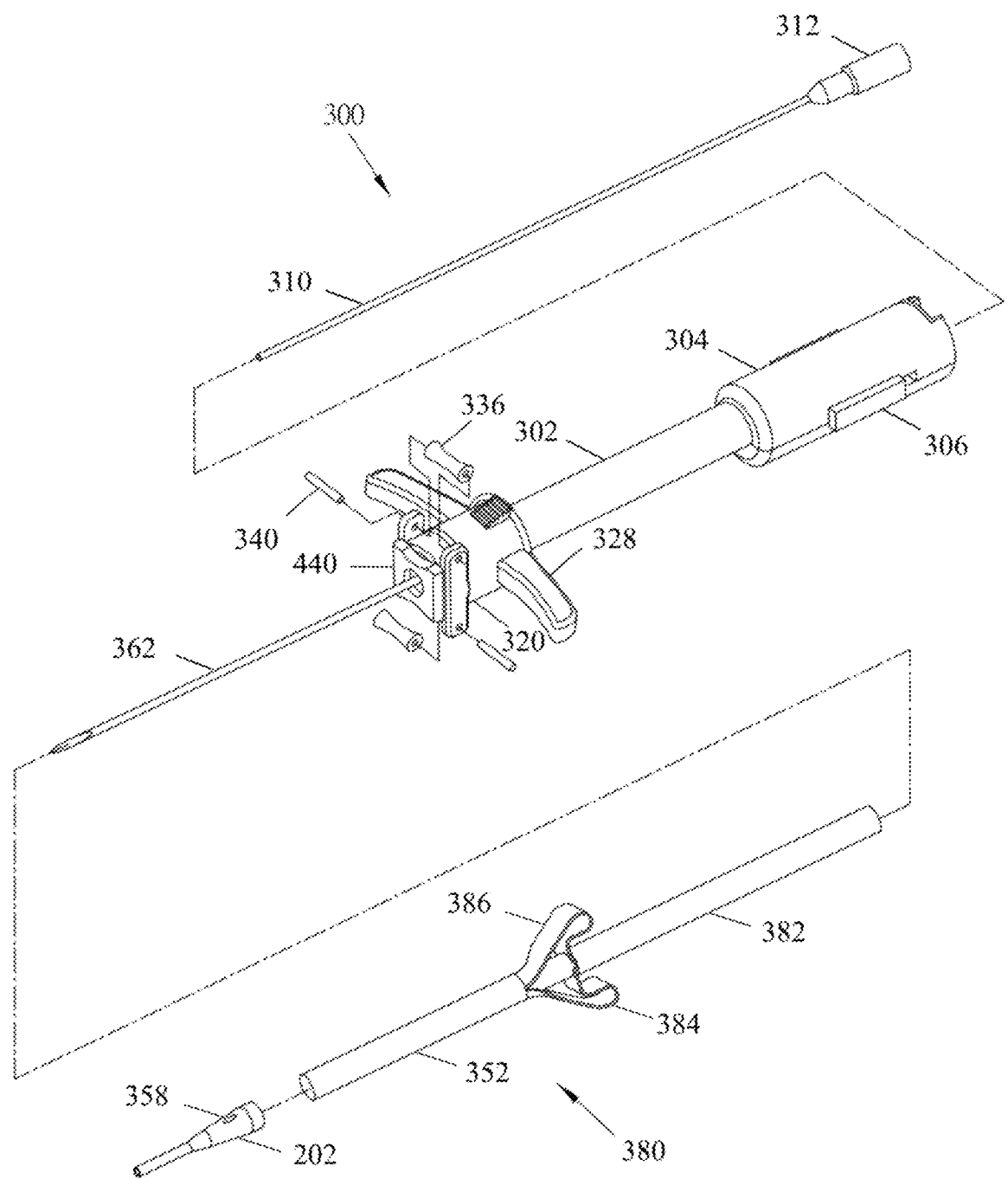
FIG. 73 is an exploded view of the exemplary deployment tool of FIG. 58.

Referring also to FIG. 58, another embodiment of an exemplary deployment tool 300 is shown. The deployment tool 300 includes a body 302 distal to and connected to a grip 304. The body 302 may be fabricated integrally with the grip 304, or may be fabricated separately from the grip 304 and later affixed thereto. The body 302 and the grip 304 advantageously are fixed longitudinally relative to one another. One or both of the body 302 and the grip 304 may be generally cylindrical in shape, or may have any other suitable shape. The grip 304 may include one or more ridges extending outward therefrom to facilitate handling of the grip 304 by a user. The grip 304 and the body 302 each may include a lumen 214 extending therethrough, where the lumen 214 extends proximally to an aperture 308 at the proximal end of the grip 304. The aperture 308 may be generally circular, or may have any other suitable shape. Referring also to FIGS. 60 and 73, a guidewire 310 may be received through the lumen 214 so that guidewire 310 is distally extendable out of the aperture 360 at the distal end of deployment tool 300, extending proximally from the aperture 308 to a guidewire grip 312. The guidewire 310 and the guidewire grip 312 are slidable longitudinally relative to the body 302 and the grip 304, as described in greater detail below.

A slider actuator 320 may be located distal to the grip 304. The slider actuator 320 may include a slider body 322 that is generally cylindrical. The slider body 322 may include a bore 324 defined therein that receives the distal end of the body 302. The body 302 may include at least one longitudinal groove 326 defined therein that engages a tab (not shown) on the slider body 322, such that the engagement between each longitudinal groove 326 and the corresponding tab constrains the body 302 and the bore 324 to substantially longitudinal movement relative to one another, and substantially prevents rotational motion between the body 302 and the bore 324. According to other embodiments, the longitudinal groove or grooves 326 and the corresponding tab(s) are omitted, and the body 302 and the bore 324 are free to rotate relative to one another. One or more arms 328 may extend radially outward from the slider body 322. As described in greater detail below, the arm or arms 328 may be grasped by a user at the same time as the grip 304, and the arm or arms 328 facilitate the user's operation of the slider actuator 320 relative to the grip 304. At least one ribbed region 330 optionally may be provided on the slider actuator 320. At least one ribbed region 330 may be located at a proximal end of the slider actuator 320. Alternately, at least one ribbed region 330 may be located at any other suitable location on the slider actuator 320. The at least one ribbed region 330 facilitates a user's grip on the slider actuator 320.

Figure 69:
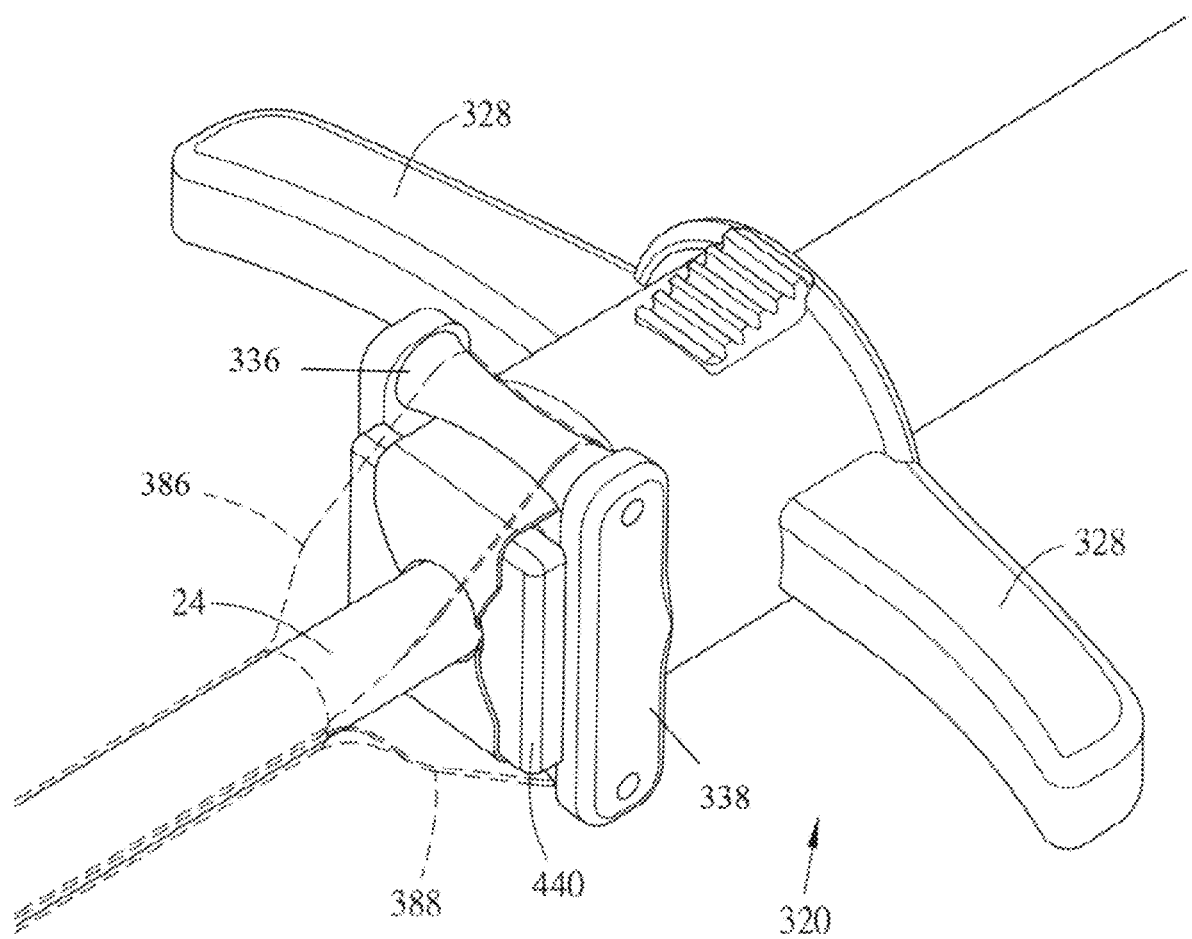
FIG. 69 is a detail view of the exemplary deployment tool of FIG. 68.

According to an exemplary embodiment, two or more rollers 336 may be located at the distal end of the slider actuator 320. Alternately, one or more rollers 336 may be positioned at a different longitudinal location on the slider actuator 320. The rollers 336 may be oriented substantially perpendicular to the longitudinal axis of the deployment tool 300, and oriented substantially parallel to one another. Roller frames 338 may extend from the slider actuator 320, such that each roller 336 is held between two roller frames 338 and is rotatable relative to those roller frames 338. Each roller 338 may include a pin 340 at an end thereof, and each pin 340 may be received in a corresponding aperture 342 in a roller frame 338. The roller frames 338 receive the rollers 336 and position the rollers 336 at a location spaced apart from the slider body 322. As described in greater detail below, a portion of a containment sheath is held by each roller 336. Referring also to FIG. 69, a flange 440 is located distal to the rollers 336, and the flange 440 is affixed to or integral with the body 302. The flange 440 may be located at the distal end of the body 302. As one example, the flange 440 may be substantially square in shape. As another example, the flange 440 may be substantially I-shaped, with each top and bottom horizontal segment of the I being distal to and substantially parallel to the corresponding roller frame 338.

Figure 59:
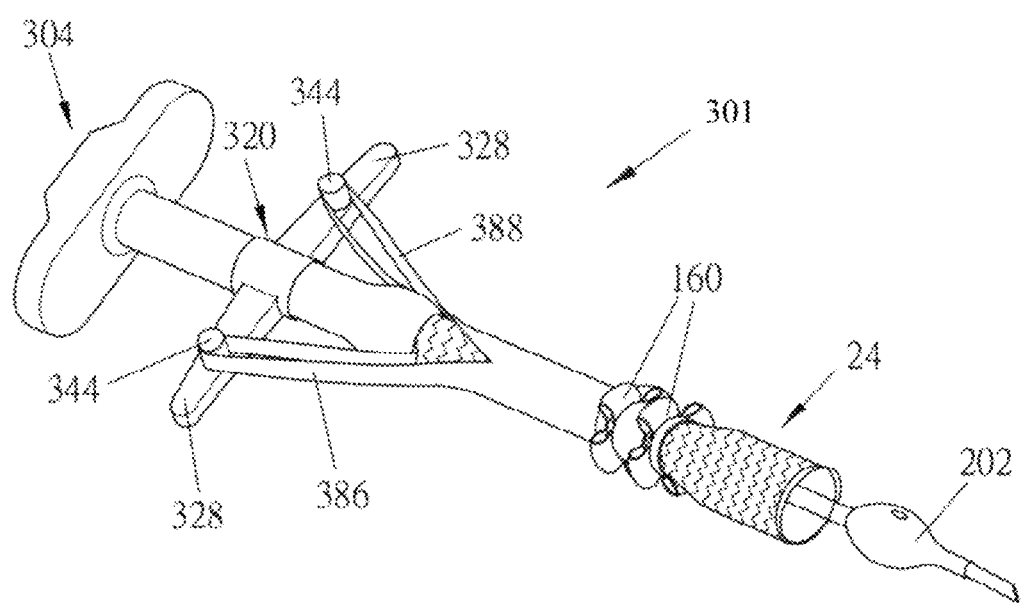
FIG. 59 is a perspective view of another embodiment of an exemplary deployment tool.

According to another exemplary embodiment, referring also to deployment tool 301 as depicted in FIG. 59, the rollers 336 may be omitted. In this embodiment, each arm 328 of the slider actuator 320 includes a peg 344 extending therefrom. At least one peg 344 may extend substantially at a right angle to the corresponding arm 328. Alternately, each peg 344 may be oriented at any other suitable angle relative to the corresponding arm 328. Each peg 344 may be affixed to the corresponding arm 328. In this way, the use of fixed pegs 344 may simplify fabrication of the deployment tool 301 relative to the fabrication of a deployment tool 300 that includes rotatable rollers 336. As described in greater detail below, a portion of a containment sheath is held by each peg 344.

Referring also to FIG. 60, the deployment tool 300 includes a mandrel 350 distal to and connected to the body 302, and deployment tool 301 may be similarly configured. The mandrel 350 may be fabricated integrally with the body 302, or may be fabricated separately from the body 302 and later affixed thereto. The body 302 and the mandrel 350 advantageously are fixed longitudinally relative to one another. The mandrel 350 may extend through and hold a vascular graft 24, as described in greater detail below. Because the mandrel 350 is fixed longitudinally relative to the body 302, the slider actuator 320 is slidable longitudinally relative to the mandrel 350.

Figure 61:
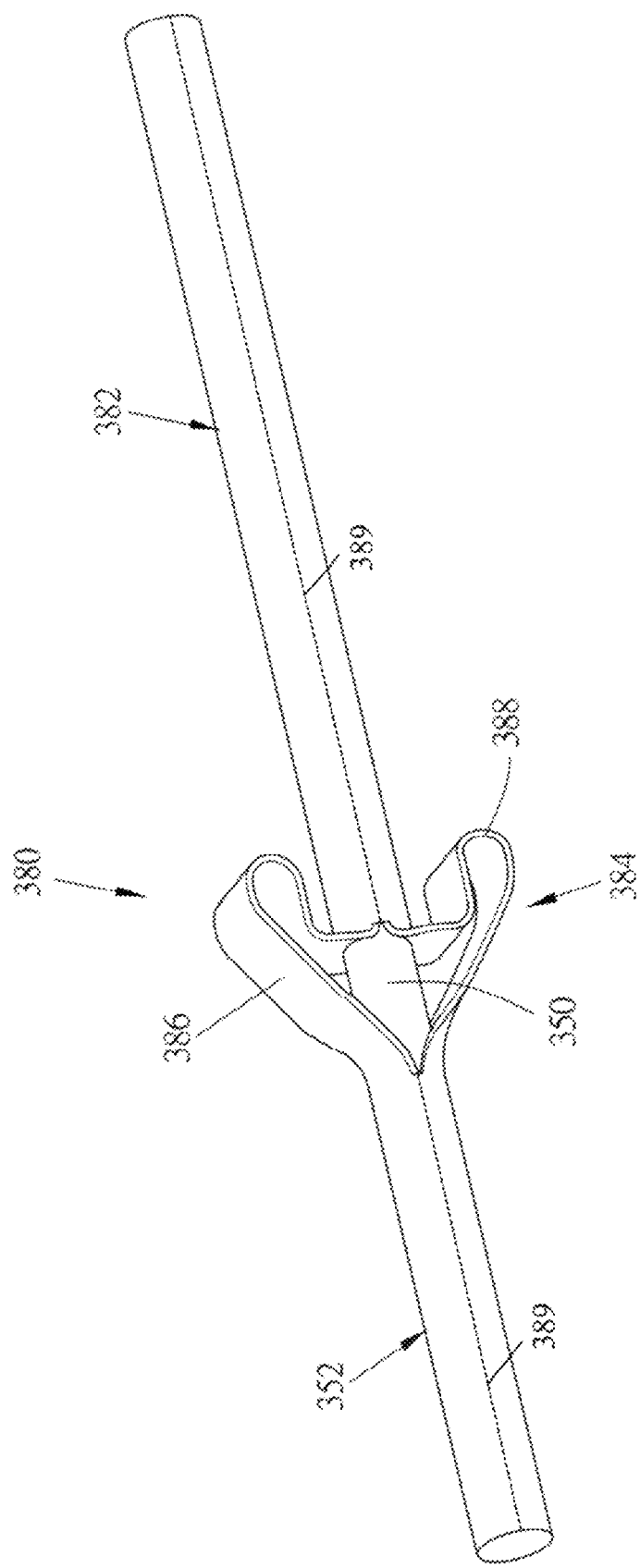
FIG. 61 is a perspective view of an exemplary sheath assembly that may be utilized in various embodiments of the deployment tool.

Referring also to FIG. 61, a sheath assembly 380 is shown. The sheath assembly 380 may include a distal sheath 352 and a proximal sheath 382, each of which is configured to surround and compress a different vascular graft 24. The distal sheath 352 and the proximal sheath 382 each are positioned over the mandrel 350, and each of the distal sheath 352 and the proximal sheath 382 compresses a vascular graft 24 (not shown in this view for the sake of clarity) against the mandrel 350. The vascular graft 24 may extend along the sheath assembly 380 from a location near the distal end of the distal sheath 352 to a location near the proximal end of the proximal sheath 382. As with other embodiments described above, the sheath assembly 380 may be fabricated from any suitable biocompatible material, such as but not limited to polytetrafluoroethylene (PTFE) or a polyester such as polyethylene terephthalate (PET), sometimes known as DACRON® brand polyester available from E. I. Du Pont De Nemours and Company of Wilmington, Delaware. Referring also to FIG. 73, an exploded view is shown to illustrate guidewire 310 extending through deployment tool 300, needle 362 and sheath assembly 380. The distal sheath 352 may be spaced apart longitudinally from the proximal sheath 382. The sheath assembly 380 may include a center section 384 that spaces apart the distal sheath 352 and the proximal sheath 382. The center section 384 is pre-split, while each of the distal sheath 352 and the proximal sheath 382 is generally cylindrical and therefore substantially un-split. The center section 384 may include two ribbons, a top ribbon 386 and a bottom ribbon 388, each of which is generally flat beginning a short distance away from the corresponding distal sheath 352 or proximal sheath 382. Advantageously, the distal sheath 352 and the proximal sheath 382 may include one or more longitudinal separation lines 389, which are weakened lines in the sheaths along which it preferentially tears. The points where the ribbons 386, 388 join also concentrate tearing forces, encouraging the distal sheath 352 and the distal sheath 382 to split or otherwise separate at those locations. Each ribbon 386, 388 is looped about a corresponding roller 336, referring also to FIG. 58 and deployment tool 300. Alternately, according to other embodiments, each ribbon 386, 388 may be wrapped around and/or affixed to a corresponding peg 344 on an arm 328 of the slider actuator 320, referring also to FIG. 59 and deployment tool 301. As described in greater detail below, such engagement between the ribbons 386, 388 and the rollers 336, or the pegs 344, causes the distal sheath 352 and/or the proximal sheath 382 to split and release the corresponding jumper grafts 24 during actuation of slider actuator 320.

Figure 62:
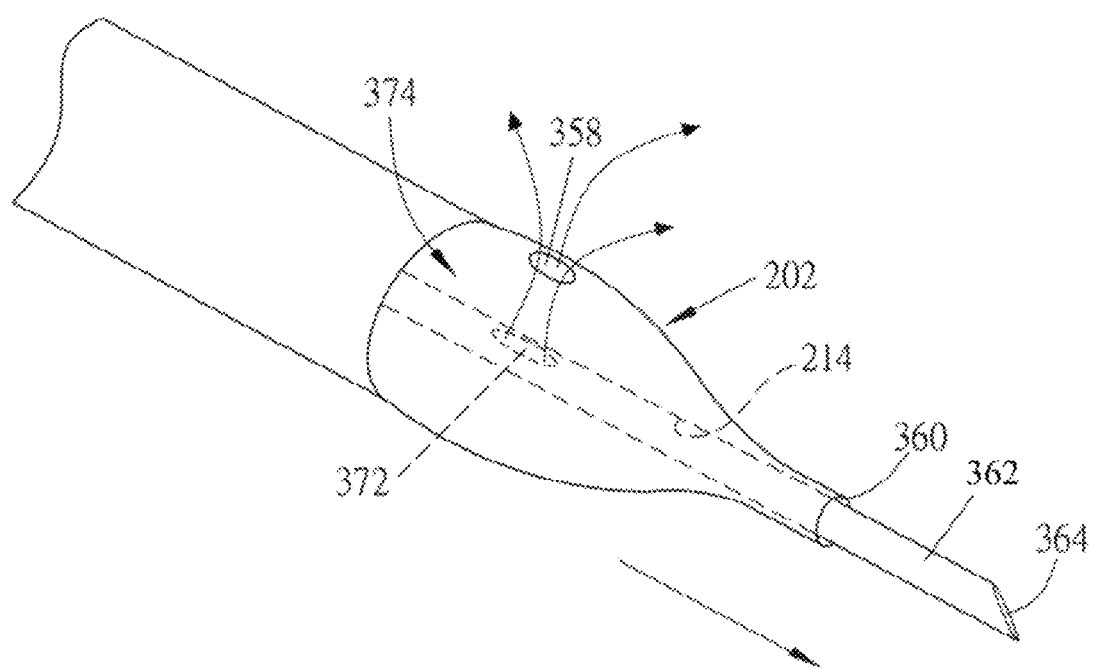
FIG. 62 is a perspective view of the distal end of an exemplary deployment tool, such as the deployment tool of FIGS. 58 and 59, including a hidden view of the interior of the distal end.

Referring also to FIGS. 60 and 62, the distal end of the mandrel 350 may include a dilator tip 202. The lumen 214 extends substantially longitudinally through the dilator tip 202. The dilator tip 202 may include at least one dilator tip bleedback port 358 defined through an outer surface thereof, extending to the lumen 214 defined through the dilator tip 202. The dilator tip 202 may have a maximum diameter no greater than the diameter of the mandrel 350 proximal to the dilator tip 202. Alternately, the dilator tip 202 may have a maximum diameter greater than or less than the diameter of the mandrel 350 proximal to the dilator tip 202. The dilator tip 202 may be tapered at its distal end, and an aperture 360 is located at its distal end, representing the distal end of the lumen defined through the dilator tip 202. Lumen 214 may extend substantially longitudinally through mandrel 350. A needle 362 is extendable distally outward from the aperture 360. As seen in FIGS. 60 and 62, the needle 362 is in the extended position. The needle 362 extends longitudinally at least partially through the lumen 214 of deployment tool 300 to the aperture 360. The needle 362 itself includes a lumen 364 defined longitudinally therethrough, open at the distal end of the needle 362. Referring also to FIG. 62, the needle 362 also may include a needle bleedback port 372 defined through a wall thereof at a location spaced apart from the distal end of the needle 362, allowing fluid to flow into the needle 362 from the distal end of the needle 362, through the lumen 364, and out of the needle 362 through the needle bleedback port 372. The dilator tip 202 may include a hollow plenum 374 defined therein. Alternately, the dilator tip 202 may include a tunnel, passage, or other smaller space through which fluid can flow. When the needle bleedback port 372 is located in or adjacent to the plenum 374 or other space (such as a tunnel or passage in the dilator tip 202), blood can flow into the needle 362 from the distal end of the needle 362, through the lumen 364, out of the needle 362 through the needle bleedback port 372, into the plenum 374 or other space in the dilator tip 202, and then out of the dilator tip bleedback port 358. As described in greater detail below, such flow of blood out of the dilator tip bleedback port 358 is useful to confirm the presence of the distal end of the needle 362 in the true lumen of the blood vessel to be treated.

The lumen 364 of the needle 362 receives the guidewire 310 therein. Referring also to FIGS. 58 and 73, the guidewire 310 may be fed into the deployment tool 300 through a guidewire aperture 308 in the grip 304.

Figure 72:
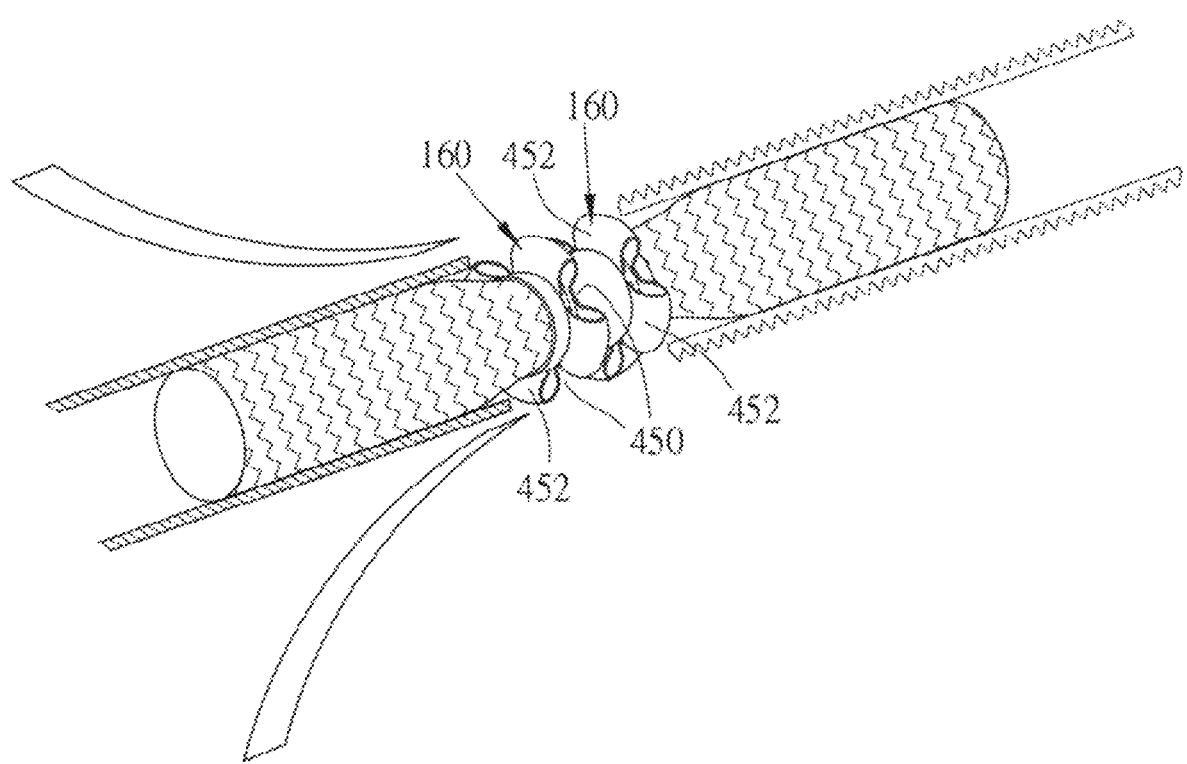
FIG. 72 is a perspective view of a deployed vascular graft that includes two exemplary suture cuffs.
Figure 83:
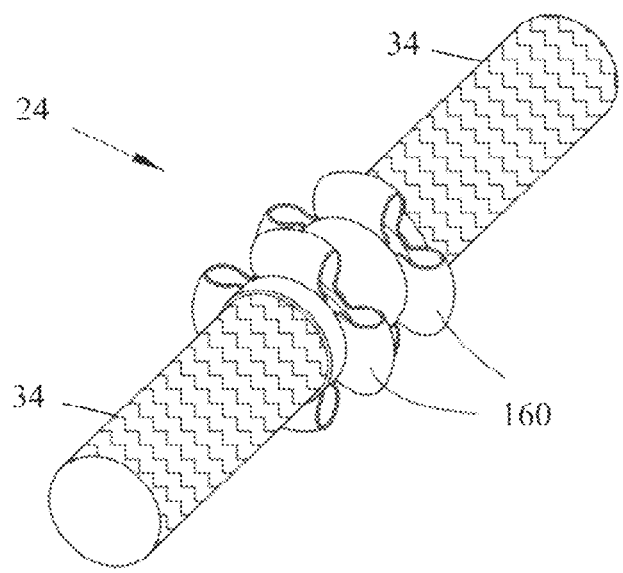
FIG. 83 is a perspective view of an exemplary vascular graft with two suture cuffs.
Figure 84:
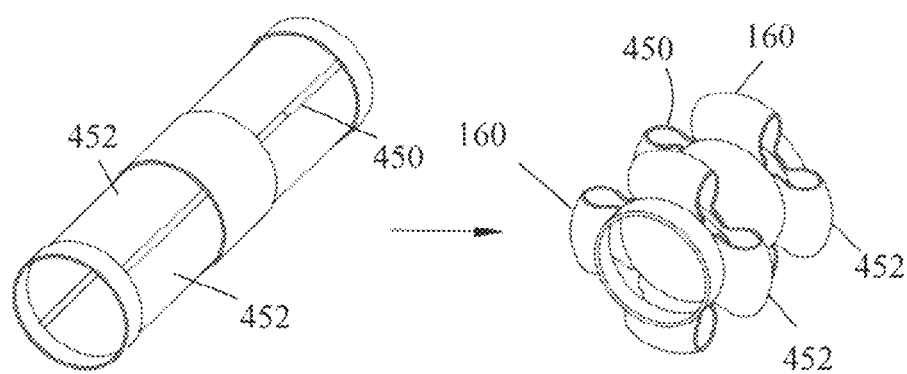
FIG. 84 is a detail view of the vascular graft of FIG. 83 schematically depicting the formation of lobes of the suture cuffs.

Referring also to FIG. 59, the vascular graft 24 may include at least two suture cuffs 160 substantially as described earlier in this document. Optionally, at least one of the suture cuffs 160 optionally may be fixed to the jumper graft 24, meaning that at least one of the suture cuffs 160 may be unable to be unrolled from the jumper graft 24. In this way, such one or more suture cuffs 160 may be utilized solely to provide the user with a larger thickness and volume of material to utilize to suture the vascular graft 24 to tissue. Alternately, at least one of the suture cuffs 160 may be capable of being unrolled to engage tissue, substantially as described earlier in this document. The vascular graft 24 including at least two suture cuffs 160 may be used with any suitable embodiment of deployment tool, such as but not limited to the deployment tool 300 of FIG. 58 or the deployment tool 301 of FIG. 59. The two suture cuffs 160 may be positioned closer to each other than either of the suture cuffs 160 is positioned relative to the ends of the vascular graft 24. Referring also to FIG. 83, the two suture cuffs 160 may be positioned near the longitudinal center of the vascular graft 24, and/or may be positioned each at substantially the same distance from the longitudinal center of the vascular graft 24. As discussed above, at least the ends of vascular graft 24 may be formed from expandable mesh 34 Alternately, at least one suture cuff 160 may be positioned at a different location on the vascular graft 24. As with the jumper grafts 24 described above, the vascular graft 24 that includes at least two suture cuffs 160 is wrapped about the mandrel 350, and at least part of the jumper graft 24 is compressed against the mandrel 350 by the distal sheath 352 or other embodiments of the sheath as described earlier in this document. Referring also to FIG. 72, according to other embodiments, at least one suture cuff 160 may be self-expandable. The vascular graft 24 may include longitudinal slits 450 defined therein, such that self-expansion of the vascular graft 24 upon removal of a constraining sheath causes the material located circumferentially between circumferentially-adjacent slits 450 to expand outward to form lobes 452. The lobes 452 collectively form a suture cuff 160 to which a user can suture. Alternately, the vascular graft 24 is compressed longitudinally to cause the lobes 452 to form. According to some embodiments, at least two slits 450 are defined in the vascular graft 24 per suture cuff 160, such that at least two lobes 452 are formed. According to other embodiments, four slits 450 are defined in the vascular graft 24 per suture cuff 160, such that four lobes 452 are formed. Referring also to FIG. 84, the formation of lobes 452 that constitute suture cuffs 160 is schematically shown as the assembly transitions from a compressed configuration to an expanded configuration.

Figure 78:
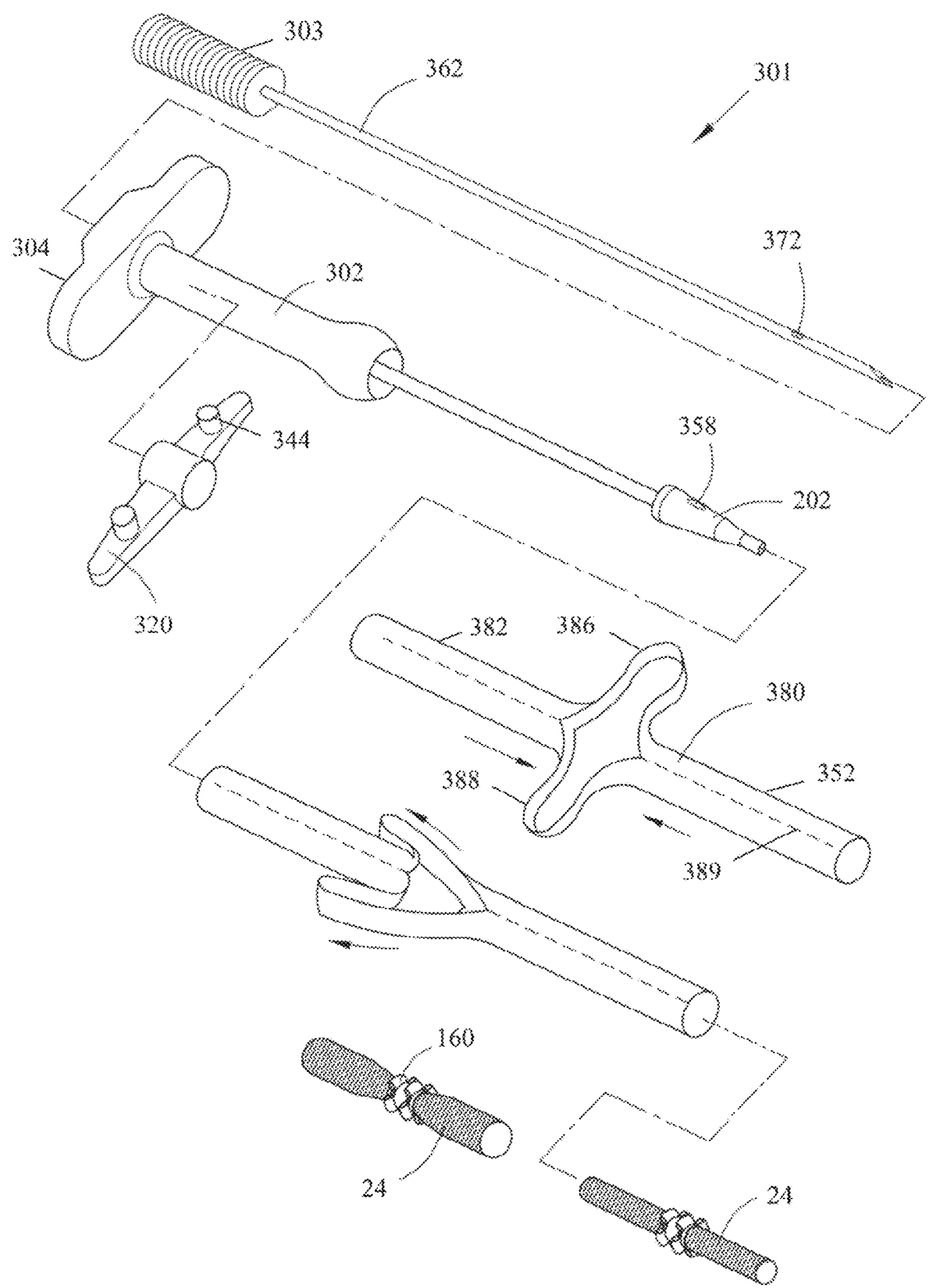
FIG. 78 is an exploded view of the exemplary deployment tool of FIG. 59.

Referring also to FIG. 78, an exploded view of the assembly of the deployment tool 301 of FIG. 59, sheath 380 and vascular graft 24 is shown. As indicated, needle 362 may extend coaxially through grip 304 and body 302 of deployment tool 301 so that needle 362 can protrude from dilator tip 202, and may be configured to be extended and retracted manually. For example, a needle grip 303 may be provided at the proximal end of needle 362 to facilitate manipulation. As desired, an aperture in needle grip 303 may receive a guidewire to be advanced through needle 362 and out its distal tip similar to embodiments described elsewhere. Sheath assembly 380, including proximal sheath 382 and distal sheath 352 may be disposed over deployment tool 301, with ribbons 386, 388 forming loops to engage with pegs 344 of slider actuator 320. Corresponding to the disclosures of this document, vascular graft, which may include suture cuffs 160, is constrained against mandrel 350 of deployment tool 301 by sheath 380, so that when freed by splitting sheath along separation lines 389, vascular graft 24 can assume its expanded configuration.

Figure 63:
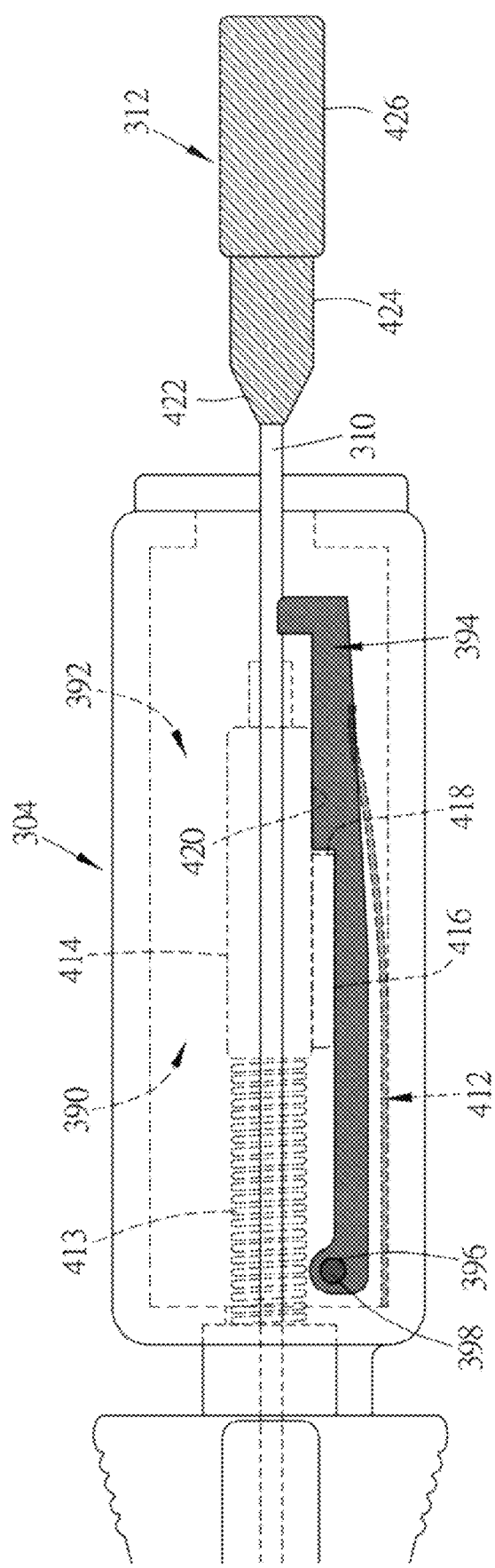
FIG. 63 is a side cutaway view of a needle retraction assembly within a grip that is utilized in various embodiments of the deployment tool, where the needle retraction assembly is in a latched state.
Figure 64:
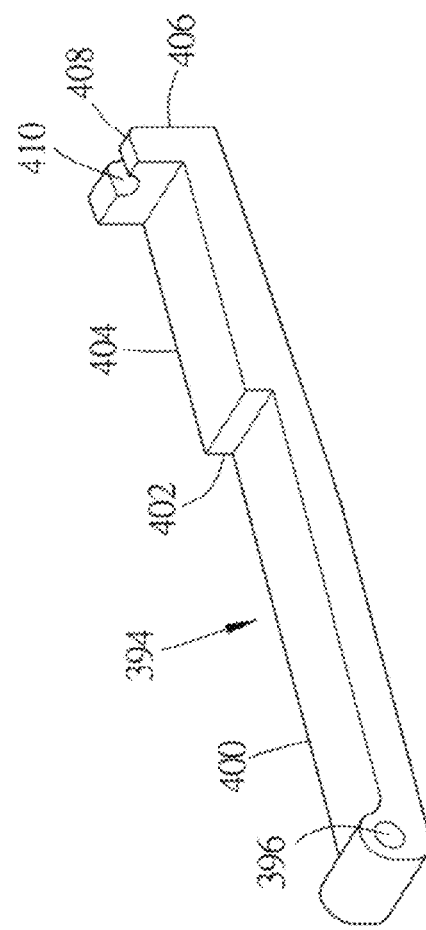
FIG. 64 is a perspective detail view of a latch used in the needle retraction assembly of FIG. 63.

Referring also to FIG. 63, the grip 304 of deployment tool 300 may include a needle retraction assembly 390 in a space 392 defined within the grip 304. Referring also to FIG. 64, the needle retraction assembly 390 includes a latch 394 that is pivotally attached to the grip 304. The latch 394 may include an aperture 396 defined laterally therethrough to receive an axle 398 therein, where the axle 398 is part of or is affixed to the grip 304. The latch 394 thereby is rotatable about the axle 398. Alternately, the aperture 396 does not extend completely through the latch, and two apertures are utilized, one on each side of the latch 394, where a separate axle extends into each aperture. The aperture 396 may be located in proximity to the distal end of the latch 394. The latch 394 may include a first surface 400 that is substantially flat, located proximal to the aperture 396. A catch 402 may extend upward from and substantially perpendicular to the proximal end of the first surface 400. The catch 402 also may be a substantially flat surface. The latch 394 may include a second surface 404 that is substantially flat and substantially perpendicular to the catch 402, located proximal to the catch 402. The proximal end of the latch 394 may include a tab 406 extending upward from and substantially perpendicular to the proximal end of the second surface 404. The upper end of the tab 406 may include a rounded corner 408 on its proximal edge. A rounded notch 410 may be defined substantially longitudinally in the upper surface of the tab 406 to accommodate the guidewire 310.

The needle retraction assembly 390 may include at least one leaf spring 412, where the distal end of the leaf spring 412 is fixed relative to the grip 304, and the proximal end of the leaf spring 412 is biased upward against the latch 394. Alternately, the leaf spring 412 may be otherwise mounted relative to the grip 304 in order to bias the proximal end of the leaf spring 412 upward against the latch 394. Alternately, at least one compression spring, other type of spring, or other structure or mechanism may be used to bias the proximal end of the leaf spring 412 upward against the latch 394.

The needle retraction assembly 390 may include a holdoff spring 413 attached to or abutting the front of the space within the grip 304. The holdoff spring 413 may be a compression spring, or any other suitable spring or mechanism. A holdoff block 414 may be affixed to or may abut the proximal end of the holdoff spring 413 and is coupled to needle 362 such that longitudinal movement of holdoff block 414 results in a corresponding longitudinal movement of needle 362 (not shown in this view). The holdoff block 414 may include a first surface 416 that is substantially flat, substantially parallel to the first surface 400 of the latch 394, and positioned substantially against the first surface 400 of the latch 394. The holdoff block 414 may include a holdoff block catch 418 extending upward from the proximal end of the first surface 416 that is substantially parallel to the first surface 400. The holdoff block catch 418 is distal to, and may be substantially parallel to and positioned substantially against, the catch 402 of the latch 394. The holdoff block 414 may include a second surface 420 that is substantially flat, substantially parallel to the second surface 404 of the latch 394, and positioned substantially against the second surface 404 of the latch 394. The holdoff block 414 includes a passage defined longitudinally therethrough to accommodate the guidewire 310, which is freely slidable relative to the holdoff block 414 through the passage. The holdoff spring 413 urges the holdoff block catch 418 against the catch 402 of the latch 394, and the leaf spring 412 urges the latch 394 into contact with the holdoff block 414. In this way, the needle retraction assembly 390 is in a latched state, and in the latched state the needle 362 is fixed to the holdoff block 414 and held in a fixed position.

Figure 65:
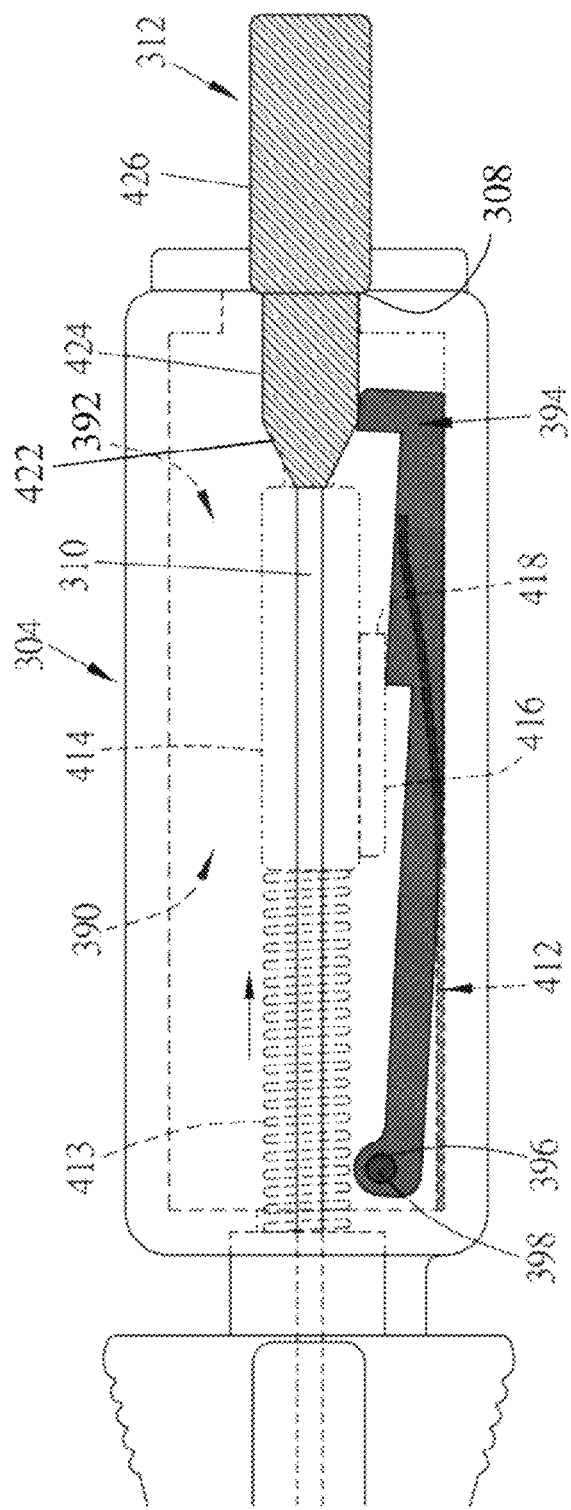
FIG. 65 is a side cutaway view of the needle retraction assembly of FIG. 63, where the needle retraction assembly is in an unlatched state.

Referring also to FIG. 65, in order to unlatch the needle 362, the guidewire grip 312 is advanced distally by the user. As the guidewire grip 312 advances, the guidewire 310 advances as well. The guidewire grip 312 may include a cam surface 422 at its distal end. As one example, the cam surface 422 of the guidewire grip 312 may be substantially frustoconical, as seen in FIG. 65, where the narrowest diameter of that frustoconical shape is at or near the distal end of the cam surface 422. As another example, the cam surface 422 may be an incline defined on the lower surface of the distal end of the guidewire grip 312, where the incline is closer to the guidewire 310 at its distal end than at its proximal end. The guidewire grip 312 additionally may include a narrower region 424 proximal to the cam surface 422, where the narrower region 424 has a diameter and/or cross-sectional area sized and shaped to be able to enter the aperture 308 in the grip 304. Alternately, the guidewire grip 312 does not include a narrower region 424, and only the cam surface 422 is sized and/or shaped to enter the aperture 308 in the grip 304. The guidewire grip 312 may include a wider region 426 that is sized and/or shaped such that it cannot enter the aperture 308 in the grip 304, and as a result the wider region 426 acts as a stop that prevents further distal motion of the guidewire grip 312 when the wider region 426 encounters the outer surface of the grip 304 adjacent to the aperture 308.

Figure 74:
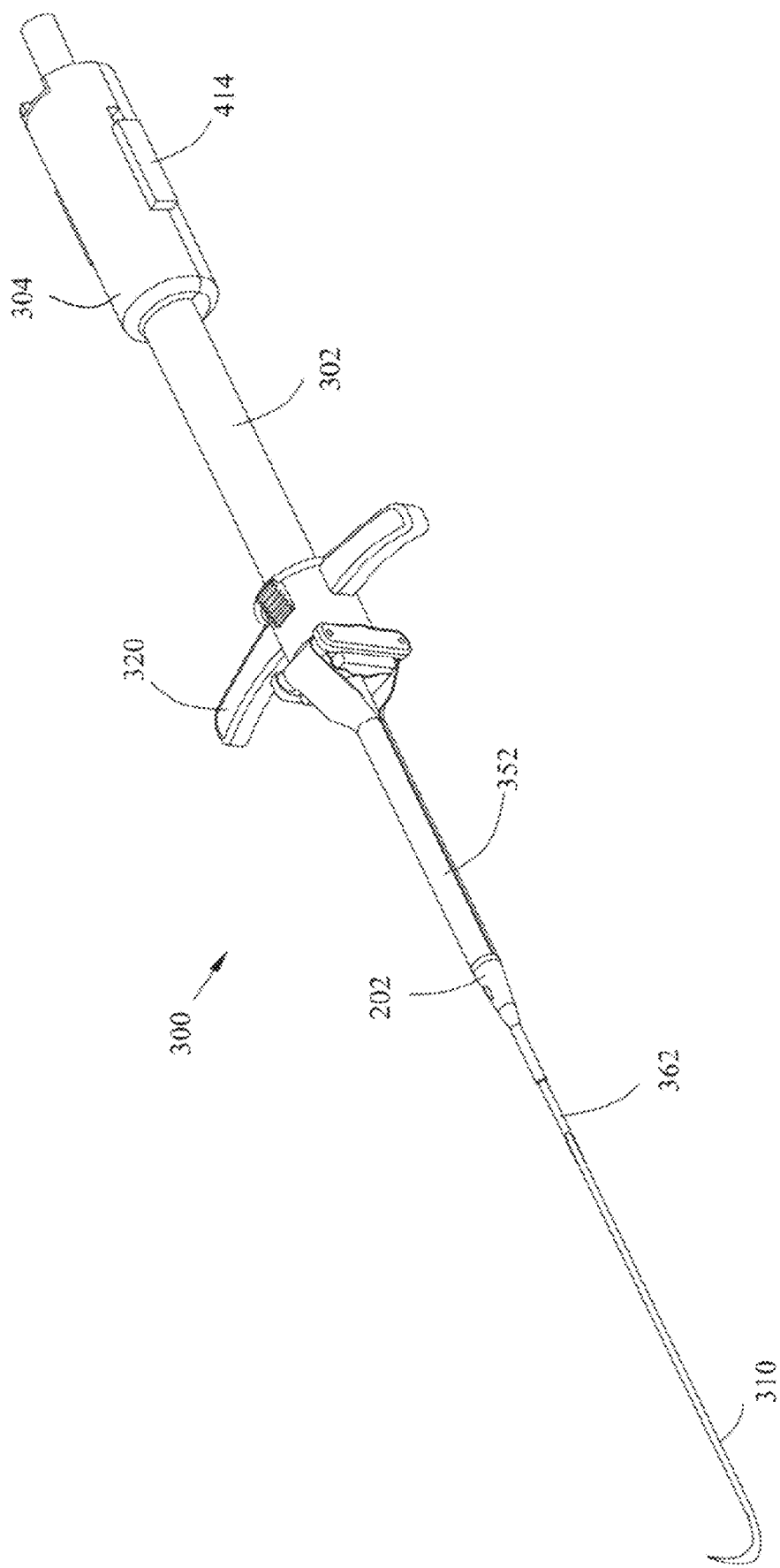
FIG. 74 is a perspective view of the exemplary deployment tool of FIG. 58 with the needle in an advanced configuration.
Figure 75:
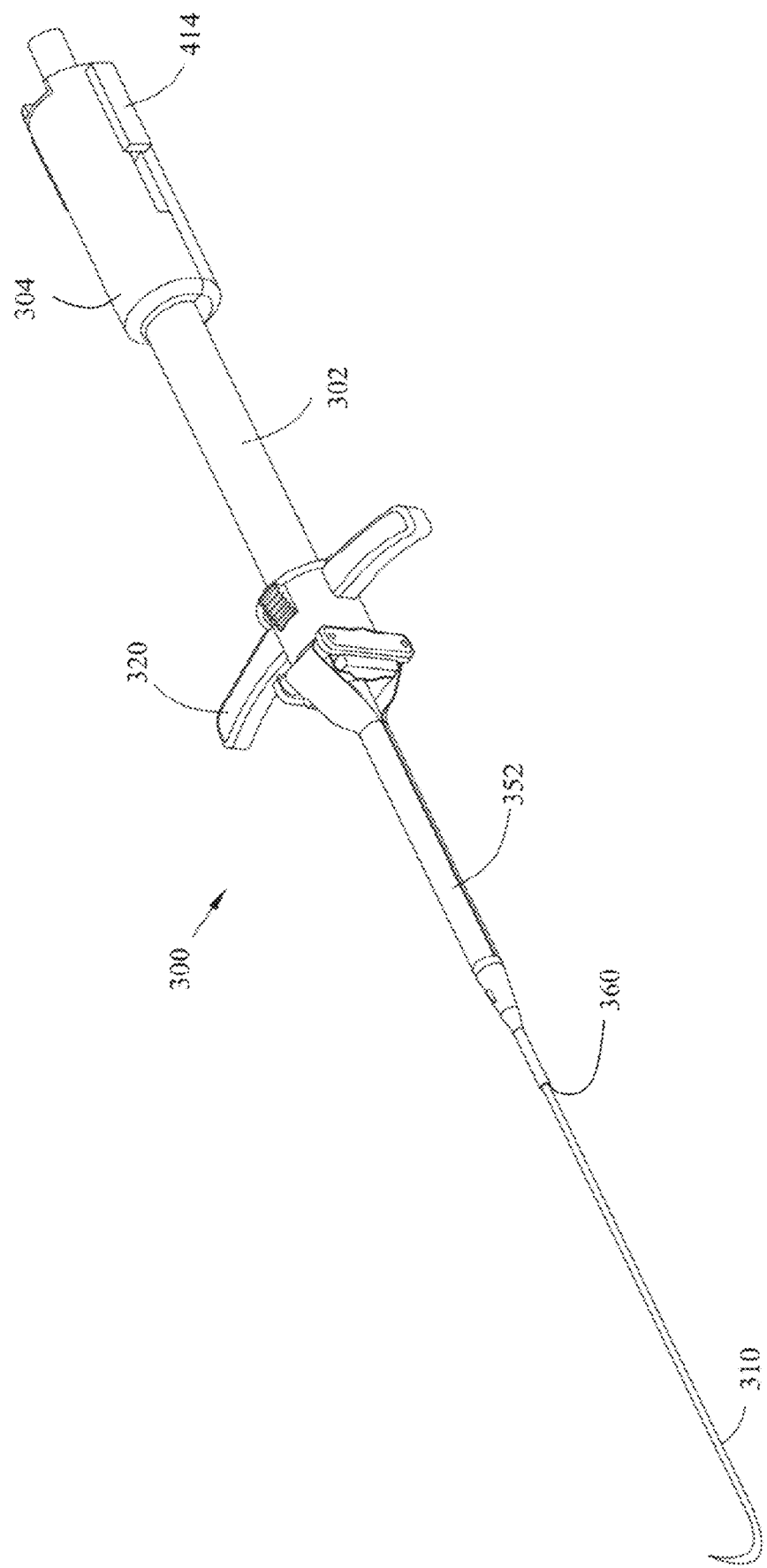
FIG. 75 is a perspective view of the exemplary deployment tool of FIG. 58 with the needle in a retracted configuration.

As the guidewire grip 312 moves distally toward the grip 304, the cam surface 422 and then the narrower region 424 (if one is utilized) move through the aperture 308 in the grip 304 and enter the space 392 defined within the grip 304. As the guidewire grip 312 moves distally, the cam surface 422 engages the rounded corner 408 at the proximal top edge of the tab 406 of the latch 394. Alternately, where the rounded corner 408 is not used, the cam surface 422 engages the tab 406 of the latch 394 in any suitable manner. Due to the increasing distance of the cam surface 422 from the longitudinal centerline of the guidewire 310 in the proximal direction, after the cam surface 422 initially encounters the tab 406, continued distal motion of the guidewire grip 312 moves the tab 406 further away from the longitudinal centerline of the guidewire 310. This motion of the tab 406 causes the latch 394 to rotate downward about the axle 398, against the bias exerted on the latch 394 by the leaf spring 412. As the latch 394 continues to rotate downward about the axle 398, the catch 402 rotates increasingly out of contact with the holdoff block catch 418. As the guidewire grip 312 continues to move distally, the catch 402 rotates completely out of contact with the holdoff block catch 418. At that point, the force exerted by the holdoff spring 413 in the proximal direction on the holdoff block 414 pushes the holdoff block 414 proximally, such that the first surface 416 of the holdoff block 414 engages the tab 406 of the latch 394 and holds the latch 394 off its initial, latched position. As a result, the needle 362 is now no longer held in the latched position. The holdoff block 414 is free to move proximally, and in the course of that proximal motion, the holdoff block 414 engages the distal end of the guidewire grip 312. The holdoff spring 413 exerts sufficient force that the user is capable of feeling that force, but not so much force that the guidewire grip 312 is jerked from the user's hand. When the user releases pressure on the guidewire grip 312, the proximal force exerted by the holdoff spring 413 on the holdoff block 414 is transmitted to the guidewire grip 312, pushing it proximally. Because the holdoff block 414 is coupled to the needle 362, the proximal force exerted on the guidewire grip 312 is also exerted on the needle 362, moving the needle 362 proximally. The size of the holdoff spring 413 and the holdoff block 414 are selected such that the guidewire grip 312, and the needle 362, are moved proximally a specific distance after the latch 394 is held off and the guidewire grip 312 is released. This specific distance is sufficient to allow the distal end of the needle 362 to retract proximal to the aperture 360 in the dilator tip 202, safely moving the sharp end of the needle 362 within the body of the deployment tool 300. Referring also to FIGS. 74-75, the automatic retraction of needle 362 is schematically illustrated. In FIG. 74, needle 362 is in its extended, distal position with holdoff block 414 in a corresponding distal position. Following disengagement of latch 394, holdoff block 414 in FIG. 75 has moved to its proximal position due to the force exerted by holdoff spring 413 resulting in the retraction of needle 362 into aperture 360 at the distal end of dilator tip 202.

The method of operation will now be described in the context of deployment tool 300 and deployment tool 301. The distal end of the needle 362 may already be positioned distal to the aperture 360 in the dilator tip 202 in an initial condition. According to other embodiments, the distal end of the needle 362 positioned proximal to the aperture 360 in the dilator tip 202 in an initial condition. If so, the needle 362 is first extended distally. Referring to FIG. 65 and deployment tool 300, that extension may be performed by urging the guidewire grip 312 distally. As described above, when the needle 362 is in the retracted position, the first surface 416 of the holdoff block 414 engages the tab 406 of the latch 394 and holds the latch 394 off its initial, latched position. When the guidewire grip 312 is pushed distally, the distal end of the guidewire grip 312 encounters the proximal end of the holdoff block 414, then urges the holdoff block 414 distally against the bias of the holdoff spring 413. The holdoff block catch 418 eventually moves distal to the catch 402 of the latch 394. At that point, the latch 394 is able to rotate upward about the axle 398 at the urging of the leaf spring 412. The user then releases the guidewire grip 312. Because the latch 394 has rotated back upward, release of the guidewire grip 312 allows the holdoff spring 413 to urge the holdoff block 414 proximally such that the holdoff block catch 418 presses against the catch 402 of the latch 394. The needle retraction assembly 390 is then in a configuration as seen in FIG. 63. The needle 362 is extended such that the distal end is positioned distal to the aperture 360 in the dilator tip 202.

Figure 79:
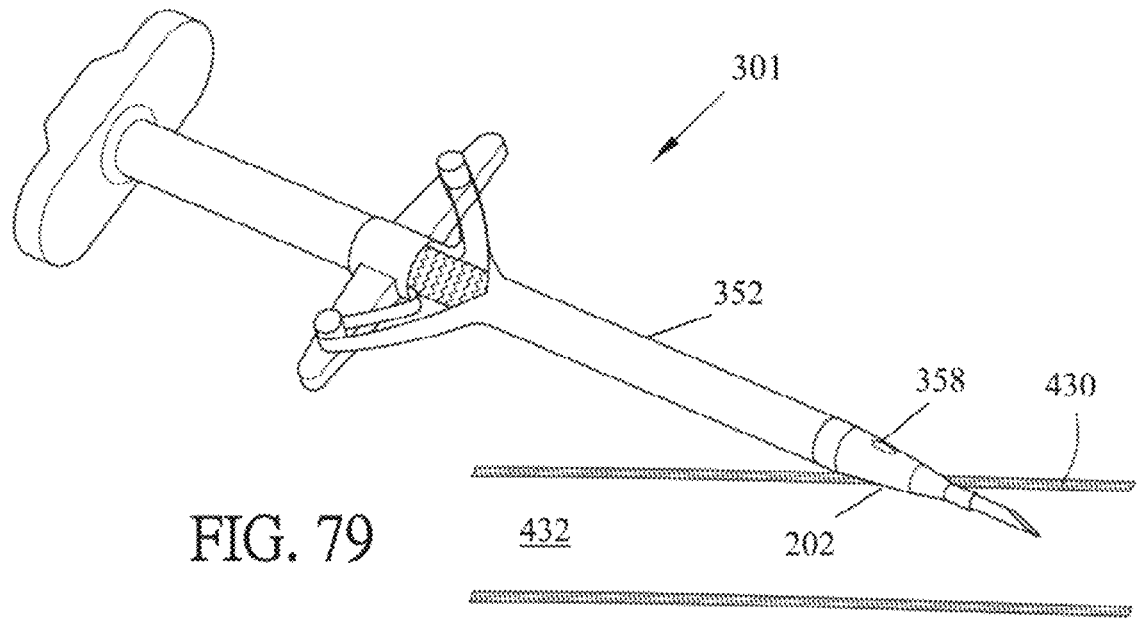
FIG. 79 is a side view of an exemplary deployment tool after the needle has been insertion through a wall of a blood vessel.
Figure 80:
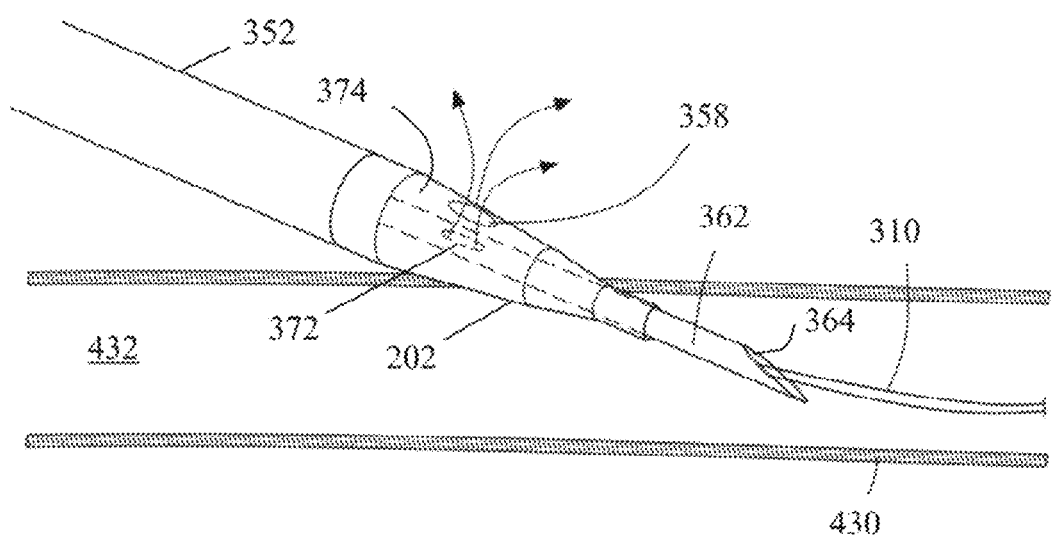
FIG. 80 is a detail view of the exemplary deployment tool of FIG. 79, schematically depicting visual bleed back indication.

Correspondingly, guidewire 310 may be withdrawn proximally if necessary and the user then inserts the distal end of the needle 362 into a side wall of a vessel to be treated. The guidewire 310 is then passed distally out of the aperture 364 at the distal end 362 of the needle 310. The guidewire 310 may be previously placed in the deployment tool 300, such as to advance the needle 362 distally and latch needle retraction assembly 390; if not, the guidewire 310 is fed into the deployment tool 300 through the aperture 308 in the grip 304. The guidewire 310 may be pushed distally out of the aperture 364 at the distal end of the needle 362 by grasping the guidewire grip 312 and pushing it distally. Referring also to FIGS. 62, in the insertion configuration of the deployment tool 300, in which the distal end of the needle is positioned distal to the aperture 360 in the dilator tip 202, the needle bleedback port 372 is located in the plenum 374 defined in the dilator tip 202. Similarly and referring also to FIG. 79 and the detail view of FIG. 80, when the distal end of the needle 362 of deployment tool 301 enters the lumen 432 of the blood vessel 430, blood flows from the lumen 432 of the blood vessel 430, into the aperture 364 at the distal end of the needle 362, through the lumen of the needle 362, outward through the needle bleedback port 372, into the plenum 374, and then out of the bleedback port 358. Flow of blood out of the bleedback port 358 allows the user to confirm that the distal end of the needle 362 is correctly positioned in the true lumen 432 of the blood vessel 430, and that the procedure can continue.

Figure 66:
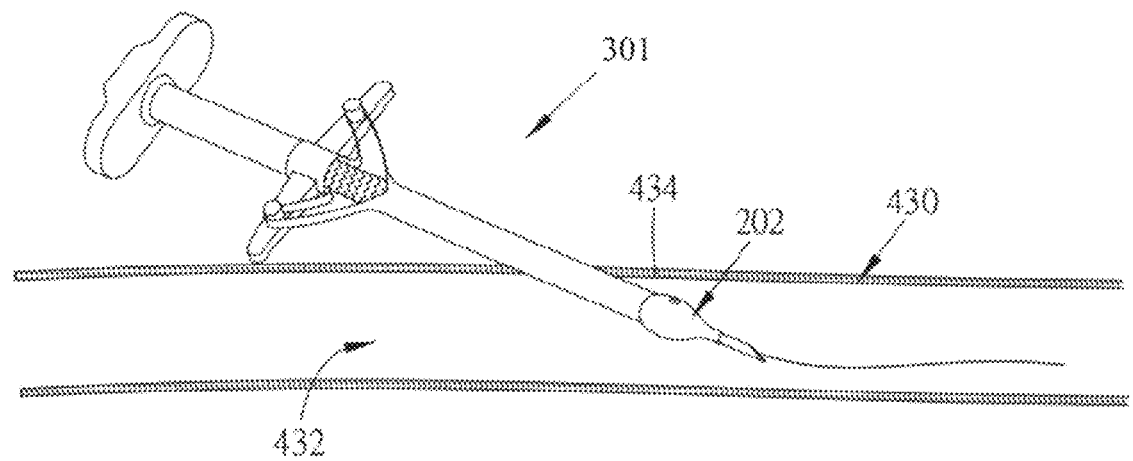
FIG. 66 is a side view of an exemplary deployment tool after insertion through a wall of a blood vessel.

The user then moves the deployment tool distally, following the guidewire 310 as desired. Referring also to FIG. 66 and deployment tool 301, as the dilator tip 202 enters the lumen 432 of the blood vessel 430, the dilator tip 202 expands the hole in the wall 434 of the blood vessel 430 originally created by the needle 362. Once the dilator tip 202 has entered the lumen 432 of the blood vessel 430, the user may continue to advance the deployment tool 301 distally a clinically appropriate distance. After the dilator tip 202 has reached the appropriate location within the lumen 432 of the blood vessel 430, the user stops moving the deployment tool 301 distally.

Figure 67:
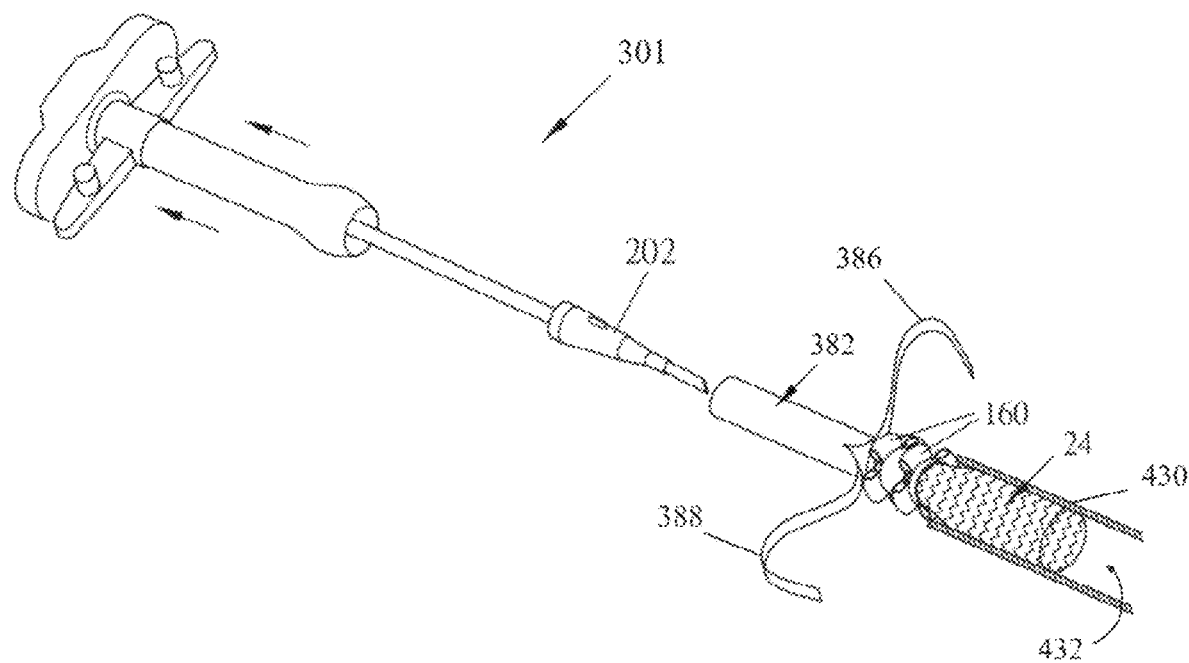
FIG. 67 is a perspective view of an exemplary deployment tool being withdrawn after inserting a vascular graft into the end of a blood vessel.

Alternately, where the clinician wishes to join two vessels end-to-end, the needle 362 and guidewire 310 need not be used, although they may be utilized if desired by the user. Referring also to FIG. 67, the distal end of the dilator tip 202 is inserted into an end 436 of the blood vessel 430. In this situation, the blood vessel 430 may be clamped further from the deployment tool 301 to prevent flow of blood outward therefrom, or the blood vessel 430 may be separated from the circulatory system so that bleeding is not an issue.

The needle 362 is then retracted, having served its purpose. The further presence of the distal end of the needle 362 in the lumen 432 of the blood vessel 430 increases the risk that the distal end of the needle 362 inadvertently will injure or penetrate the blood vessel 430. The needle 362 is retracted, either manually or automatically by moving the guidewire grip 312 distally as described in greater detail above with regard to deployment tool 300. The needle 362 was held in position by the needle retraction assembly 390, and distal motion of the guidewire grip 312 at least partially into contact with the needle retraction assembly 390 causes the needle retraction assembly 390 to release the needle 362 and move the needle 362 proximally. The holdoff spring 413 causes the needle 362 to auto-retract proximally, such that the distal end of the needle 362 moves proximally relative to the distal end of the dilator tip 202. Upon proximal retraction of the needle 362, the needle bleedback port 372 is no longer located in the plenum 374 of the dilator tip 202, and as a result blood no longer flows out of the needle bleedback port 372 into the plenum 374. Consequently, blood no longer flows out of the bleedback port 358. If used, guidewire 310 may be removed by pulling it proximally until the distal end of the guidewire 310 moves proximally out of the aperture 308 in the grip 304 for deployment tool 300 or out of needle grip 303 for deployment tool 301.

Figure 68:
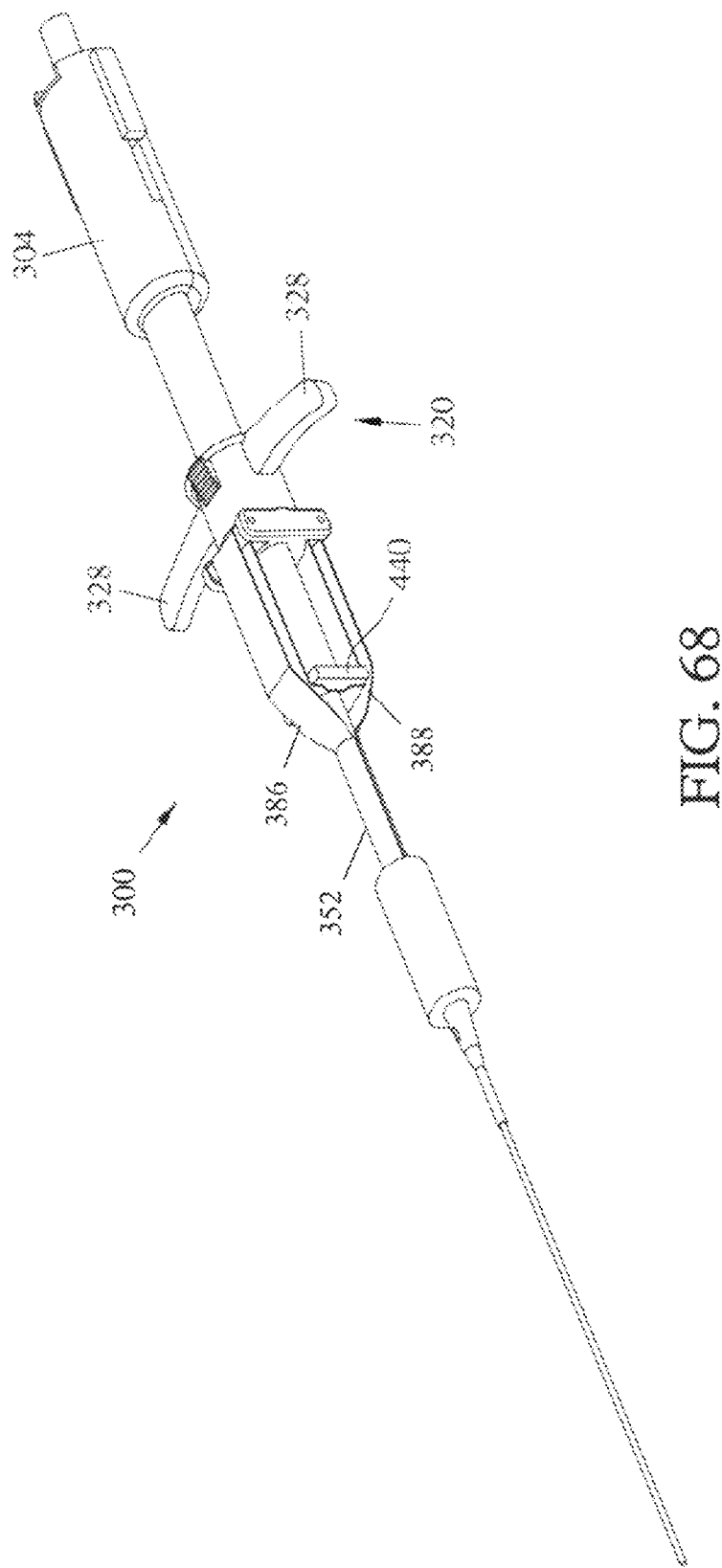
FIG. 68 is a perspective view of an exemplary deployment tool during actuation to separate a distal sheath.
Figure 76:
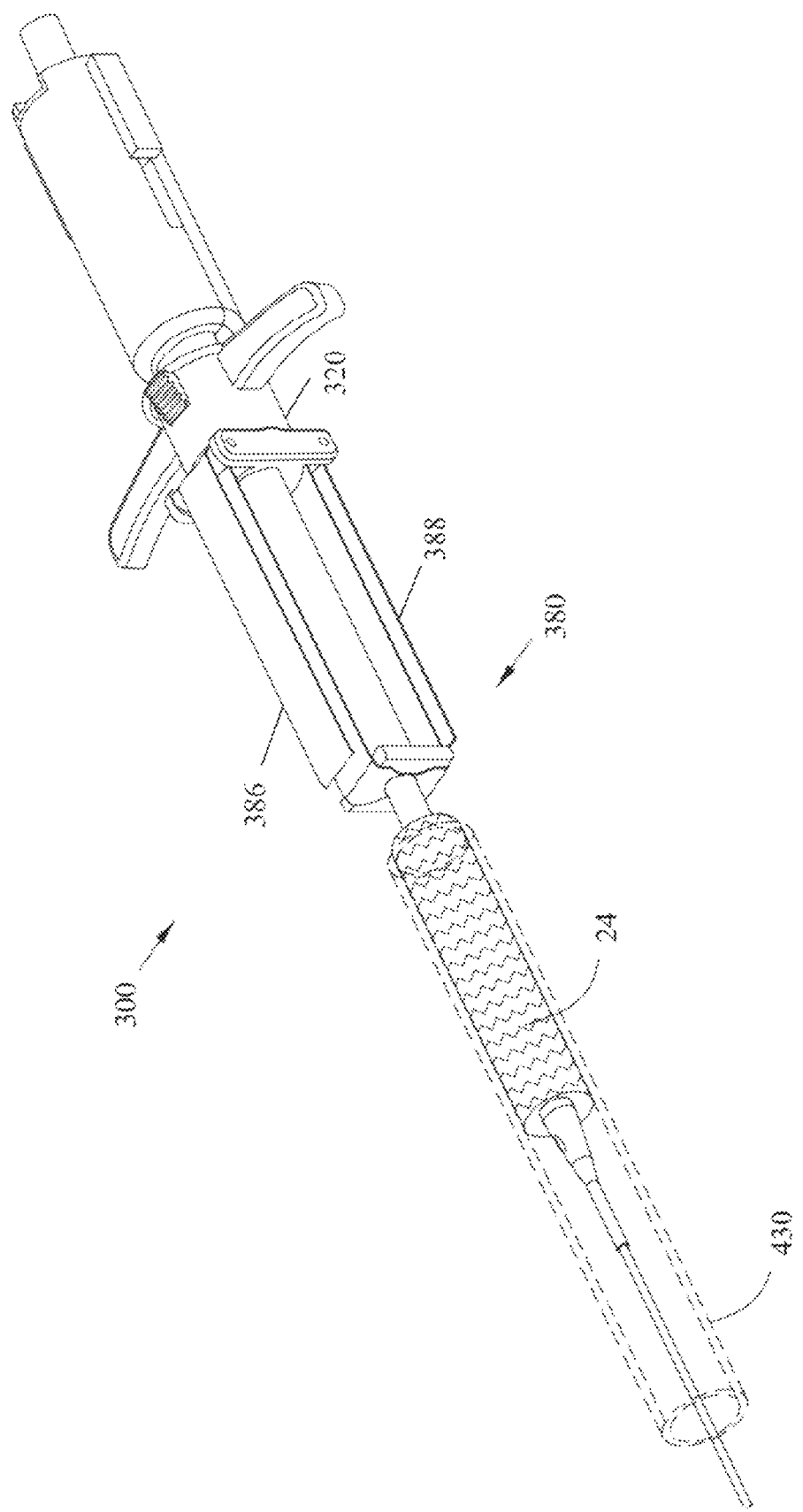
FIG. 76 is a perspective view of an exemplary deployment tool after actuation to separate a distal sheath.

With the dilator tip 202 placed in the desired location, the vascular graft 24 is also in the desired location relative to the blood vessel 430. Referring also to FIG. 61, the user then may split the distal sheath 352 of the sheath assembly 380. Referring also to FIG. 68, to split the distal sheath 352, the user moves the slider actuator 320 proximally relative to the grip 304. The user may grasp one or more arms 328 of the slider actuator 320 to do so. The user may hold the grip 304 with one hand and the slider actuator 320 with the other. When the user begins to move the slider actuator 320 proximally relative to the grip 304, the distal sheath 352 begins to split. The distal sheath 352 splits toward the distal direction. As noted, the distal sheath 352 may include one or more longitudinal separation lines 389. As the distal sheath 352 is peeled away, the peeled locations no longer compress the vascular graft 24 against the mandrel, as described earlier in this document with regard to other embodiments of the deployment tool, and the vascular graft 24 begins to expand at the peeled locations. Referring also to FIG. 76, slider actuator 320 has been moved to its most proximal position and the distal sheath 352 has been peeled away completely so that the portion of the vascular graft 24 that had been constrained by the distal sheath 352 has fully expanded, and that portion of the vascular graft 24 advantageously has expanded against the inner wall of the blood vessel 430.

Figure 81:
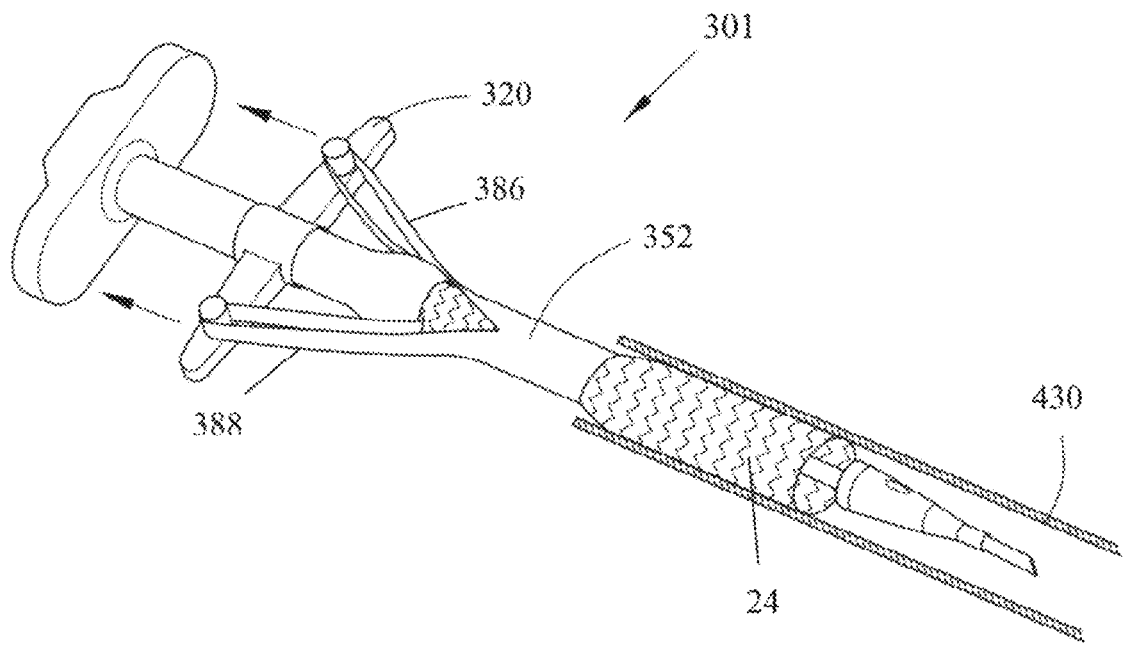
FIG. 81 is a perspective view of an exemplary deployment tool being actuated to separate a distal sheath to deploy a vascular graft into the end of a blood vessel.
Figure 82:
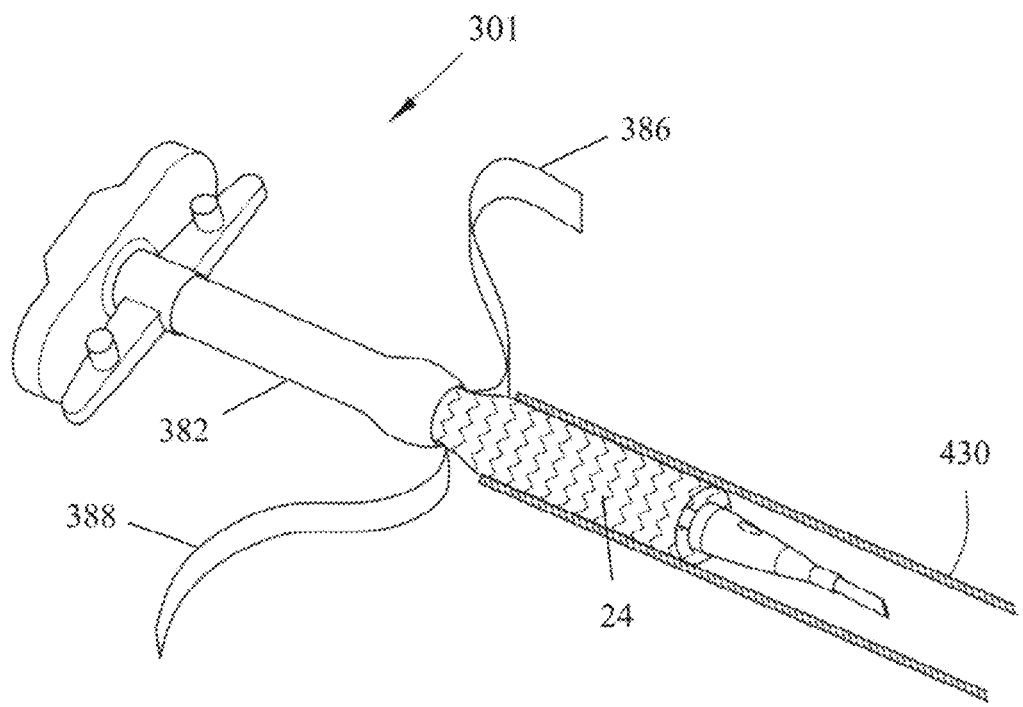
FIG. 82 is a perspective view of the exemplary deployment tool of FIG. 81 following separation of the distal sheath.

Alternately, referring also to FIG. 81 with regard to the deployment tool 301 shown in FIG. 59 where the slider actuator 320 includes pegs 344 instead of rollers 336, proximal motion of the slider actuator 320 relative to the grip 304 also causes the distal sheath 352 to split. The splitting locations in this embodiment may be, but need not be, at locations generally rotated ninety degrees relative to the embodiment in which the rollers 336 are utilized. As with the previous embodiment, as the distal sheath 352 is peeled away by the engagement of slider actuator 320 with ribbons 386, 388, the peeled locations no longer compress the vascular graft 24 against the mandrel. When the distal sheath 352 has been peeled away completely, the portion of the vascular graft 24 that had been constrained by the distal sheath 352 has fully expanded, and that portion of the vascular graft 24 advantageously has expanded against the inner wall of the blood vessel 430. Correspondingly and referring also to FIG. 82, when distal sheath 352 has been peeled away completely, ribbons 386, 388 are freed from slider actuator 320 and subsequently may be used to split proximal sheath 382 as discussed below.

Figure 70:
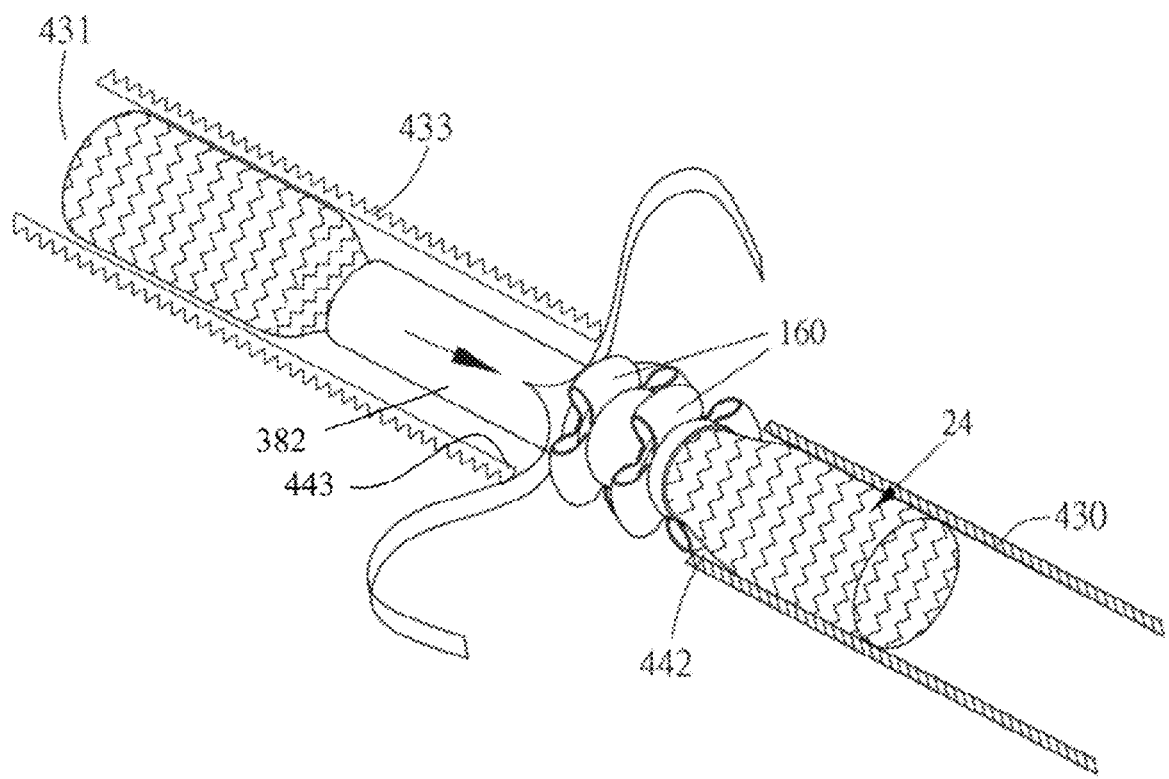
FIG. 70 is a perspective view of a vascular graft being inserted into the end of a second blood vessel

The vascular graft 24 advantageously is placed through a hole created in the side of a blood vessel 430 such that the distal of the two suture cuffs 160 on the vascular graft 24 is adjacent to that hole in the side of the blood vessel 430. The user then sutures that suture cuff 160 to the blood vessel 430, providing additional security to hold the vascular graft 24 in place. Referring also to FIG. 70, where the vascular graft 24 is placed into the end of a blood vessel 430, one of the two suture cuffs 160 advantageously is placed at the end 442 of the blood vessel 430, and that suture cuff 160 is sutured to the end 442 of the blood vessel 430, providing additional security to hold the vascular graft 24 in place.

Figure 71:
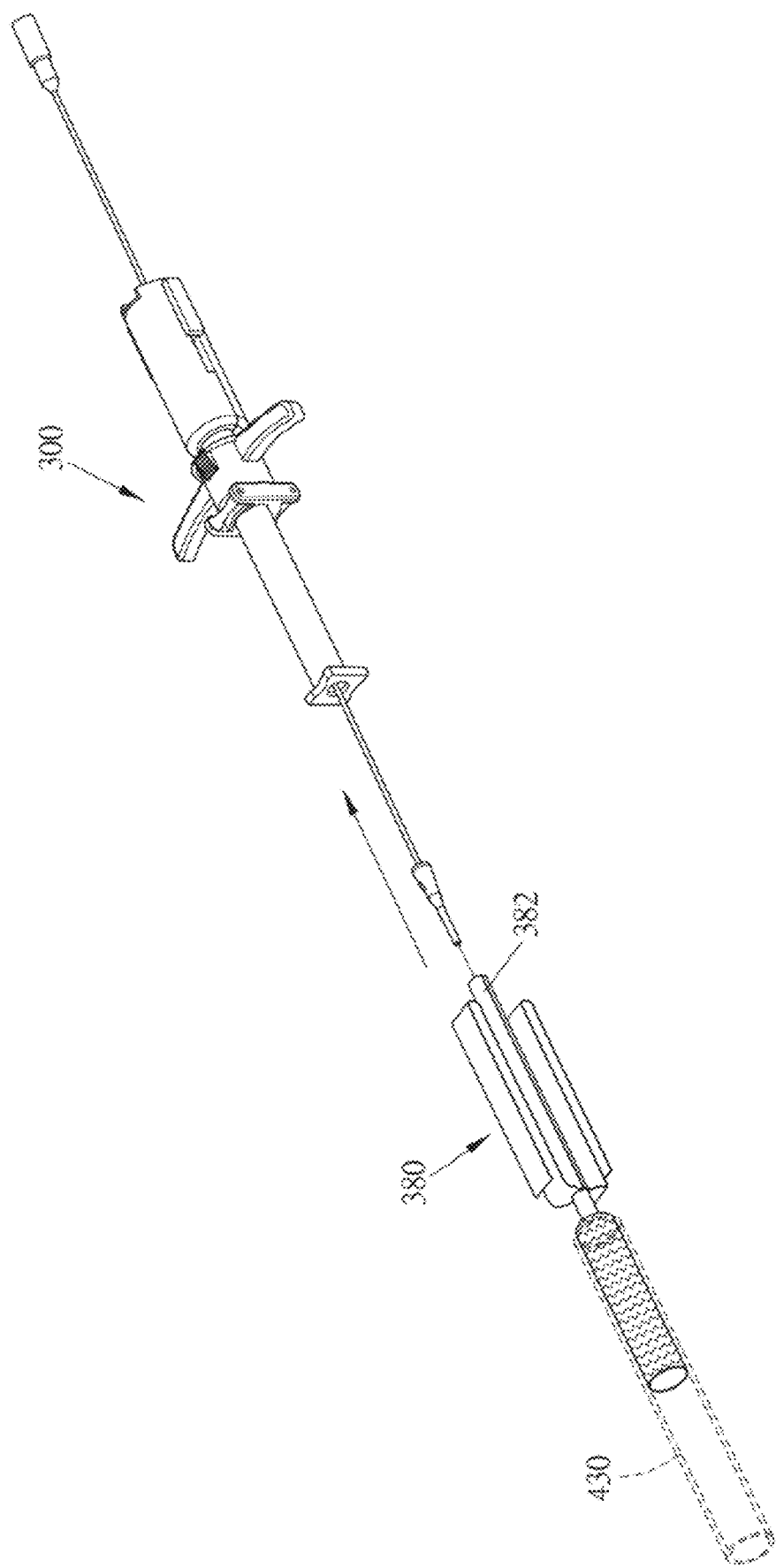
FIG. 71 is a perspective view of an exemplary deployment tool being removed from a deployed segment of a vascular graft.
Figure 77:
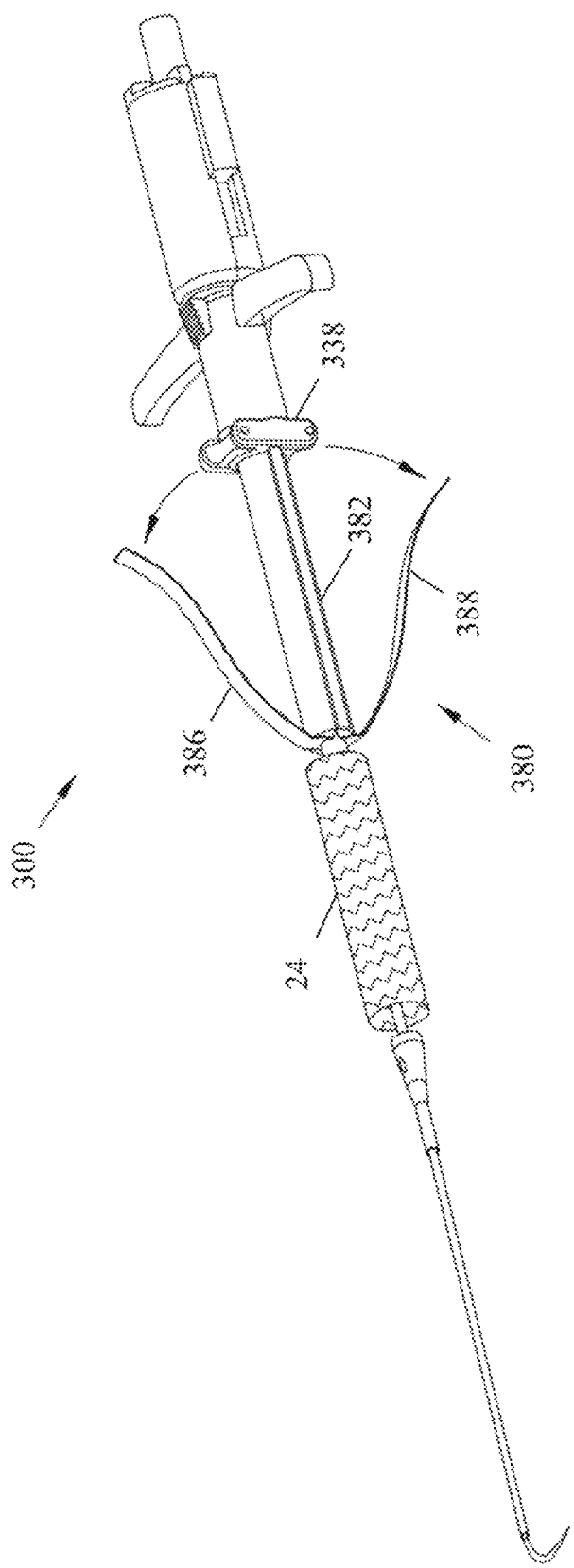
FIG. 77 is a perspective view of an exemplary deployment tool with a distal portion of a vascular graft expanded and a proximal sheath prior to separation.

Referring also to FIG. 77, with slider actuator 320 in its most proximal position and the distal portion of the vascular graft 24 that had been constrained by distal sheath 352 fully expanded, ribbons 386, 388 may be removed from roller frame 338 so that they may subsequently manipulated to peel away proximal sheath 382. For example, referring also to FIG. 71, if the deployment tool 300 has not been withdrawn from the blood vessel 430, the deployment tool 300 is withdrawn. The sheath assembly 380 remains in contact with the blood vessel 430, with the distal sheath 352 having been peeled away, and the vascular graft 24 sutured to the blood vessel 430. Alternately, the deployment tool 300 is removed from the blood vessel 430 subsequent to suturing the vascular graft 24 to the blood vessel 430. Referring also to FIG. 70, the proximal end of the sheath assembly 380, including the proximal sheath 382, is placed into the lumen 431 of a second vessel 433, through the end of the second vessel 433. The second vessel 433 may be a blood vessel in the body of the patient, or may be a natural or artificial vessel to be implanted in the body of the patient having a lumen that conducts the patient's blood. The proximal sheath 382 is removed from the proximal end of the vascular graft 24 in the same manner that the distal sheath 352 was removed from the distal end of the vascular graft 24. As one example, the slider actuator 320 may be moved distally to cause the proximal sheath 382 to peel away from the vascular graft 24. As another example, the proximal sheath 382 can be removed from the vascular graft 24 in any other suitable manner, such as by grasping and pulling ribbons 386, 388 manually. When the proximal sheath 382 has been peeled away completely, the portion of the vascular graft 24 that had been constrained by the proximal sheath 382 has fully expanded, and that portion of the vascular graft 24 advantageously has expanded against the inner wall of the second vessel 433. The proximal of the two suture cuffs 160 on the vascular graft 24 may be adjacent to the end of the second vessel 433, and that suture cuff 160 may be sutured to the end 443 of the second vessel 433, providing additional security to hold the vascular graft 24 in place. Both the proximal sheath 382 and distal sheath 352 are removed from the patient, and the procedure is complete; the blood vessel 430 and second vessel 433 are connected, and blood may flow therebetween through the lumen of the vascular graft 24 that has been sutured in place.

Figure 85:
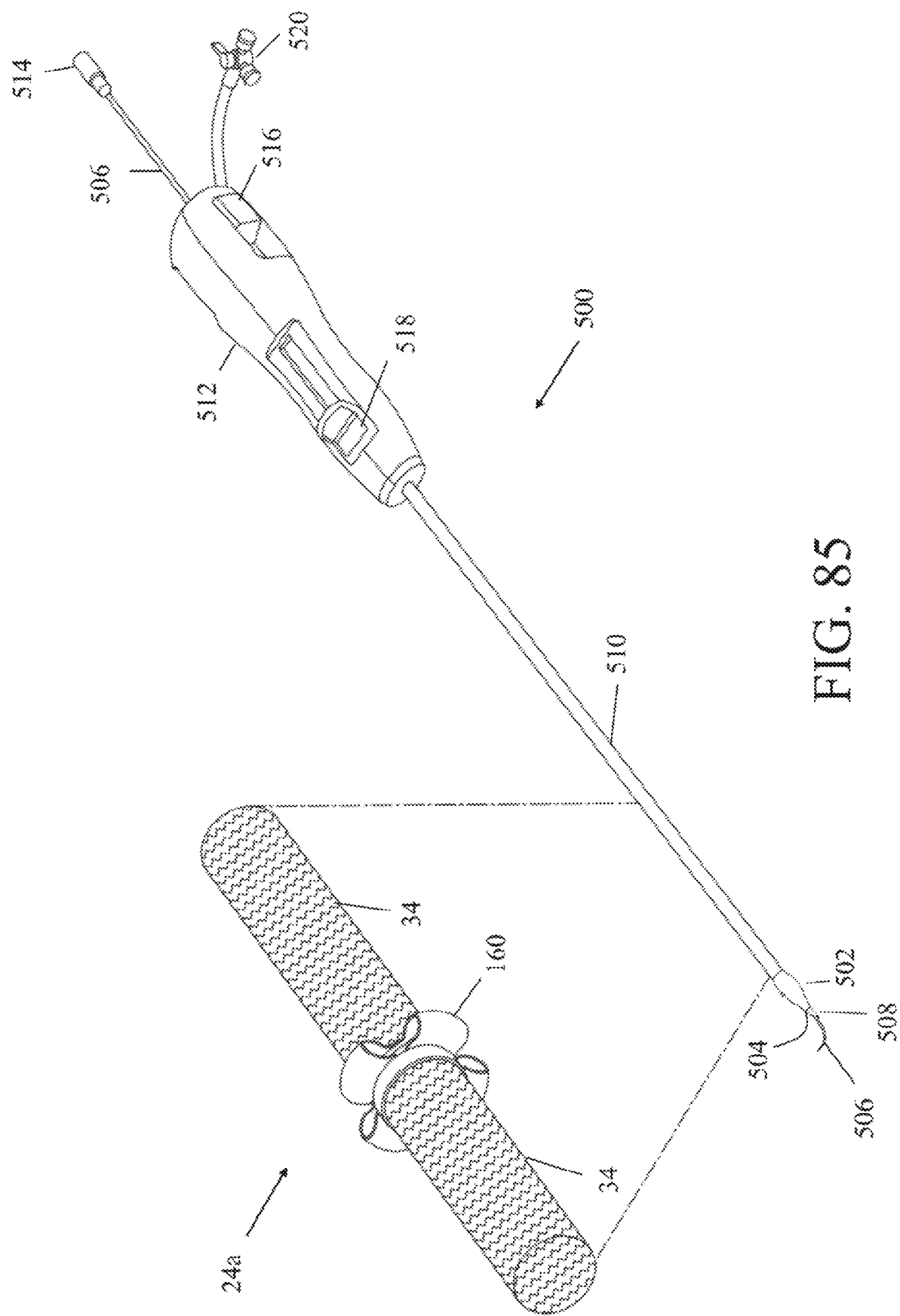
FIG. 85 is a perspective view of another exemplary embodiment of deployment tool.

Referring also to FIG. 85, another exemplary deployment tool 500 is shown. At the distal end of the deployment tool 500, is a blunt dilator tip 502. The dilator tip 502 is sized and shaped to dilate an incision or opening made in a vessel, similar to embodiments noted above. A passage 504 is defined through the dilator tip 502 and a guidewire 506 may be extensible through and/or retractable into the passage 504. A needle 508 may be located within the passage 504 through the dilator tip 502 in a neutral position, being advanceable relative to the dilator tip 502 in order to puncture a vessel in the patient's body. In this embodiment, the needle 508 is hollow, such that the guidewire 506 can pass through the needle 508 as well as enabling bleed back indication as discussed below. Proximal to the dilator tip 502, the deployment tool 500 includes a mandrel 546 that is not visible in this view, but is similar to the embodiments disclosed above and as shown in FIGS. 94-98 for example. As shown schematically, a vascular graft 24a, for example having ends formed from expandable mesh 34 and one or more integral suture cuffs 160, is wrapped around mandrel 546 and compressed at least partially against the mandrel by a retractable sheath 510. Although in the embodiment shown suture cuff 160 is positioned centrally between the expandable mesh 34 portions, other configurations are also suitable as described above. A handle 512 is connected to the proximal end of the mandrel, either by attachment or integral fabrication. A lumen extending through handle 512 communicates with passage 504 exiting dilator tip 502. Accordingly, manipulation of the proximal end of guidewire 506, such as via guidewire grip 514 allows advancement and retraction of the guidewire 506 as desired. Needle 508 is coupled to a needle advancement button 516 using any suitable mechanism, such as described for the other embodiments of this disclosure, and is biased proximally towards a retracted position within dilator tip 502. In particular, needle advancement button 516 may be moved distally to a locked position that positions the needle 508 in an advanced configuration that extends beyond dilator tip 502 to facilitate insertion through a vessel wall. Subsequent advancement of guidewire 506 then causes guidewire grip 514 to release needle advancement button 516 so that needle 508 retracts automatically. A slider actuator 518 is configured to selectively withdraw sheath 510 as a result of proximal movement of actuator 518. As desired, actuator 518 is coupled to sheath 510 by a ratchet or other suitable mechanism that transmits only a proximally withdrawing force. For example, a first cycle of actuator 518 from a distal position to a proximal position may cause deployment of a distal end of vascular graft 24a. As desired, actuator 518 may be configured to move only proximally until the first cycle is completed. Correspondingly, actuator 518 then returns to the distal position so that a second cycle from the distal position to the proximal position causes deployment of the proximal end of vascular graft 24a. It should be recognized that other configurations are possible, including providing full deployment with a single cycle or more than two cycles. Deployment tool 500 also features a fitting for the delivery of inflation fluid as discussed below, such as through three-way stop cock 520. While the deployment tool 500 is described here in the context of its usage with a vascular graft 24a, the deployment tool 500 may be used with any other jumper, graft or anchor described in this document, as appropriate.

Figure 86:
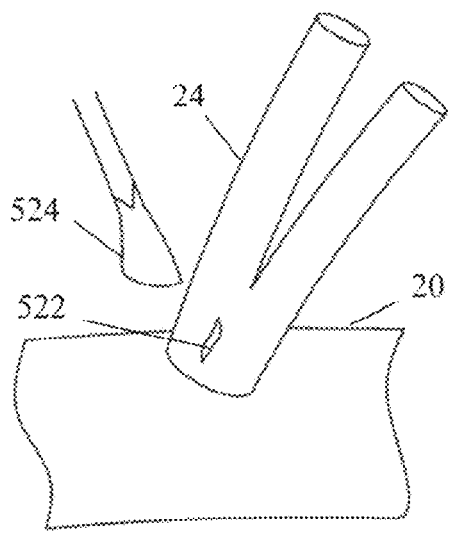
FIG. 86 is a detail view showing creating of an opening in a branch graft to allow introduction of a deployment tool.
Figure 87:
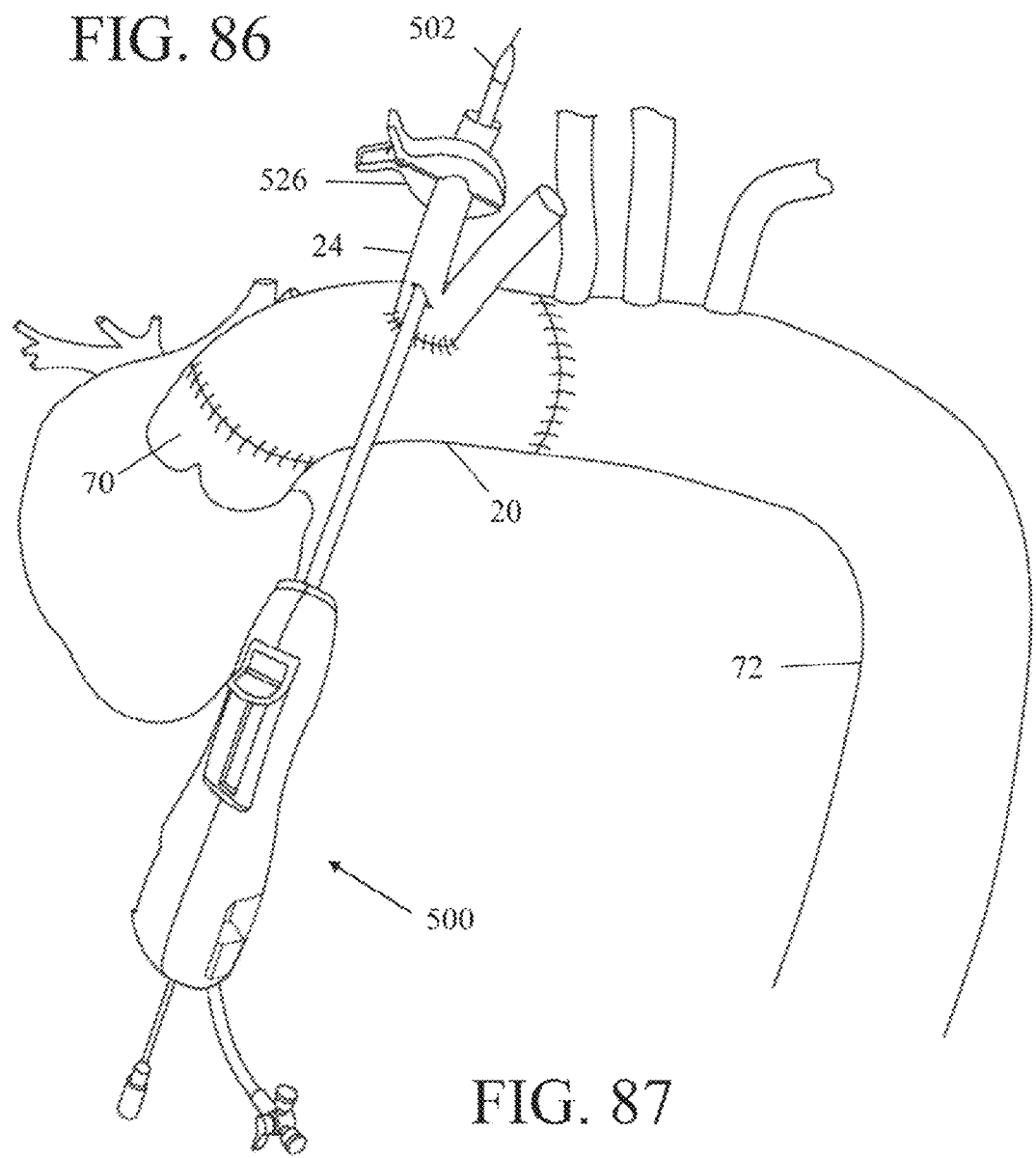
FIG. 87 is a perspective view of an exemplary deployment tool introduced through a branch graft of an aortic graft.
Figure 88:
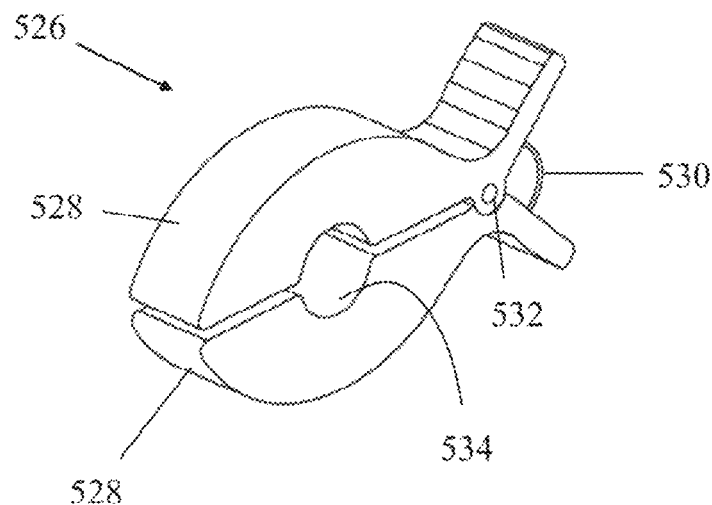
FIG. 88 is a perspective view of an embodiment of an exemplary graft clamp.
Figure 89:
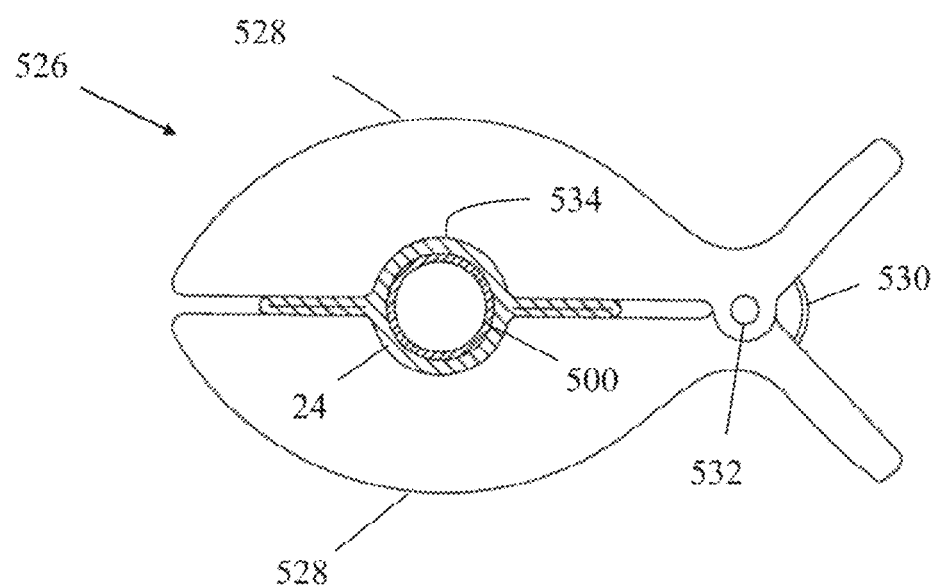
FIG. 89 is a side view of an exemplary graft clamp secured around a branch graft.

As detailed below, one exemplary usage of deployment tool 500 is for placement of vascular graft 24a within an aortic branch graft. Referring also to FIG. 86, a portion of aortic graft 20 is shown having branch graft 24. An opening 522 may be formed in a proximal section of branch graft 24, such as with a scalpel 524 or any other suitable tool. Referring also to FIG. 87, aortic graft 20 is shown as having been secured within the patient's vasculature between the aortic stump 70 and the descending aorta 72, similar to embodiments described above. The distal end of deployment tool 500 with dilator tip 502 is then introduced through opening 522, fed through the internal diameter of branch graft 24 and advanced out of one of the distal ends. A graft clamp 526 is spring loaded and may be releasably secured around branch graft 24 with deployment tool 500 disposed within to reduce blood flow/loss during delivery and deployment of the stent graft. Referring also to FIG. 88, a detail view of graft clamp 526 is shown. Opposing jaws 528 are biased by a spring 530 into a closed configuration, pivoting on a hinge 532. When closed, jaws 528 define a generally circular opening 534 that is sized to compress a graft to reduce leakage of blood during a procedure. As an illustration only and without limitation, opening 534 may be approximately 12 F. For example, referring also to FIG. 89 which shows a side view of graft clamp 526 as positioned around branch graft 24 as depicted in FIG. 87. In particular, when graft clamp 526 is closed, opening 534 conforms closely to the outer diameter of deployment tool 500 so that branch graft 24 is substantially sealed around the outer diameter.

Figure 90:
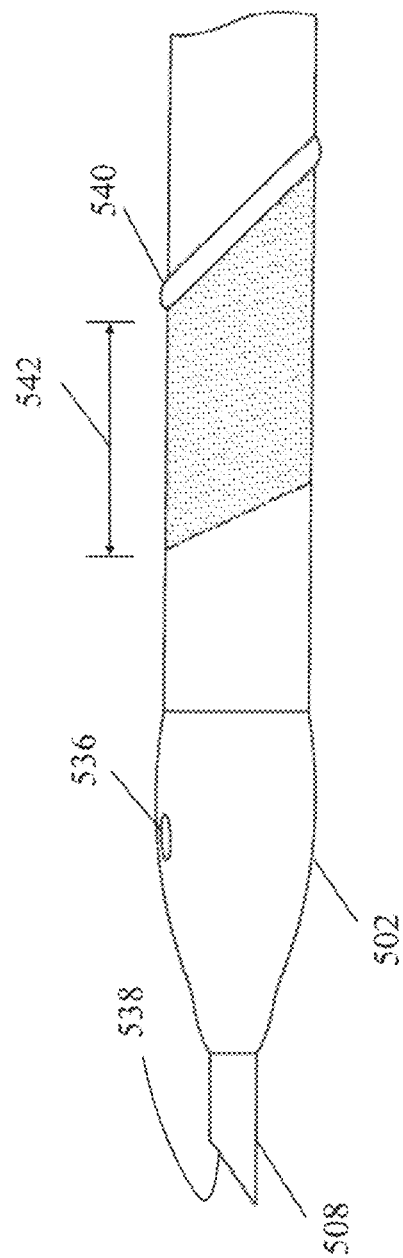
FIG. 90 is a perspective view of the distal end of an exemplary deployment tool.
Figure 91:
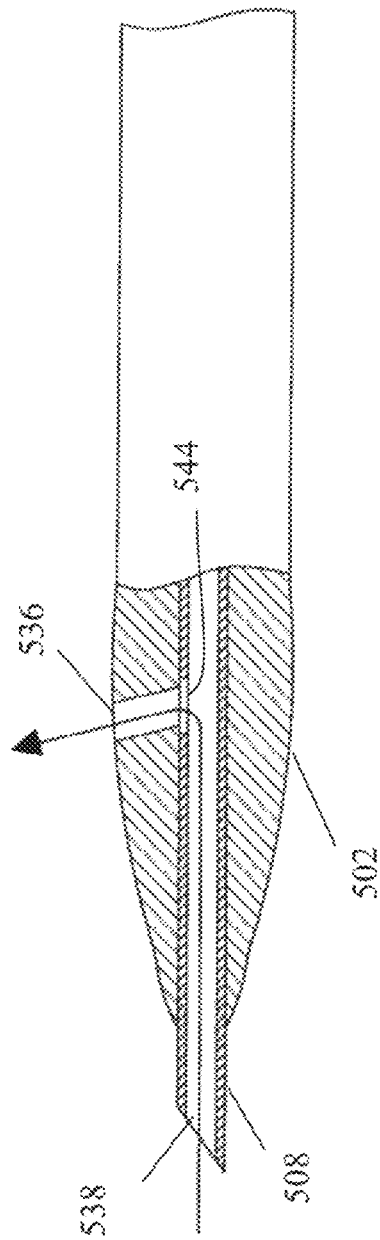
FIG. 91 is a hidden view of the interior of the distal end of FIG. 90.
Figure 92:
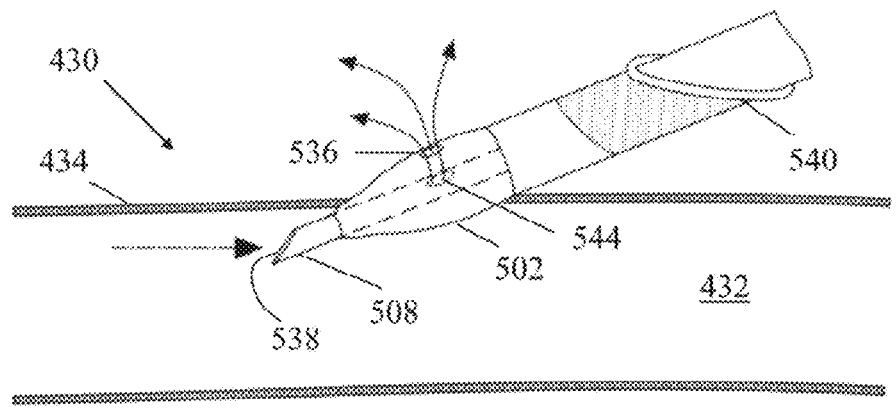
FIG. 92 is a detail view of the exemplary deployment tool of FIG. 90, schematically depicting visual bleed back indication.

As with other embodiments of this disclosure, deployment tool 500 may have a bleedback indication feature to aid positioning within a patient's vessel. Referring also to FIG. 90, a detail view of the distal end of deployment tool 500 is shown. Dilator tip 502 is provided with a bleedback port 536 defined through its outer surface that is in fluid communication with a lumen 538 of needle 508. Further, a depth rib 540 on the outer diameter of the distal end of deployment tool 500 is configured to reduce the risk of inserting the tool beyond a desired amount. In this embodiment, rib 540 is angled approximately 25-30° with respect to the longitudinal axis of deployment tool 500 to correspond with a desired insertion angle for a trans-vascular arterial insertion and other angles may be used as warranted for different applications. An indicated area 542 represents an intended insertion zone, which is approximately 1 cm in this embodiment but can also be adjusted as warranted depending on the desired usage. Referring also to FIGS. 91 and 92, the bleedback function is schematically illustrated. A needle bleedback port 544 in needle 508 is aligned with bleedback port 536 in dilator tip 502 when needle 508 is in its extended configuration. Accordingly, after needle 508 has penetrated the wall 434 of vessel 430, blood from vessel lumen 432 can flow into needle lumen 538, through needle bleedback port 544 and out bleedback port 536 to signal presence of the needle within the vessel. Thus, referring also to FIG. 93, guidewire 506 may be advanced distally past needle 508, such that complete advancement of guidewire 506 releases needle advancement button 516 as noted above, causing needle 508 to retract automatically as indicated in phantom. Then, deployment tool 500 can be further advanced through vessel wall 434 with rib 540 guiding the desired insertion depth.

Figure 93:
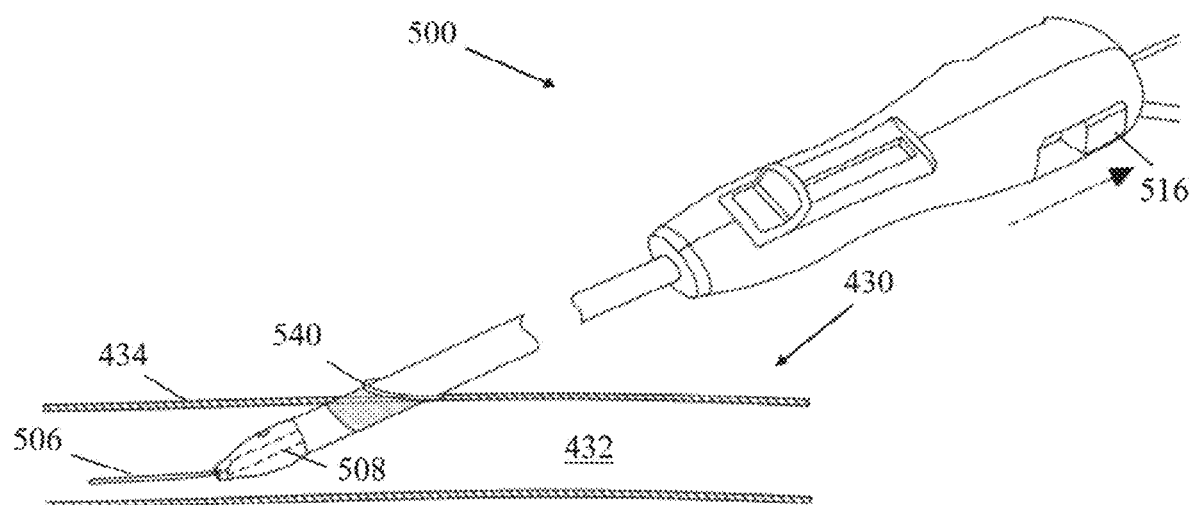
FIG. 93 is a side view of an exemplary deployment tool following automatic retraction of a needle.
Figure 94:
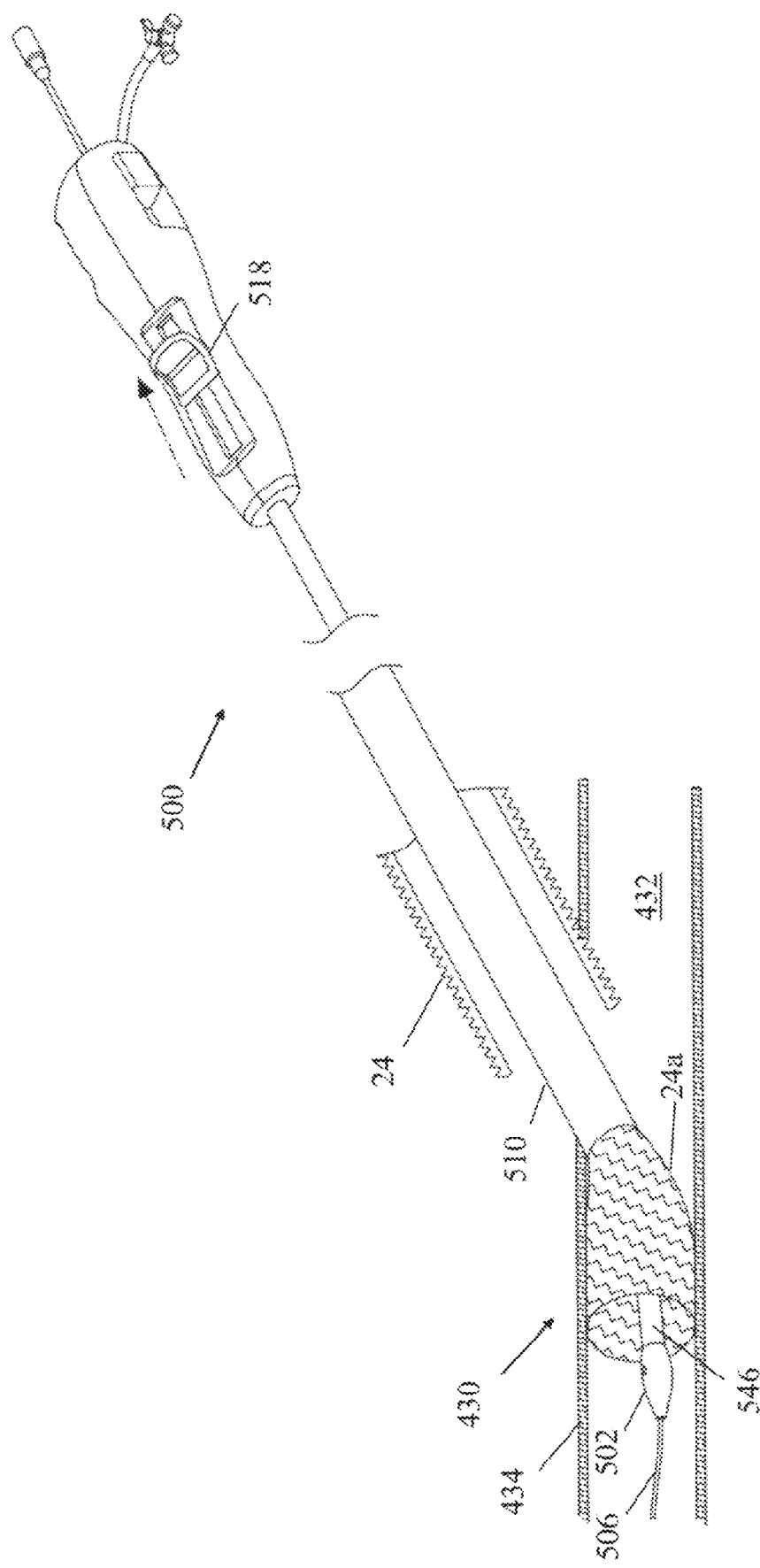
FIG. 94 is a side view of an exemplary deployment tool during deployment of a distal portion of a vascular graft.
Figure 95:
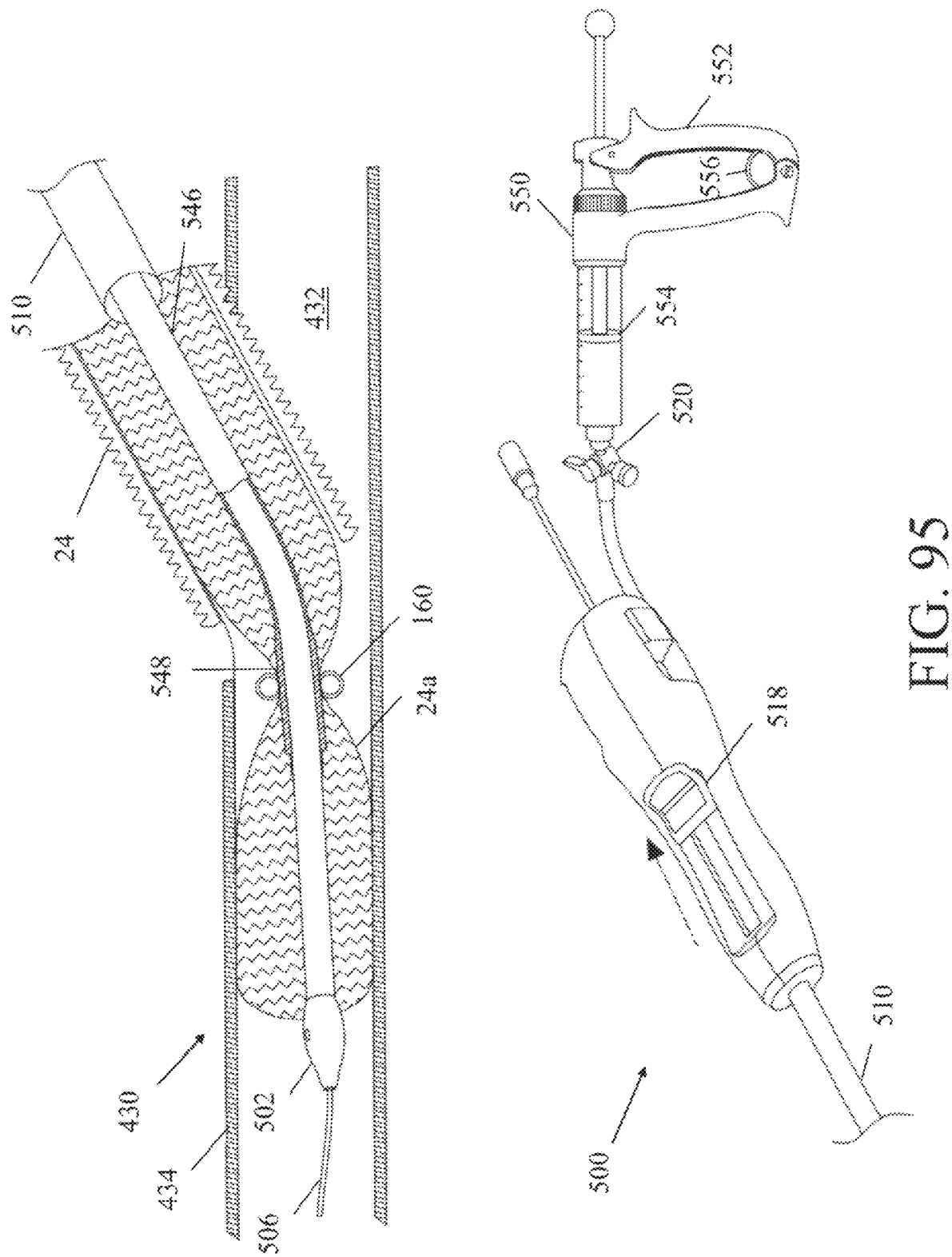
FIG. 95 is a side view of an exemplary deployment tool following deployment of a proximal portion of a vascular graft.

Referring also to FIG. 94, once the distal end of deployment tool 500 has been inserted to the desired depth within vessel 430 with the visual feedback provided by rib 540 (as shown in FIG. 93), actuator 518 is then moved proximally, such as through a first cycle as discussed above so that a distal portion of vascular graft 24a is deployed by withdrawing sheath 510 proximally, allowing expansion of this portion of vascular graft 24a from its compressed, delivery configuration. For example, the first cycle of actuator 518 may cause a proximal movement of approximately 3 to 3.5 cm of sheath 510 to expose a corresponding amount of vascular graft 24a. In this view, proximal movement of actuator 518 has not completed the first cycle and suture cuff 160 is still within sheath 510. After actuator 518 has completed movement to the proximal position, completing the first cycle, actuator 518 may then return to the distal position and, as desired, may be biased so that it assumes the distal position automatically after completing the first cycle. Referring also to FIG. 95, the end of branch graft 24 may be positioned to that vascular graft 24a will be deployed within its lumen. For example, the distal end of branch graft 24 may be positioned adjacent suture cuff 160 as shown. Actuator 518 is again moved proximally, such as through a second cycle as discussed above so that a proximal portion of vascular graft 24a is deployed as sheath 510 is withdrawn completely, allowing the proximal portion of vascular graft 24a to expand from its compressed configuration. As desired, after completion of the second cycle, actuator 518 may be locked in its proximal position given that sheath 510 has been completely withdrawn. Further, vascular graft 24a has been deployed, with the distal portion expanded within vessel 430 and the proximal portion expanded within branch graft 24.

Figure 96:
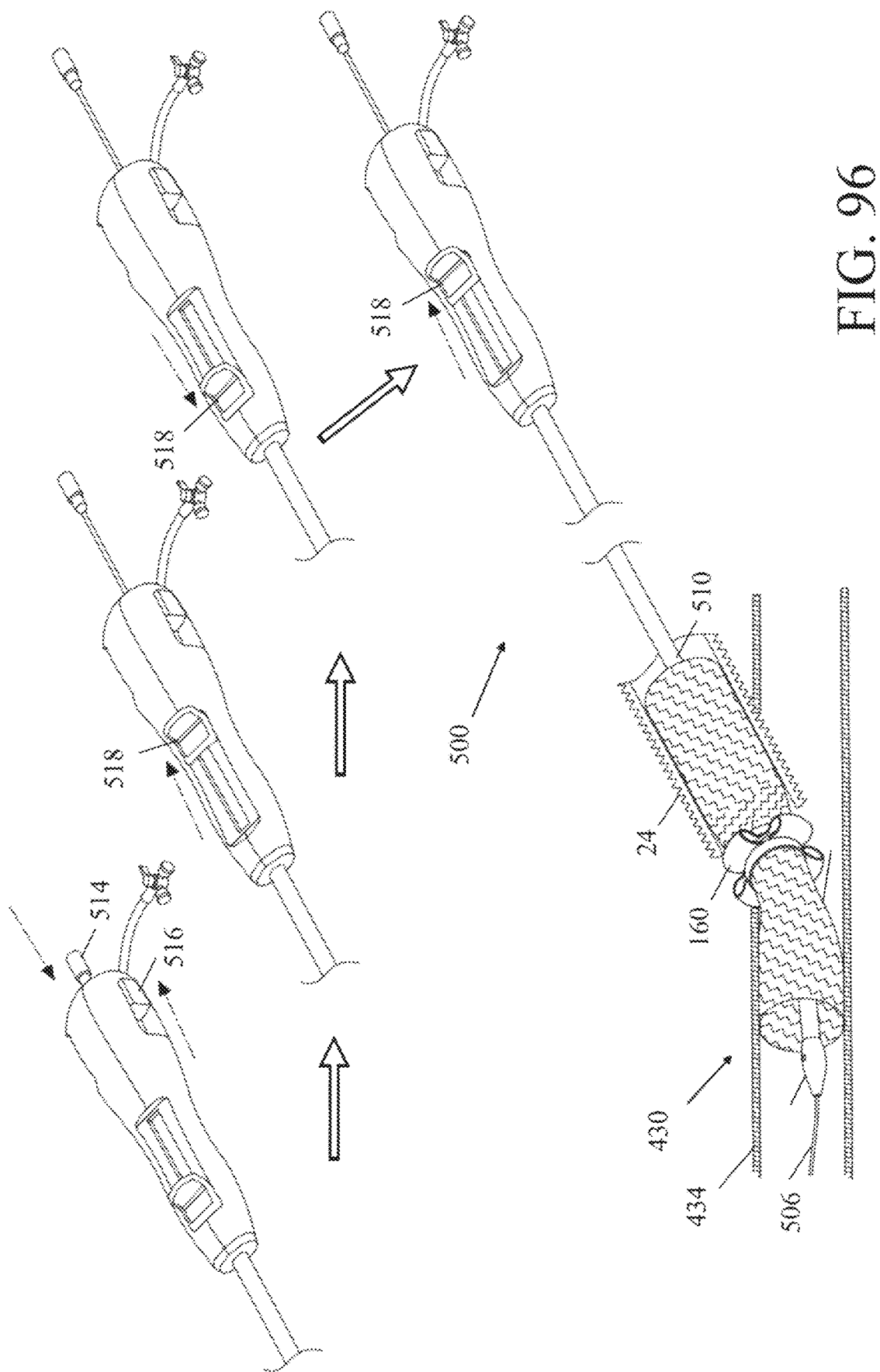
FIG. 96 is a schematic view of a sequence of operations involving an exemplary deployment tool during deployment of a vascular graft.

Referring also to FIG. 96, a sequence of operations involving deployment tool 500 are schematically shown. After penetrating vessel wall 434, needle 508 is automatically retracted as described above when guidewire 506 is advanced and guidewire grip 514 engages and releases needle advancement button 516. Next, a first cycle of actuator 518 from its distal position to its proximal position withdraws sheath 510 from a distal portion of vascular graft 24a, deploying that portion within vessel 430. Following the first cycle, actuator 518 returns to its distal position and then a second cycle of actuator 518 from its distal position to its proximal position causes further proximal movement of sheath 510 in order to deploy the proximal portion of vascular graft 24a within branch graft 24. As shown, the result of these operations, vascular graft 24a has been fully deployed within vessel 430 and branch graft 24, so that suture cuff 160 may be used to further secure vascular graft 24a as described above.

Figure 97:
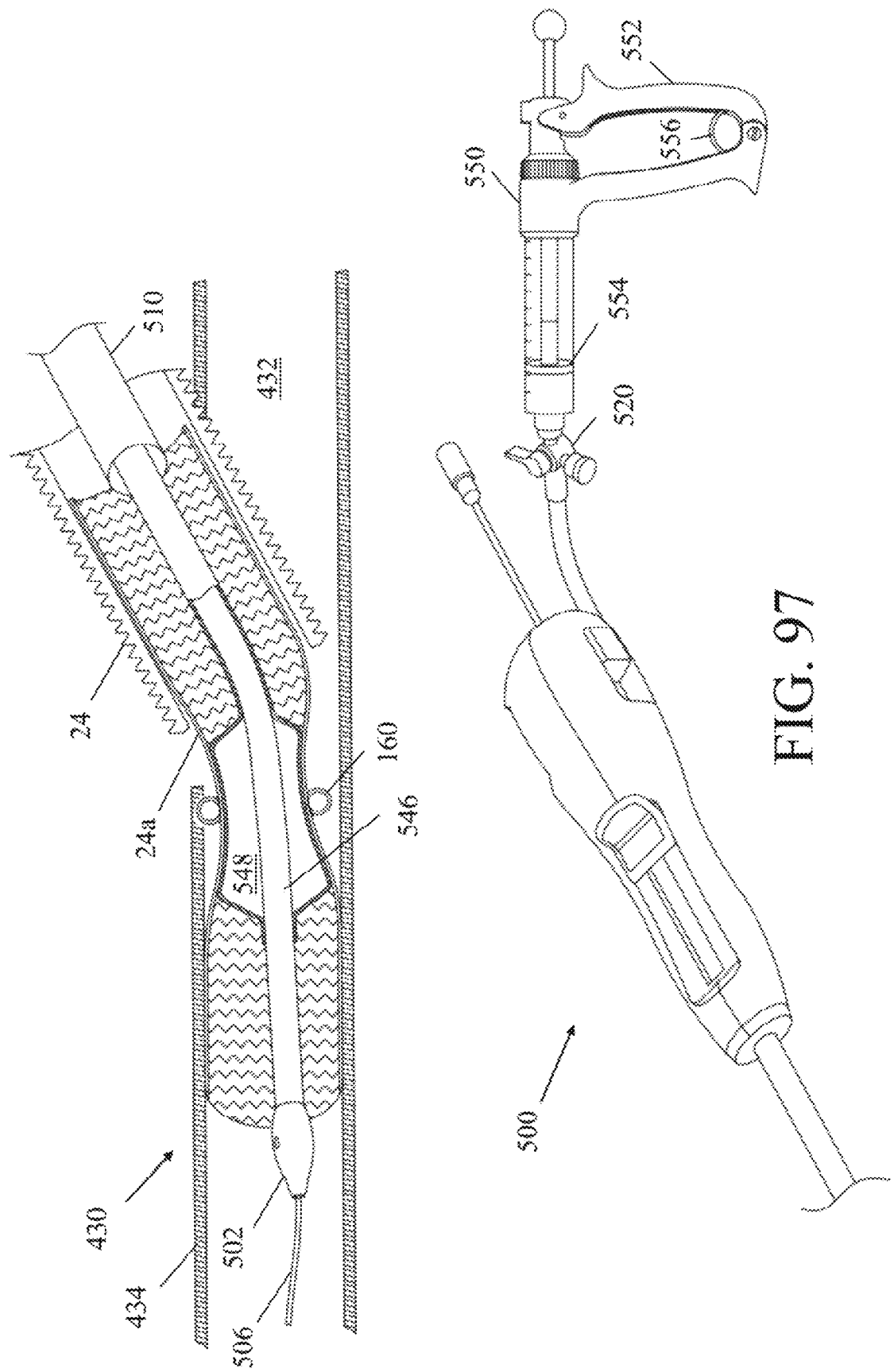
FIG. 97 is a side view of an exemplary deployment tool after inflation of a dilatation balloon.
Figure 98:
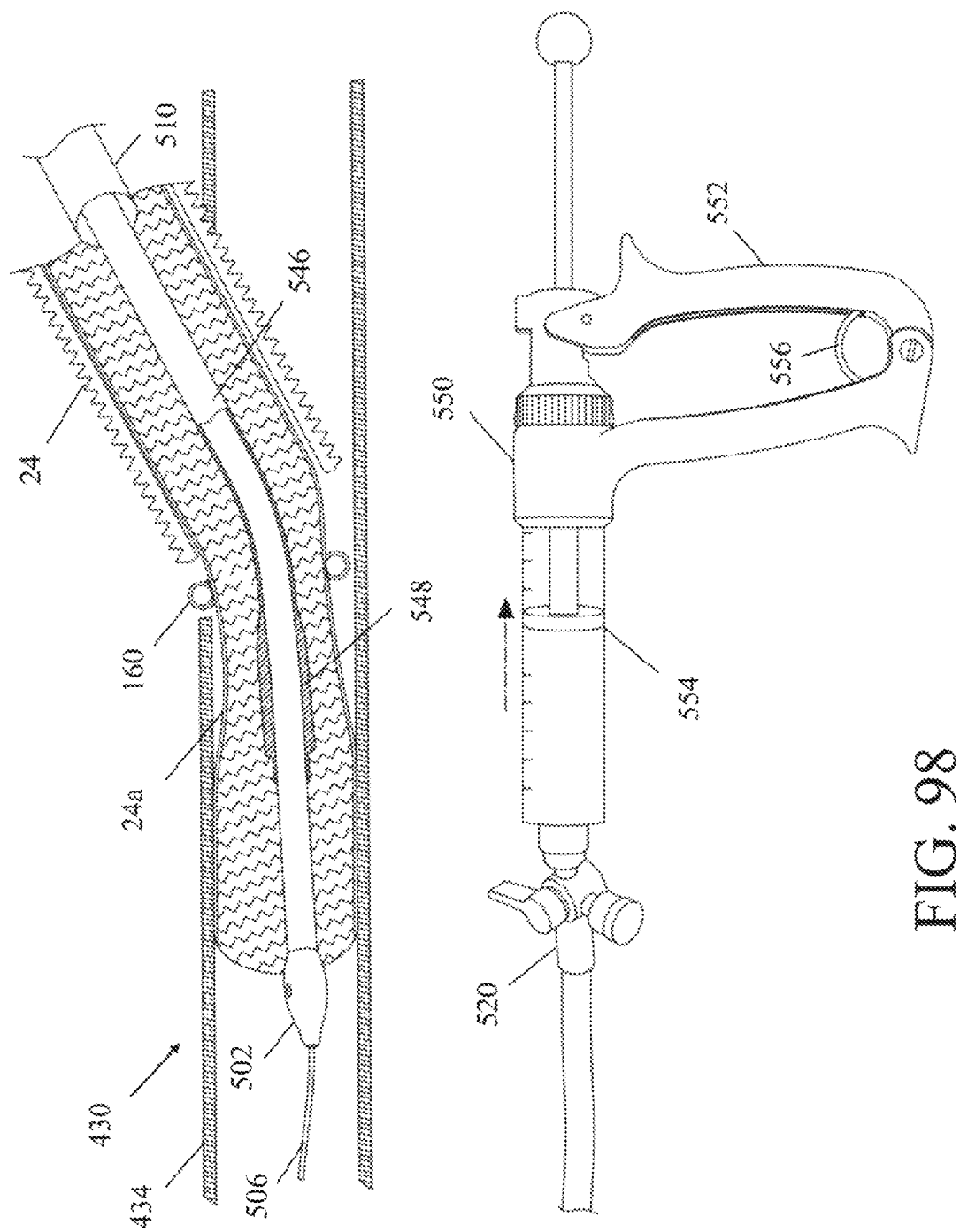
FIG. 98 is a side view of an exemplary deployment tool after deflation of a dilatation balloon.

When vascular graft 24a is deployed by an intra-vascular approach through opening 522 (shown in FIG. 86), there exists a potential for restriction at this arteriotomy, resulting in a "waist" or other impingement. Referring also now to FIG. 95, deployment tool 500 may also incorporate a dilatation balloon 548 disposed about mandrel 546 to address this situation. Prior to removal of deployment tool 500, a syringe gun 550 is attached to stop cock 520, such as through a luer fitting, to provide fluid communication with the interior of dilatation balloon 548. Operation of a trigger 552 causes a plunger 554 to deliver pressurized fluid into the balloon, dilating the segment of the stent within the arteriotomy releasing the stricture/waist. In some embodiments, a single stroke of trigger 552 that is used to deliver sufficient inflation fluid to inflate dilatation balloon 548 to a desired diameter at a desired pressure may culminate in a release of plunger 554, which may be driven by a spring 556 or otherwise biased to automatically return to a proximal position selected to draw a vacuum that will deflate the balloon. Deflation of balloon 548 reduces the risk of deployment tool 500 remaining engaged with the deployed vascular graft 24a during removal and correspondingly dislodging the graft. In other embodiments, syringe gun 550 may be configured so that a separate operation releases plunger 554, which likewise may result in the automatic application of a desired vacuum to cause deflation of the balloon. For example, syringe gun 550 may be configured to create an approximately 1 atm vacuum following inflation of dilatation balloon 548 using these or any other suitable techniques, although other pressures may be employed as warranted by the intended application. Referring also now to FIG. 97, operation of trigger 552 has caused plunger 554 to deliver sufficient fluid to inflate dilatation balloon 548, widening any stricture that may have existed. Subsequently, after the complete inflation of balloon 548 and referring also to FIG. 98, syringe gun 550 is configured to impart a vacuum as described above to deflate balloon 548 as shown. For example, plunger 554 may move proximally as shown to pull the vacuum, either automatically following a complete stroke of trigger 552 or in response to a separate actuation.

Figure 99:
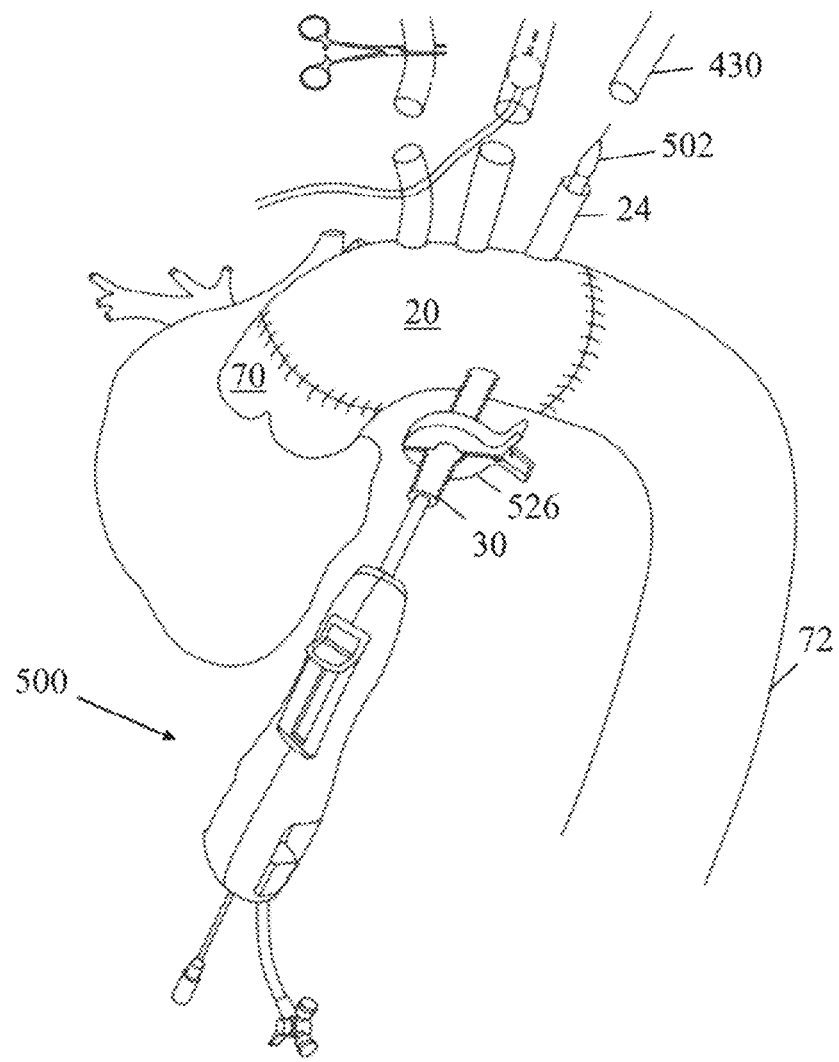
FIG. 99 is a perspective view of an exemplary deployment tool introduced through a venting port of an aortic graft.
Figure 100:
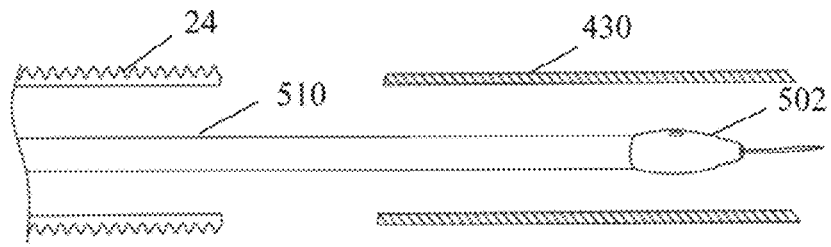
FIG. 100 is a side view of an exemplary deployment tool within a vessel.
Figure 101:
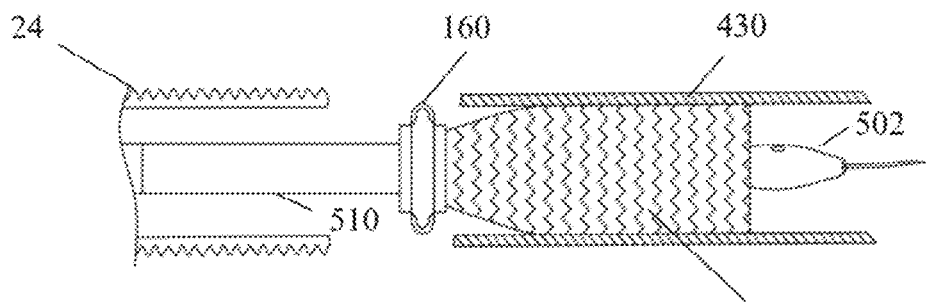
FIG. 101 is a side view of the deployment of a distal portion of a vascular graft within a vessel.
Figure 102:
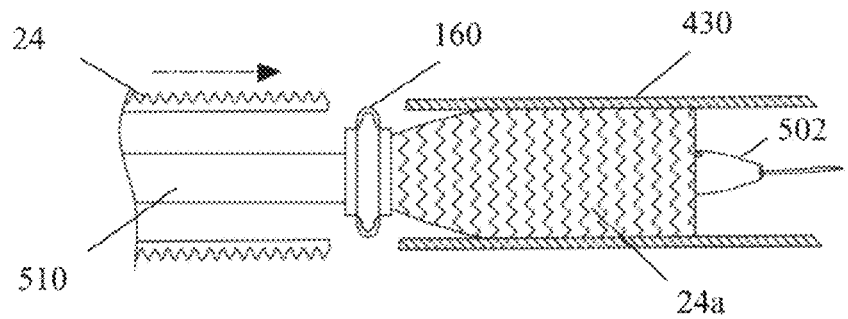
FIG. 102 is a side view of the positioning of a branch graft with respect to a a vascular graft following deployment of a distal portion of the vascular graft within a vessel.
Figure 103:
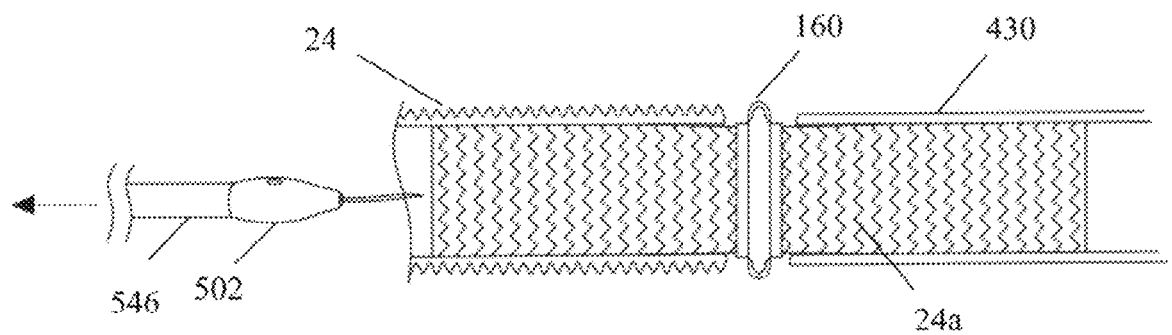
FIG. 103 is a side view of the deployment of a proximal portion of a vascular graft within a branch graft.

Although the above discussion has been in the context of employing deployment tool 500 with an intra-vascular approach, delivery of vascular graft 24a may also be performed in a manner that joins vessels, grafts or other lumens that conduct the patient's blood in an end-to-end configuration. Referring also to FIG. 99, a schematic example of this usage is depicted. As shown, the dilator tip 502 of deployment tool 500 may be introduced through a venting port 30 of aortic graft 20. Correspondingly, the dilator tip 502 then may be tracked from the aortic graft 20 through branch graft 24 and into vessel 430. In this embodiment, a graft clamp 526 as described above may be applied around venting port 30, again to reduce the flow/leakage of patient's blood during the procedure. Alternatively, or in addition, a graft clamp 526 may also be used on branch graft 24 as described above. Thus, referring also to FIG. 100, deployment tool 500 has been positioned so that dilator tip 502 and a distal portion of vascular graft 24a, which is still constrained by sheath 510, is located within vessel 430. Then referring also to FIG. 101, following a first cycle of actuator 518 as discussed above, a distal portion of vascular graft 24a has been deployed within vessel 430 by withdrawing sheath 510 proximally, also exposing suture cuff 160. Referring also to FIG. 102, once the distal portion of vascular graft 24a has been expanded within vessel 430 to secure it, the relative positioning of branch graft 24 can then be adjusted as desired. For example, but without limitation, in some embodiments a spacing of approximately 1 cm between the ends of vessel 430 and branch graft 24 is suitable, with suture cuff 160 positioned between the ends. Referring also to FIG. 103, the proximal portion of vascular graft 24a may then be deployed within branch graft 24 as shown.

As used in this document, and as customarily used in the art, the word "substantially" and similar terms of approximation refer to normal variations in the dimensions and other properties of finished goods that result from manufacturing tolerances and other manufacturing imprecisions.

While the invention has been described in detail, it will be apparent to one skilled in the art that various changes and modifications can be made and equivalents employed, without departing from the present invention. It is to be understood that the invention is not limited to the details of construction, the arrangements of components, and/or the method set forth in the above description or illustrated in the drawings. Statements in the abstract of this document, and any summary statements in this document, are merely exemplary; they are not, and cannot be interpreted as, limiting the scope of the claims. Further, the figures are merely exemplary and not limiting. Topical headings and subheadings are for the convenience of the reader only. They should not and cannot be construed to have any substantive significance, meaning or interpretation, and should not and cannot be deemed to indicate that all of the information relating to any particular topic is to be found under or limited to any particular heading or subheading. Therefore, the invention is not to be restricted or limited except in accordance with the claims and their legal equivalents.

What is claimed is:

1. A vascular graft configured to transition from an insertion state to a deployed state, comprising a proximal end having an expandable mesh, a distal end having an expandable mesh, and at least two intermediate sections positioned relatively closer to each other than to the proximal and distal ends of the vascular graft, the at least two intermediate sections comprising graft material connecting the proximal and distal ends along a longitudinal axis such that the proximal and distal ends are separated by a first distance in the insertion state, at least one of the at least two intermediate sections having a first outside diameter in the insertion state and being configured to contract along the longitudinal axis to form, in part by compression of the vascular graft substantially in the longitudinal direction, an outwardly extending suture cuff between the proximal and distal ends when the vascular graft transitions from the insertion state to the deployed state such that the suture cuff formed from the at least two intermediate sections has a second outside diameter greater than the first outside diameter and the proximal and distal ends are separated by a second distance in the deployed state, the second distance being less than the first distance.

2. The vascular graft of claim 1, wherein the transition from the insertion state to the deployed state is a self-expanding expansion.

3. The vascular graft of claim 1, wherein at least one of the two intermediate sections comprises at least two longitudinal slits defined therethrough and wherein expansion of the vascular graft is configured to cause portions of the at least one of the two intermediate sections which comprise the longitudinal slits to form lobes extending radially outward from the vascular graft.

4. A method for implanting a vascular graft within a patient, comprising providing the vascular graft having a proximal end with an expandable mesh, a distal end with an expandable mesh and at least two intermediate sections positioned relatively closer to each other than to the proximal and distal ends of the vascular graft, the at least two intermediate sections comprising graft material connecting the proximal and distal ends along a longitudinal axis such that the proximal and distal ends are separated by a first distance and the at least one of the at least two intermediate sections having a first outside diameter in an insertion state, positioning at least one end of the vascular graft within a lumen for conducting blood of the patient, expanding the vascular graft from the insertion state to a deployed state, which contracts the at least one intermediate section along the longitudinal axis to form, in part by compression of the vascular graft substantially in the longitudinal direction, at least one outwardly extending suture cuff between the proximal and distal ends, such that the suture cuff formed from the at least two intermediate sections has a second outside diameter greater than the first outside diameter and the proximal and distal ends are separated by a second distance in the deployed state, the second distance being less than the first distance, and securing the least one outwardly extending suture cuff of the vascular graft to a wall of the lumen for conducting blood of the patient by suturing with suture material.

5. The method of claim 4, further comprising positioning an opposing end of the vascular graft within another lumen for conducting blood of the patient and securing a second outwardly extending suture cuff between the proximal and distal ends of the vascular graft to a wall of the another lumen for conducting blood of the patient by suturing with suture material.

* * * * *